United States Patent [19]
DeMaggio et al.

[11] Patent Number: 5,728,806
[45] Date of Patent: Mar. 17, 1998

[54] TIH1, PROTEIN THAT INTERACTS WITH CASEIN KINASE I

[75] Inventors: Anthony J. DeMaggio, Kirkland; Merl F. Hoekstra, Shohomish, both of Wash.

[73] Assignee: ICOS Corporation, Bothell, Wash.

[21] Appl. No.: 468,036

[22] Filed: Jun. 6, 1995

Related U.S. Application Data

[62] Division of Ser. No. 184,605, Jan. 21, 1994, abandoned.

[51] Int. Cl.$^6$ ............... C07K 14/395; C12N 15/31
[52] U.S. Cl. ............... 530/350; 435/69.1; 435/69.7; 536/23.74
[58] Field of Search ............................ 530/350

[56] References Cited

PUBLICATIONS

Anderson, et al., "Human cellular src gene: nucleotide sequence and derived amino acid aequence of the region coding for the carboxy-terminal two-thirds of pp60$^{c-src}$," *Mol. Cell.Biol.* 5:1122–1129 (1985).
Bishop, et al., "Molecular themes in oncogenesis," *Cell* 64:235–248 (1991).
Bonner, et al., "The complete coding sequence of the human raf oncogene and the corresponding structure of c-raf-1 gene," *Nucl.Acids Res.* 14:1009–1015 (1986).
Brockman, et al., "Cell cycle dependent localization of casein kinase I to mitotic spindles," *Proc.Natl.Acad. Sci*(USA) 89:9454–9458 (1992).
Chien, et al., "The two-hybrid system: a method to identify and clone genes for a protein that interacts with a protein of interest," *Proc.Natl.Acad.Sci.* (*USA*) 88:9578–9582 (1991).
DeMaggio, e tal., "The budding yeast HRR25 gene product is a casein kinase I isoform," *Proc.Natl.Acad.Sci.* (*USA*) 89:7008–7012 (1992).
Durfee, et al., "The retinoblastoma protein associates with the protein phosphatase type 1 catalytic subunit," *Genes and Dev.* 7:555–569 (1993).
Edelman, et al., "Protein serine/threonine kinases," *Ann.Rev.Biochem.* 56:567–613 (1987).
Field, et al., "Purification of a RAS-responsive adenyl cyclase complex from *Saccharomyces cerevisiae* by use of an epitope addition method, " *Mol.Cell.Biol.* 8:2159–2165 (1988).
Fields and Song, "A novel genetic system to detect protein-protein interaction," *Nature* 340:245–246 (1989).
Graves, et al., "Molecular cloning, expression, and characterization of a 49–kilodation casein kinase I isofrom from rat testis," *J.Biol.Chem.* 268:6394–6401 (1993).
Guarente, "Yeast promotors and lacZ fusions designed to study expression of cloned genes in yeast," *Meth.Enzymol.* 101:181–191 (1983).
Hoekstra, et al., "HRR25, a putative protein kinase from budding yeast: association with repair of damaged DNA," *Science* 235:1031–1034 (1991).

Hoyt, et al., "Two *Saccharomyces cerevisiae* kinase–related gene products required for mitotic spindle assembly," *J.Cell. Biol.* 118, 109–120 (1992).
Hubbard and Cohen, "On target with a new mewchanism for the regulation of protein phosphorlyation," *TIBS* 18:172–177 (1993).
Ito, et al., "Transformation of intact yeast cells trated with alkali cation," *J.Bacteriol.* 153:163–168 (1983).
Herskowitz and Jenson, "Putting the HO gene to work: practical uses for mating–type switching," *Meth.Enzymol.* 194:132–146 (1991).
Luban, et al., "Human immunodeficieny virus type I gag protein binds to cyclophilins A and B,"*Cell* 73:1067–1078 (1993).
Meluh and Rose, "KAR3, a kinesin–related gene required for yeast nuclear fusion," *Cell* 60:1029–1041 (1990).
Pearson and Kemp, "Protein kinase phosphorylation site sequences and consensus specifity motifs: tabulations," *Meth.Enzymol.* 200:62–81 (1991).
Riles, et al., "Physical maps of the six smallest chromosomes of *Saccharomyces cerevisae* at a resolution of 2.6 kilobase pairs," *Genetics* 134:81–150 (1993).
Roof, et al., "Kinesin–related proteins required for assembly of the mitotic spindle," *J.Cell.Biol.* 118:95–108 (1992).
Robinson, et al., "Yeast casein kinase I homologues: An essential gene pair," *Proc. Natl. Acad. Sci. USA* 89:28–32 (1992).
Rothstein, et al., "Targeting, disrupting, replacement, and allele rescue: integrative DNA transformation in yeast," *Meth.Enzymol.* 194:21–37 (1991).
Rowles, et al., "Purification of casein kinase I and isolation of cDNAs encoding multiple casein kinase I–like enzymes," *Proc.Natl.Acad.Sci.* (*USA*) 88:9548–9552 (1991).
Sherman, et al. "Micromanipulation and dissection of asci," *Meth.Enzymol.* 194:281–3012 (1991).
Vojtek, et al., "Mammalian ras interacts directly with a serine/threonine kinase raf," *Cell* 74:205–214 (1993).
Wang, et al., "Two genes in *Saccaromyces cerevisiae* encode a membrane–bound form of casein kinase I," *J.Mol.Biol. Cell* 3:275–276 (1992).
Watson, et al., "Human DNA sequence homologous to the transforming gene (mos) of Moloney murine sarcoma virus," *Proc. Natl. Acad. Sci.* (*USA*) 739:4078–4082 (1982).
Yang, et al., "A protein kinase substrate identified by the two–hybrid system," *Science* 257: 681–682 (1992).
DeAntoni et al. Hypothetical proteins YNL118c—yeast (*Saccharomyces cerevisiae*). pir50 database Accession Nos. S63059 and S59701, Apr. 27, 1996.

*Primary Examiner*—David L. Fitzgerald
*Assistant Examiner*—Brian K. Lathrop
*Attorney, Agent, or Firm*—Marshall, O'Toole, Gerstein, Murray & Borun

[57] ABSTRACT

The present invention relates generally to identification of proteins, designated TIH proteins, that interact with casein kinase I isoforms and to isolation of polynucleotides encoding the same.

1 Claim, 1 Drawing Sheet

SEQUENCE LISTING ( 1 ) GENERAL INFORMATION:

( i i i ) NUMBER OF SEQUENCES: 48

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Arg  Arg  Xaa  Ser  Tyr
        1                          5

( 2 ) INFORMATION FOR SEQ ID NO:2:

( i ) SEQUENCE CHARACTERISTICS:
    ( A ) LENGTH: 2625 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 796..2580

( x i ) SEQUENCE DESCRIPTION: SEQ ID NO:2:

```
CATTTTCTTA ATTCTTTTAT GTGCTTTTAC TACTTTGTTT AGTTCAAAAC AATAGTCGTT        60

ATTCTTAGGT ACTATAGCAT AAGACAAGAA AAGAAAAATA AGGGACAAAT AACATTAGCA       120

GAAGTACGGT ATATTTACT GTTACTTATA TACTTTCAAG AAGATGAGTT AAATCGGTAG        180

CCAGTGTAGA AAAATAATAA TAAGGGTCAT CGATCCTTCG CATTTTATTA TCCAATTAAA       240

GATACGAATC ACGGCAAACT ATATTCAAAG CTCATAGATA ATCGTCGTAA GGCTGACACT       300

GCAGAAGAAA AGTCATAATT TGAATACTAG CCGGTATGAA ACTGTGATTG ATTAACCTGG       360

GGTTACCTAA AGAGAACATA AGTAATACTC ATGACAGAAT CAAAACACAA TACAAAATTT       420

ATCCGAACCT CGGCCCGACT GCGGCTCGCC GGGAAGGGG  ACAACCGCTT CTATCCGTCG       480

ACTAACTTCA TCGGCCCAAT GGAAGCTATG ATATGGGGAT TTCCATTGAG CCGATAGCAA       540

TGTAGGGTAA TACTGTTGCG TATATAGTGA TAGTTATTGA ATTTATTAC  CCTGCGGGAA       600

TATTGAGACA TCACTAAGCA CGAATTTTAC GTCTGAGGAA AGTTGAATGA TGGCCAAATA       660

ACCAGGAAAA ACAAATATTG AATCCTTGTG AAGGATTCCA CAGTTGTTTA ATCCTCCTTA       720

AGCTCACTTA GTATCAATTG TCTAAATAAT ATTGCTTTGA ATCTGAAAAA AATAAAAGTA       780

CCTTCGCATT AGACA ATG TCA CTG CCG CTA CGA CAC GCA TTG GAG AAC GTT       831
                 Met Ser Leu Pro Leu Arg His Ala Leu Glu Asn Val
                  1               5                  10
```

```
ACT TCT GTT GAT AGA ATT TTA GAG GAC TTA TTA GTA CGT TTT ATT ATA        879
Thr Ser Val Asp Arg Ile Leu Glu Asp Leu Leu Val Arg Phe Ile Ile
         15                  20                  25

AAT TGT CCG AAT GAA GAT TTA TCG AGT GTC GAG AGA GAG TTA TTT CAT        927
Asn Cys Pro Asn Glu Asp Leu Ser Ser Val Glu Arg Glu Leu Phe His
     30                  35                  40

TTT GAA GAA GCC TCA TGG TTT TAC ACG GAT TTC ATC AAA TTG ATG AAT        975
Phe Glu Glu Ala Ser Trp Phe Tyr Thr Asp Phe Ile Lys Leu Met Asn
 45                  50                  55                  60

CCA ACT TTA CCC TCC CTA AAG ATT AAA TCA TTT GCT CAA TTG ATC ATA       1023
Pro Thr Leu Pro Ser Leu Lys Ile Lys Ser Phe Ala Gln Leu Ile Ile
                 65                  70                  75

AAA CTA TGT CCT CTG GTT TGG AAA TGG GAC ATA AGA GTG GAT GAG GCA       1071
Lys Leu Cys Pro Leu Val Trp Lys Trp Asp Ile Arg Val Asp Glu Ala
             80                  85                  90

CTC CAG CAA TTC TCC AAG TAT AAG AAA AGT ATA CCG GTG AGG GGC GCT       1119
Leu Gln Gln Phe Ser Lys Tyr Lys Lys Ser Ile Pro Val Arg Gly Ala
         95                 100                 105

GCC ATA TTT AAC GAG AAC CTG AGT AAA ATT TTA TTG GTA CAG GGT ACT       1167
Ala Ile Phe Asn Glu Asn Leu Ser Lys Ile Leu Leu Val Gln Gly Thr
     110                 115                 120

GAA TCG GAT TCT TTG TCA TTC CCA AGG GGG AAG ATA TCT AAA GAT GAA       1215
Glu Ser Asp Ser Leu Ser Phe Pro Arg Gly Lys Ile Ser Lys Asp Glu
125                 130                 135                 140

AAT GAC ATA GAT TGT TGC ATT AGA GAA GTG AAA GAA GAA ATT GGT TTC       1263
Asn Asp Ile Asp Cys Cys Ile Arg Glu Val Lys Glu Glu Ile Gly Phe
                 145                 150                 155
```

```
GAT TTG ACG GAC TAT ATT GAC GAC AAC CAA TTC ATT GAA AGA AAT ATT        1311
Asp Leu Thr Asp Tyr Ile Asp Asp Asn Gln Phe Ile Glu Arg Asn Ile
            160             165                 170

CAA GGT AAA AAT TAC AAA ATA TTT TTG ATA TCT GGT GTT TCA GAA GTC        1359
Gln Gly Lys Asn Tyr Lys Ile Phe Leu Ile Ser Gly Val Ser Glu Val
        175             180              185

TTC AAT TTT AAA CCT CAA GTT AGA AAT GAA ATT GAT AAG ATA GAA TGG        1407
Phe Asn Phe Lys Pro Gln Val Arg Asn Glu Ile Asp Lys Ile Glu Trp
    190             195              200

TTC GAT TTT AAG AAA ATT TCT AAA ACA ATG TAC AAA TCA AAT ATC AAG        1455
Phe Asp Phe Lys Lys Ile Ser Lys Thr Met Tyr Lys Ser Asn Ile Lys
205             210             215                 220

TAT TAT CTG ATT AAT TCC ATG ATG AGA CCC TTA TCA ATG TGG TTA AGG        1503
Tyr Tyr Leu Ile Asn Ser Met Met Arg Pro Leu Ser Met Trp Leu Arg
                225             230                 235

CAT CAG AGG CAA ATA AAA AAT GAA GAT CAA TTG AAA TCC TAT GCG GAA        1551
His Gln Arg Gln Ile Lys Asn Glu Asp Gln Leu Lys Ser Tyr Ala Glu
        240             245              250

GAA CAA TTG AAA TTG TTG TTG GGT ATC ACT AAG GAG GAG CAG ATT GAT        1599
Glu Gln Leu Lys Leu Leu Leu Gly Ile Thr Lys Glu Glu Gln Ile Asp
        255             260              265

CCC GGT AGA GAG TTG CTG AAT ATG TTA CAT ACT GCA GTG CAA GCT AAC        1647
Pro Gly Arg Glu Leu Leu Asn Met Leu His Thr Ala Val Gln Ala Asn
    270             275              280

AGT AAT AAT AAT GCG GTC TCC AAC GGA CAG GTA CCC TCG AGC CAA GAG        1695
Ser Asn Asn Asn Ala Val Ser Asn Gly Gln Val Pro Ser Ser Gln Glu
285             290              295             300

CTT CAG CAT TTG AAA GAG CAA TCA GGA GAA CAC AAC CAA CAG AAG GAT        1743
Leu Gln His Leu Lys Glu Gln Ser Gly Glu His Asn Gln Gln Lys Asp
                305             310                 315

CAG CAG TCA TCG TTT TCT TCT CAA CAA CAA CCT TCA ATA TTT CCA TCT        1791
Gln Gln Ser Ser Phe Ser Ser Gln Gln Gln Pro Ser Ile Phe Pro Ser
        320             325              330

CTT TCT GAA CCG TTT GCT AAC AAT AAG AAT GTT ATA CCA CCT ACT ATG        1839
Leu Ser Glu Pro Phe Ala Asn Asn Lys Asn Val Ile Pro Pro Thr Met
        335             340              345

CCA ATG GCT AAC GTA TTC ATG TCA AAT CCT CAA TTG TTT GCG ACA ATG        1887
Pro Met Ala Asn Val Phe Met Ser Asn Pro Gln Leu Phe Ala Thr Met
    350             355              360

AAT GGC CAG CCT TTT GCA CCT TTC CCA TTT ATG TTA CCA TTA ACT AAC        1935
Asn Gly Gln Pro Phe Ala Pro Phe Pro Phe Met Leu Pro Leu Thr Asn
365             370              375             380

AAT AGT AAT AGC GCT AAC CCT ATT CCA ACT CCG GTC CCC CCT AAT TTT        1983
Asn Ser Asn Ser Ala Asn Pro Ile Pro Thr Pro Val Pro Pro Asn Phe
                385             390                 395

AAT GCT CCT CCG AAT CCG ATG GCT TTT GGT GTT CCA AAC ATG CAT AAC        2031
Asn Ala Pro Pro Asn Pro Met Ala Phe Gly Val Pro Asn Met His Asn
        400             405              410

CTT TCT GGA CCA GCA GTA TCT CAA CCG TTT TCC TTG CCT CCT GCT CCT        2079
Leu Ser Gly Pro Ala Val Ser Gln Pro Phe Ser Leu Pro Pro Ala Pro
        415             420              425

TTA CCG AGG GAC TCT GGT TAC AGC AGC TCC TCC CCT GGG CAG TTG TTA        2127
Leu Pro Arg Asp Ser Gly Tyr Ser Ser Ser Ser Pro Gly Gln Leu Leu
    430             435              440

GAT ATA CTA AAT TCG AAA AAG CCT GAC AGC AAC GTG CAA TCA AGC AAA        2175
Asp Ile Leu Asn Ser Lys Lys Pro Asp Ser Asn Val Gln Ser Ser Lys
445             450             455                 460

AAG CCA AAG CTT AAA ATC TTA CAG AGA GGA ACG GAC TTG AAT TCA CTC        2223
Lys Pro Lys Leu Lys Ile Leu Gln Arg Gly Thr Asp Leu Asn Ser Leu
                465             470                 475
```

| | | | | | | | | | | | | | | | | |
|---|---|---|---|---|---|---|---|---|---|---|---|---|---|---|---|---|
| AAG | CAA | AAC | AAT | AAT | GAT | GAA | ACT | GCT | CAT | TCA | AAC | TCT | CAA | GCT | TTG | 2271 |
| Lys | Gln | Asn | Asn 480 | Asn | Asp | Glu | Thr | Ala 485 | His | Ser | Asn | Ser | Gln 490 | Ala | Leu | |
| CTA | GAT | TTG | TTG | AAA | AAA | CCA | ACA | TCA | TCG | CAG | AAG | ATA | CAC | GCT | TCC | 2319 |
| Leu | Asp | Leu 495 | Leu | Lys | Lys | Pro | Thr 500 | Ser | Ser | Gln | Lys | Ile 505 | His | Ala | Ser | |
| AAA | CCA | GAT | ACT | TCC | TTT | TTA | CCA | AAT | GAC | TCC | GTA | TCT | GGT | ATA | CAA | 2367 |
| Lys | Pro 510 | Asp | Thr | Ser | Phe | Leu 515 | Pro | Asn | Asp | Ser | Val 520 | Ser | Gly | Ile | Gln | |
| GAT | GCA | GAA | TAT | GAA | GAT | TTC | GAG | AGT | AGT | TCA | GAT | GAA | GAG | GTG | GAG | 2415 |
| Asp 525 | Ala | Glu | Tyr | Glu 530 | Asp | Phe | Glu | Ser | Ser 535 | Ser | Asp | Glu | Glu | Val | Glu 540 | |
| ACA | GCT | AGA | GAT | GAA | AGA | AAT | TCA | TTG | AAT | GTA | GAT | ATT | GGG | GTG | AAC | 2463 |
| Thr | Ala | Arg | Asp | Glu 545 | Arg | Asn | Ser | Leu | Asn 550 | Val | Asp | Ile | Gly | Val 555 | Asn | |
| GTT | ATG | CCA | AGC | GAA | AAA | GAC | AGC | CGA | AGA | AGT | CAA | AAG | GAA | AAA | CCA | 2511 |
| Val | Met | Pro | Ser 560 | Glu | Lys | Asp | Ser | Arg 565 | Arg | Ser | Gln | Lys | Glu 570 | Lys | Pro | |
| AGG | AAC | GAC | GCA | AGC | AAA | ACA | AAC | TTG | AAC | GCT | TCT | GCA | GAA | TCT | AAT | 2559 |
| Arg | Asn | Asp | Ala | Ser 575 | Lys | Thr | Asn | Leu | Asn 580 | Ala | Ser | Ala | Glu 585 | Ser | Asn | |
| AGT | GTA | GAA | TGG | GGG | GCT | GGG | TAAATCTTCA | | CCCTCCGACT | | TCAGAGTAAC | | | | | 2610 |
| Ser | Val | Glu | Trp | Gly | Ala 590 | Gly 595 | | | | | | | | | | |
| ACAGAATCCA | CAGTA | | | | | | | | | | | | | | | 2625 |

( 2 ) INFORMATION FOR SEQ ID NO:3:

( i ) SEQUENCE CHARACTERISTICS:
        ( A ) LENGTH: 595 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Met 1 | Ser | Leu | Pro | Leu 5 | Arg | His | Ala | Leu | Glu 10 | Asn | Val | Thr | Ser | Val 15 | Asp |
| Arg | Ile | Leu | Glu 20 | Asp | Leu | Leu | Val | Arg 25 | Phe | Ile | Ile | Asn | Cys 30 | Pro | Asn |
| Glu | Asp | Leu 35 | Ser | Ser | Val | Glu | Arg 40 | Glu | Leu | Phe | His | Phe 45 | Glu | Glu | Ala |
| Ser | Trp 50 | Phe | Tyr | Thr | Asp | Phe 55 | Ile | Lys | Leu | Met | Asn 60 | Pro | Thr | Leu | Pro |
| Ser 65 | Leu | Lys | Ile | Lys | Ser 70 | Phe | Ala | Gln | Leu | Ile 75 | Ile | Lys | Leu | Cys | Pro 80 |
| Leu | Val | Trp | Lys | Trp 85 | Asp | Ile | Arg | Val | Asp 90 | Glu | Ala | Leu | Gln | Gln 95 | Phe |
| Ser | Lys | Tyr | Lys 100 | Lys | Ser | Ile | Pro | Val 105 | Arg | Gly | Ala | Ala | Ile 110 | Phe | Asn |
| Glu | Asn | Leu 115 | Ser | Lys | Ile | Leu | Leu 120 | Val | Gln | Gly | Thr | Glu 125 | Ser | Asp | Ser |
| Leu | Ser 130 | Phe | Pro | Arg | Gly | Lys 135 | Ile | Ser | Lys | Asp | Glu 140 | Asn | Asp | Ile | Asp |
| Cys 145 | Cys | Ile | Arg | Glu | Val 150 | Lys | Glu | Glu | Ile | Gly 155 | Phe | Asp | Leu | Thr | Asp 160 |
| Tyr | Ile | Asp | Asp | Asn 165 | Gln | Phe | Ile | Glu | Arg 170 | Asn | Ile | Gln | Gly | Lys 175 | Asn |

-continued

| | | | | | | | | | | | | | | |
|---|---|---|---|---|---|---|---|---|---|---|---|---|---|---|
| Tyr | Lys | Ile | Phe | Leu | Ile | Ser | Gly | Val | Ser | Glu | Val | Phe | Asn | Phe | Lys |
| | | | 180 | | | | | 185 | | | | | 190 | | |
| Pro | Gln | Val | Arg | Asn | Glu | Ile | Asp | Lys | Ile | Glu | Trp | Phe | Asp | Phe | Lys |
| | | 195 | | | | 200 | | | | | | 205 | | | |
| Lys | Ile | Ser | Lys | Thr | Met | Tyr | Lys | Ser | Asn | Ile | Lys | Tyr | Tyr | Leu | Ile |
| 210 | | | | | 215 | | | | | | 220 | | | | |
| Asn | Ser | Met | Met | Arg | Pro | Leu | Ser | Met | Trp | Leu | Arg | His | Gln | Arg | Gln |
| 225 | | | | | 230 | | | | | 235 | | | | | 240 |
| Ile | Lys | Asn | Glu | Asp | Gln | Leu | Lys | Ser | Tyr | Ala | Glu | Gln | Leu | Lys |
| | | | | 245 | | | | | 250 | | | | | 255 |
| Leu | Leu | Leu | Gly | Ile | Thr | Lys | Glu | Gln | Ile | Asp | Pro | Gly | Arg | Glu |
| | | | 260 | | | | | 265 | | | | | 270 | |
| Leu | Leu | Asn | Met | Leu | His | Thr | Ala | Val | Gln | Ala | Asn | Ser | Asn | Asn | Asn |
| | | 275 | | | | | 280 | | | | | 285 | | | |
| Ala | Val | Ser | Asn | Gly | Gln | Val | Pro | Ser | Ser | Gln | Glu | Leu | Gln | His | Leu |
| 290 | | | | | 295 | | | | | 300 | | | | | |
| Lys | Glu | Gln | Ser | Gly | Glu | His | Asn | Gln | Gln | Lys | Asp | Gln | Gln | Ser | Ser |
| 305 | | | | | 310 | | | | | 315 | | | | | 320 |
| Phe | Ser | Ser | Gln | Gln | Gln | Pro | Ser | Ile | Phe | Pro | Ser | Leu | Ser | Glu | Pro |
| | | | | 325 | | | | | 330 | | | | | 335 | |
| Phe | Ala | Asn | Asn | Lys | Asn | Val | Ile | Pro | Pro | Thr | Met | Pro | Met | Ala | Asn |
| | | | 340 | | | | | 345 | | | | | 350 | | |
| Val | Phe | Met | Ser | Asn | Pro | Gln | Leu | Phe | Ala | Thr | Met | Asn | Gly | Gln | Pro |
| | | | 355 | | | | | 360 | | | | | 365 | | |
| Phe | Ala | Pro | Phe | Pro | Phe | Met | Leu | Pro | Leu | Thr | Asn | Asn | Ser | Asn | Ser |
| | | 370 | | | | | 375 | | | | | 380 | | | |
| Ala | Asn | Pro | Ile | Pro | Thr | Pro | Val | Pro | Pro | Asn | Phe | Asn | Ala | Pro | Pro |
| 385 | | | | | 390 | | | | | 395 | | | | | 400 |
| Asn | Pro | Met | Ala | Phe | Gly | Val | Pro | Asn | Met | His | Asn | Leu | Ser | Gly | Pro |
| | | | | 405 | | | | | 410 | | | | | 415 | |
| Ala | Val | Ser | Gln | Pro | Phe | Ser | Leu | Pro | Pro | Ala | Pro | Leu | Pro | Arg | Asp |
| | | | 420 | | | | | 425 | | | | | 430 | | |
| Ser | Gly | Tyr | Ser | Ser | Ser | Ser | Pro | Gly | Gln | Leu | Leu | Asp | Ile | Leu | Asn |
| | | | 435 | | | | | 440 | | | | | 445 | | |
| Ser | Lys | Lys | Pro | Asp | Ser | Asn | Val | Gln | Ser | Ser | Lys | Lys | Pro | Lys | Leu |
| | 450 | | | | | 455 | | | | | 460 | | | | |
| Lys | Ile | Leu | Gln | Arg | Gly | Thr | Asp | Leu | Asn | Ser | Leu | Lys | Gln | Asn | Asn |
| 465 | | | | | 470 | | | | | 475 | | | | | 480 |
| Asn | Asp | Glu | Thr | Ala | His | Ser | Asn | Ser | Gln | Ala | Leu | Leu | Asp | Leu | Leu |
| | | | | 485 | | | | | 490 | | | | | 495 | |
| Lys | Lys | Pro | Thr | Ser | Ser | Gln | Lys | Ile | His | Ala | Ser | Lys | Pro | Asp | Thr |
| | | | | 500 | | | | | 505 | | | | | 510 | |
| Ser | Phe | Leu | Pro | Asn | Asp | Ser | Val | Ser | Gly | Ile | Gln | Asp | Ala | Glu | Tyr |
| | | | 515 | | | | | 520 | | | | | 525 | | |
| Glu | Asp | Phe | Glu | Ser | Ser | Ser | Asp | Glu | Glu | Val | Glu | Thr | Ala | Arg | Asp |
| | 530 | | | | | 535 | | | | | 540 | | | | |
| Glu | Arg | Asn | Ser | Leu | Asn | Val | Asp | Ile | Gly | Val | Asn | Val | Met | Pro | Ser |
| 545 | | | | | 550 | | | | | 555 | | | | | 560 |
| Glu | Lys | Asp | Ser | Arg | Arg | Ser | Gln | Lys | Glu | Lys | Pro | Arg | Asn | Asp | Ala |
| | | | | 565 | | | | | 570 | | | | | 575 | |
| Ser | Lys | Thr | Asn | Leu | Asn | Ala | Ser | Ala | Glu | Ser | Asn | Ser | Val | Glu | Trp |
| | | | 580 | | | | | 585 | | | | | 590 | | |
| Gly | Ala | Gly |
| | | 595 |

( 2 ) INFORMATION FOR SEQ ID NO:4:

( i ) SEQUENCE CHARACTERISTICS:
        ( A ) LENGTH: 6854 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 2050..4053

( x i ) SEQUENCE DESCRIPTION: SEQ ID NO:4:

```
AGCTTCTCCC TTTTCCTTCA GTGCTGCTAC TCTCTGCTCT CCACTTAAGT GTTACAATTA      60
ATTTGCAGCT AGTTTGCAGT TCGTACAACC TCGCCTATTC TTGTAACGAA GAAGAACGTA     120
TTTATAATAT TGGGCTGTAA TGTGTTGAGT TTAGTAATAG ATAAAGTAGG ACAGAGTTCT     180
GTCTTTGTTT ATCTATGGGG TTCAGAGTGA TAAGGGGCAG GATAAGGAAG TTAAAAAAAA     240
AAAGGTTACG TTATATAACG AAAGAAAAGA AACGAGCGAA GTGCCAACTA TAGCCCAATA     300
TCAAGAATGC AAGTCAGCAA AGTACAGTAA TCGTATGAAG ATACGCGATG CGTAATATCC     360
CTCAAGGGCT CCGGATCAGA AAAGCTAAGG GAAGATCCTT ACATTACACG GCGTGCGACA     420
GACTCGAACC ACAGCTAACT TCTCGTGAAA AGATGGCTTC AACTTCGCTC TTGCAATAAC     480
TTTGAAACAC ACGAACAAAG GTTTATTGCG CTTGATTAAC GTTGGAAGTA TATGATACTA     540
ATACTACTTT GTTCTCTAAG TCATCGCTAT ATGTTTATCT CGAGGAAAAG GTGCACGGCG     600
GTACACAATT ACTTCGCCGT TTCGGGTAAA ACAAGTGTTA CATTTATAAT ATATATGTAT     660
ATATGTATGT GCGCGTAAGT ATATGCCGTT CATAACAAAT CATCTTCTTG TTGCTGGATG     720
GACTCCTTAA TTTTATTCAA AATGGTAATT TTCCATTTAT CTAGTCTCAT AAAATTGTCA     780
AACTCCTTAC AGTGTTCGCT TAGCTGCTCG CTATCACCTT CATTAACAGC ATCGATTAAA     840
CTTTTCAAGA AATTTGACTC CCTTGAATCC GCAAAATTCG GATCTTCACT TTGACCCTCT     900
TGTAAAGTTC TTGCAGCAGC GACTGCATCA GTAGCAGCTA GCTGACAAAG CCCTTTTTTT     960
AGGAAGTAAT CCTTCAAACT CCATTGGCTC AATCTATTGC CCATGCTGCT CTTGATCAAC    1020
TTCGAATATA TATCACTTGC TTCAATATAT TGACCGTCAA GAGCCTTTAG ATCTGCGCAT    1080
TTGATAAAAC ACTTATTCGA TAATGCTACC GACTGGTCTT GGGCATACCA CTCACCAGCG    1140
AGCTCATAGC AATCTATAGC TTTTGCATAG TCATGCAAAT CATTTCTAG AATTTCTCCA    1200
AGCTCAAACT TGAAATTAGC ACCTCTCCGG AACTGCCCCC TATGAGTAAA AATTTGAATA    1260
GCATTTTCTA ATGAATCCAC GGCGTTCACA GAGTTTCCAC CGCTTTTAAA GCATTTATAA    1320
GCCTCTACGT AGGTATTTCC TGCTTCGTCT TCATTACCAG CCTTTTTCTG ATAGTCAGCA    1380
GCTTTCAAAA ACGAGTCTCC TGCCAAGTTT AACTCTTTTC TTAGACGGTA AATGGTGGCT    1440
GCTTGGACAC AAAGATCAGC AGCCTCCTCA AACTTGTATG AATCAGAACC GCTAAACAAT    1500
TTCATGAAAC CCGATGAAGG AACACCCTTC TTCTCAGCCT TAACACAACG GGAAATATCA    1560
ATTCCCGTAT TTCAATGTTA GTAATTTGCC TTCGTAAATT ACGGAATCAC ATAGCTTTCA    1620
TTTTGTTCCT TTGATATATT TCCCTACTAC ATACTCTTTT CAATAACTCT ACAGGGTCTG    1680
ACATTTTTAA CTTTCAGGTT AATGATGGTG TTCTTACTAT ATTCTCGAGT CGTACAGAAG    1740
TTAGTTCAGA TAAACTGCTT CGGTGCTGCC CACTTCTTAT CATTACTTCA ACTTTACCTT    1800
CCCTATACCT GTGTGTCCTT ATTAATTCAA GTTAATCCGA GGTAATAGAT TAGGGTAACC    1860
```

-continued

```
TTCAATGATG TCACGAAACA CGGATGCTGC AACTTTGCGA TTTTTCCTG GAAAAGAATA         1920

ACAATTAAAG GCAGCCTTTC AGCTGAGATT ACCAGCAGGT CTTTGGAGAT TAGCGCAAGA         1980

AGAAGTGTGA TATAGTACTC ATAGAGGCAG GCTACAGACT AGGGAAAGCG TGTTCAACAA         2040

CAATAAGAA ATG GAG ACC AGT TCT TTT GAG AAT GCT CCT CCT GCA GCC             2088
          Met Glu Thr Ser Ser Phe Glu Asn Ala Pro Pro Ala Ala
            1               5                  10

ATC AAT GAT GCT CAG GAT AAT AAT ATA AAT ACG GAG ACT AAT GAC CAG           2136
Ile Asn Asp Ala Gln Asp Asn Asn Ile Asn Thr Glu Thr Asn Asp Gln
 15              20                  25

GAA ACA AAT CAG CAA TCT ATC GAA ACT AGA GAT GCA ATT GAC AAA GAA           2184
Glu Thr Asn Gln Gln Ser Ile Glu Thr Arg Asp Ala Ile Asp Lys Glu
 30              35                  40                      45

AAC GGT GTG CAA ACG GAA ACT GGT GAG AAC TCT GCA AAA AAT GCC GAA           2232
Asn Gly Val Gln Thr Glu Thr Gly Glu Asn Ser Ala Lys Asn Ala Glu
                 50                  55                  60

CAA AAC GTT TCT TCT ACA AAT TTG AAT AAT GCC CCC ACC AAT GGT GCT           2280
Gln Asn Val Ser Ser Thr Asn Leu Asn Asn Ala Pro Thr Asn Gly Ala
                 65                  70                  75

TTG GAC GAT GAT GTT ATC CCA AAT GCT ATT GTT ATT AAA AAC ATT CCG           2328
Leu Asp Asp Asp Val Ile Pro Asn Ala Ile Val Ile Lys Asn Ile Pro
                 80                  85                  90

TTT GCT ATT AAA AAA GAG CAA TTG TTA GAC ATT ATT GAA GAA ATG GAT           2376
Phe Ala Ile Lys Lys Glu Gln Leu Leu Asp Ile Ile Glu Glu Met Asp
 95                 100                 105

CTT CCC CTT CCT TAT GCC TTC AAT TAC CAC TTT GAT AAC GGT ATT TTC           2424
Leu Pro Leu Pro Tyr Ala Phe Asn Tyr His Phe Asp Asn Gly Ile Phe
110                 115                 120                     125

AGA GGA CTA GCC TTT GCG AAT TTC ACC ACT CCT GAA GAA ACT ACT CAA           2472
Arg Gly Leu Ala Phe Ala Asn Phe Thr Thr Pro Glu Glu Thr Thr Gln
                130                 135                 140

GTG ATA ACT TCT TTG AAT GGA AAG GAA ATC AGC GGG AGG AAA TTG AAA           2520
Val Ile Thr Ser Leu Asn Gly Lys Glu Ile Ser Gly Arg Lys Leu Lys
                145                 150                 155

GTG GAA TAT AAA AAA ATG CTT CCC CAA GCT GAA AGA GAA AGA ATC GAG           2568
Val Glu Tyr Lys Lys Met Leu Pro Gln Ala Glu Arg Glu Arg Ile Glu
                160                 165                 170

AGG GAG AAG AGA GAG AAA AGA GGA CAA TTA GAA GAA CAA CAC AGA TCG           2616
Arg Glu Lys Arg Glu Lys Arg Gly Gln Leu Glu Glu Gln His Arg Ser
175                 180                 185

TCA TCT AAT CTT TCT TTG GAT TCT TTA TCT AAA ATG AGT GGA AGC GGA           2664
Ser Ser Asn Leu Ser Leu Asp Ser Leu Ser Lys Met Ser Gly Ser Gly
190                 195                 200                     205

AAC AAT AAT ACT TCT AAC AAT CAA TTA TTC TCG ACT CTA ATG AAC GGC           2712
Asn Asn Asn Thr Ser Asn Asn Gln Leu Phe Ser Thr Leu Met Asn Gly
                210                 215                     220

ATT AAT GCT AAT AGC ATG ATG AAC AGT CCA ATG AAT AAT ACC ATT AAC           2760
Ile Asn Ala Asn Ser Met Met Asn Ser Pro Met Asn Asn Thr Ile Asn
                225                 230                 235

AAT AAC AGT TCT AAT AAC AAC AAT AGT GGT AAC ATC ATT CTG AAC CAA           2808
Asn Asn Ser Ser Asn Asn Asn Asn Ser Gly Asn Ile Ile Leu Asn Gln
                240                 245                 250

CCT TCA CTT TCT GCC CAA CAT ACT TCT TCA TCG TTG TAC CAA ACA AAC           2856
Pro Ser Leu Ser Ala Gln His Thr Ser Ser Ser Leu Tyr Gln Thr Asn
255                 260                 265

GTT AAT AAT CAA GCC CAG ATG TCC ACT GAG AGA TTT TAT GCG CCT TTA           2904
Val Asn Asn Gln Ala Gln Met Ser Thr Glu Arg Phe Tyr Ala Pro Leu
270                 275                 280                     285

CCA TCA ACT TCC ACT TTG CCT CTC CCA CCC CAA CAA CTG GAC TTC AAT           2952
Pro Ser Thr Ser Thr Leu Pro Leu Pro Pro Gln Gln Leu Asp Phe Asn
```

-continued

|     |     |     | 290 |     |     |     | 295 |     |     |     |     | 300 |     |     |      |
|-----|-----|-----|-----|-----|-----|-----|-----|-----|-----|-----|-----|-----|-----|-----|------|
| GAC | CCT | GAC | ACT | TTG | GAA | ATT | TAT | TCC | CAA | TTA | TTG | TTA | TTT | AAG | GAT  | 3000
| Asp | Pro | Asp | Thr | Leu | Glu | Ile | Tyr | Ser | Gln | Leu | Leu | Leu | Phe | Lys | Asp  |
|     |     |     | 305 |     |     |     | 310 |     |     |     |     | 315 |     |     |      |

```
AGA  GAA  AAG  TAT  TAT  TAC  GAG  TTG  GCT  TAT  CCC  ATG  GGT  ATA  TCC  GCT       3048
Arg  Glu  Lys  Tyr  Tyr  Tyr  Glu  Leu  Ala  Tyr  Pro  Met  Gly  Ile  Ser  Ala
              320                 325                 330

TCC  CAC  AAG  AGA  ATT  ATC  AAT  GTT  TTG  TGC  TCG  TAC  TTA  GGG  CTA  GTA       3096
Ser  His  Lys  Arg  Ile  Ile  Asn  Val  Leu  Cys  Ser  Tyr  Leu  Gly  Leu  Val
     335                 340                 345

GAA  GTA  TAT  GAT  CCA  AGA  TTT  ATT  ATT  ATC  AGA  AGA  AAG  ATT  CTG  GAT       3144
Glu  Val  Tyr  Asp  Pro  Arg  Phe  Ile  Ile  Ile  Arg  Arg  Lys  Ile  Leu  Asp
350                 355                 360                 365

CAT  GCT  AAT  TTA  CAA  TCT  CAT  TTG  CAA  CAA  CAA  GGT  CAA  ATG  ACA  TCT       3192
His  Ala  Asn  Leu  Gln  Ser  His  Leu  Gln  Gln  Gln  Gly  Gln  Met  Thr  Ser
                370                 375                 380

GCT  CAT  CCT  TTG  CAG  CCA  AAC  TCC  ACT  GGC  GGC  TCC  ATG  AAT  AGG  TCA       3240
Ala  His  Pro  Leu  Gln  Pro  Asn  Ser  Thr  Gly  Gly  Ser  Met  Asn  Arg  Ser
               385                 390                 395

CAA  TCT  TAT  ACA  AGT  TTG  TTA  CAG  GCC  CAT  GCA  GCA  GCT  GCA  GCG  AAT       3288
Gln  Ser  Tyr  Thr  Ser  Leu  Leu  Gln  Ala  His  Ala  Ala  Ala  Ala  Ala  Asn
              400                 405                 410

AGT  ATT  AGC  AAT  CAG  GCC  GTT  AAC  AAT  TCT  TCC  AAC  AGC  AAT  ACT  ATT       3336
Ser  Ile  Ser  Asn  Gln  Ala  Val  Asn  Asn  Ser  Ser  Asn  Ser  Asn  Thr  Ile
     415                 420                 425

AAC  AGT  AAT  AAC  GGT  AAC  GGT  AAC  AAT  GTC  ATC  ATT  AAT  AAC  AAT  AGC       3384
Asn  Ser  Asn  Asn  Gly  Asn  Gly  Asn  Asn  Val  Ile  Ile  Asn  Asn  Asn  Ser
430                 435                 440                 445

GCC  AGC  TCA  ACA  CCA  AAA  ATT  TCT  TCA  CAG  GGA  CAA  TTC  TCC  ATG  CAA       3432
Ala  Ser  Ser  Thr  Pro  Lys  Ile  Ser  Ser  Gln  Gly  Gln  Phe  Ser  Met  Gln
               450                 455                 460

CCA  ACA  CTA  ACC  TCA  CCT  AAA  ATG  AAC  ATA  CAC  CAT  AGT  TCT  CAA  TAC       3480
Pro  Thr  Leu  Thr  Ser  Pro  Lys  Met  Asn  Ile  His  His  Ser  Ser  Gln  Tyr
              465                 470                 475

AAT  TCC  GCA  GAC  CAA  CCG  CAA  CAA  CCT  CAA  CCA  CAA  ACA  CAG  CAA  AAT       3528
Asn  Ser  Ala  Asp  Gln  Pro  Gln  Gln  Pro  Gln  Pro  Gln  Thr  Gln  Gln  Asn
               480                 485                 490

GTT  CAG  TCA  GCT  GCG  CAA  CAA  CAA  CAA  TCT  TTT  TTA  AGA  CAA  CAA  GCT       3576
Val  Gln  Ser  Ala  Ala  Gln  Gln  Gln  Gln  Ser  Phe  Leu  Arg  Gln  Gln  Ala
     495                 500                 505

ACT  TTA  ACA  CCA  TCC  TCA  AGA  ATT  CCA  TCC  GGT  TAT  TCT  GCC  AAC  CAT       3624
Thr  Leu  Thr  Pro  Ser  Ser  Arg  Ile  Pro  Ser  Gly  Tyr  Ser  Ala  Asn  His
510                 515                 520                 525

TAT  CAA  ATC  AAT  TCC  GTT  AAT  CCC  TTA  CTG  AGA  AAT  TCT  CAA  ATT  TCA       3672
Tyr  Gln  Ile  Asn  Ser  Val  Asn  Pro  Leu  Leu  Arg  Asn  Ser  Gln  Ile  Ser
               530                 535                 540

CCT  CCA  AAT  TCA  CAA  ATC  CCA  ATC  AAC  AGC  CAA  ACC  CTA  TCC  CAA  GCG       3720
Pro  Pro  Asn  Ser  Gln  Ile  Pro  Ile  Asn  Ser  Gln  Thr  Leu  Ser  Gln  Ala
              545                 550                 555

CAA  CCA  CCA  GCA  CAG  TCC  CAA  ACT  CAA  CAA  CGG  GTA  CCA  GTG  GCA  TAC       3768
Gln  Pro  Pro  Ala  Gln  Ser  Gln  Thr  Gln  Gln  Arg  Val  Pro  Val  Ala  Tyr
               560                 565                 570

CAA  AAT  GCT  TCA  TTG  TCT  TCC  CAG  CAG  TTG  TAC  AAC  CTT  AAC  GGC  CCA       3816
Gln  Asn  Ala  Ser  Leu  Ser  Ser  Gln  Gln  Leu  Tyr  Asn  Leu  Asn  Gly  Pro
575                 580                 585

TCT  TCA  GCA  AAC  TCA  CAG  TCC  CAA  CTG  CTT  CCA  CAG  CAC  ACA  AAT  GGC       3864
Ser  Ser  Ala  Asn  Ser  Gln  Ser  Gln  Leu  Leu  Pro  Gln  His  Thr  Asn  Gly
590                 595                 600                 605

TCA  GTA  CAT  TCT  AAT  TTC  TCA  TAT  CAG  TCT  TAT  CAC  GAT  GAG  TCC  ATG       3912
Ser  Val  His  Ser  Asn  Phe  Ser  Tyr  Gln  Ser  Tyr  His  Asp  Glu  Ser  Met
```

```
                     610                      615                      620
TTG TCC GCA CAC AAT TTG AAT AGT GCC GAC TTG ATC TAT AAA TCT TTG              3960
Leu Ser Ala His Asn Leu Asn Ser Ala Asp Leu Ile Tyr Lys Ser Leu
            625                     630                     635

AGT CAC TCT GGA CTA GAT GAT GGC TTG GAA CAG GGC TTG AAT CGT TCT              4008
Ser His Ser Gly Leu Asp Asp Gly Leu Glu Gln Gly Leu Asn Arg Ser
            640                     645                     650

TTA AGC GGA CTG GAT TTA CAA AAC CAA AAC AAG AAG AAT CTA TGG                  4053
Leu Ser Gly Leu Asp Leu Gln Asn Gln Asn Lys Lys Asn Leu Trp
        655                     660                     665

TAATATATAC TTCCATTATT CTATGATTAT AGAGTTTGTT TGGTATTTGT ATATCGCACG            4113
ATACAAGTAA TGAGGGGTGC TTACACAAGA TAAAGATAA  AAAAATATAT ATATATAATA            4173
AAAACCATCA AAAACACCAT TGAAAAAAAA TATAAAAAAA AAAAAAAATA ACCGAATATG            4233
AATATGAAAT TAATGATCAT GATGAAGTTA ATTTTACTG  AGAAACGTCA CCTAATGTCG            4293
ATGAAACGAT GATAATGAAT GATGATGAG  GCTACTTTAA GTAACGCAAT GTAATCAAGC            4353
CAAAATTATC CCTCTTTTTT TTTTTTCCCT CTTTGAGAT  TTATTTTTA  ACCTACTACT            4413
TACTTTTTTT TTTGAACGT  TCTTTTCCCA CATACTTTTA TATATGGTAT TTATATGTAC            4473
GATGTTTAAT CACAGAGATG TTTCTACCTT ACTCGATATT GTTTTGCAT  TAATTGATAT            4533
CTTGCTCACT GCATCATTGG CGGTATTTGT AGTATATAGA AAGTCGGGTA ACAATAATTT            4593
ATTGACATTT CTTTGTTTAC AATGATCAGA GAAGAGCAGA AAGTTTCATA GTCAAACGTT            4653
CAGGCCAATT GAACAAGAAA TTATTCGTTT TTTTAGTCGT TGAGTGTTCA ACTGACATGC            4713
TATTTGGTG  GTTCTTGATT AATTGGGGGC TTCATTGTTT GAAATAAAGA GTCGGGAAAA            4773
TAGCACAGAA ACAAAGCATA TTAAAAGAGG CAAAAGAAGA AAGAACGAAT ATAAAAGGTA            4833
AAAAAGGAAA AGCATTGCTA TTCTTTTCTC ATAGGTGTTA TTCATACCGC CCTCTCTCTT            4893
CTTCCTTCTT CATTAATTAG TCTCCGTATA ATTTGCAGAT AATGTCATTA ACAGCAAACG            4953
ACGAATCGCC AAAACCCAAA AAAAATGCAT TATTGAAAAA CTTAGAGATC GATGATCTGA            5013
TACATTCTCA ATTTGTCAGA AGCGATACAA ATGGACATAG AACTACAAGA CGACTATTCA            5073
ACTCCGATGC CAGTATATCA CATCGAATAA GAGGAAGTGT TCGGTCTGAT AAAGGCCTTA            5133
ATAAATAAA  AAAAGGGTTG ATTTCCCAGC AGTCCAAACT TGCGTCAGAA AATTCTTCTC            5193
AAAATATCGT TAATAGGGAC AATAAGATGG GAGCAGTAAG TTTCCCCATT ATTGAACCTA            5253
ATATTGAAGT CAGCGAGGAG TTGAAGGTTA GAATTAAGTA TGATTCTATC AAATTTTTCA            5313
ATTTTGAAAG ACTAATATCT AAATCTTCAG TCATAGCACC TTTAGTTAAC AAAAATATAA            5373
CATCATCCGG TCCTCTAATC GGGTTTCAAA GAAGAGTTAA CAGGTTAAAG CAAACATGGG            5433
ATCTAGCAAC CGAAAACATG GAGTACCCAT ATTCTTCTGA TAATACGCCA TTCAGGGATA            5493
ACGATTCTTG GCAATGGTAC GTACCATACG GCGGAACAAT AAAAAAAATG AAAGATTTCA            5553
GTACAAAAAG AACTTTACCC ACCTGGGAAG ATAAATAAA  GTTCTTACA  TTTTAGAAA             5613
ACTCTAAGTC TGCAACGTAC ATTAATGGTA ACGTATCACT TTGCAATCAT AATGAAACCG            5673
ATCAAGAAAA CGAAGATAGG AAAAAAAGGA AAGGGAAAGT ACCAAGAATC AAAAATAAAG            5733
TGTGGTTTTC CCAGATAGAA TACATTGTTC TTCGAAATTA TGAAATTAAA CCTTGGTATA            5793
CATCTCCTTT TCCGGAACAC ATCAACCAAA ATAAATGGT  TTTTATATGT GAGTTCTGCC            5853
TAAAATATAT GACTTCTCGA TATACTTTTT ATAGACACCA ACTAAAGTGT CTAACTTTTA            5913
AGCCCCCCGG AAATGAAATT TATCGCGACG GTAAGCTGTC TGTTTGGGAA ATTGATGGGC            5973
GGGAGAATGT CTTGTATTGT CAAAATCTTT GCCTGTTGGC AAAATGTTTT ATCAATTCTA            6033
```

-continued

```
AGACTTTGTA TTACGATGTT GAACCGTTTA TATTCTATAT TCTAACGGAG AGAGAGGATA    6093
CAGAGAACCA TCCCTATCAA AACGCAGCCA AATTCCATTT CGTAGGCTAT TTCTCCAAGG    6153
AAAAATTCAA CTCCAATGAC TATAACCTAA GTTGTATTTT AACTCTACCC ATATACCAGA    6213
GGAAAGGATA TGGTCAGTTT TTGATGGAAT TTTCATATTT ATTATCCAGA AAGGAGTCAA    6273
AATTTGGAAC TCCTGAAAAA CCATTGTCGG ATTTAGGATT ATTGACTTAC AGAACGTTTT    6333
GGAAGATAAA ATGTGCTGAA GTGCTATTAA AATTAAGAGA CAGTGCTAGA CGTCGATCAA    6393
ATAATAAAAA TGAAGATACT TTTCAGCAGG TTAGCCTAAA CGATATCGCT AAACTAACAG    6453
GAATGATACC AACAGACGTT GTGTTTGGAT GGAACAACT TCAAGTTTTG TATCGCCATA     6513
AAACACGCTC ATTATCCAGT TTGGATGATT TCAACTATAT TATTAAAATC GATTCTTGGA    6573
ACAGGATTGA AATATTTAC AAAACTTGGA GCTCAAAAAA CTATCCTCGC GTCAAATATG     6633
ACAAACTATT GTGGGAACCT ATTATATTAG GGCCGTCATT TGGTATAAAT GGGATGATGA    6693
ACTTAGAACC CACCGCATTA GCGGACGAAG CTCTTACAAA TGAAACTATG GCTCCGGTAA    6753
TTTCGAATAA CACACATATA GAAAACTATA ACAACAGTAG AGCACATAAT AAACGCAGAA    6813
GAAGAAGAAG AAGAAGTAGT GAGCACAAAA CATCCAAGCT T                        6854
```

( 2 ) INFORMATION FOR SEQ ID NO:5:

( i ) SEQUENCE CHARACTERISTICS:
        ( A ) LENGTH: 668 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Glu Thr Ser Ser Phe Glu Asn Ala Pro Pro Ala Ala Ile Asn Asp
 1               5                  10                  15

Ala Gln Asp Asn Asn Ile Asn Thr Glu Thr Asn Asp Gln Glu Thr Asn
            20                  25                  30

Gln Gln Ser Ile Glu Thr Arg Asp Ala Ile Asp Lys Glu Asn Gly Val
        35                  40                  45

Gln Thr Glu Thr Gly Glu Asn Ser Ala Lys Asn Ala Glu Gln Asn Val
 50                  55                  60

Ser Ser Thr Asn Leu Asn Asn Ala Pro Thr Asn Gly Ala Leu Asp Asp
 65                  70                  75                  80

Asp Val Ile Pro Asn Ala Ile Val Ile Lys Asn Ile Pro Phe Ala Ile
                    85                  90                  95

Lys Lys Glu Gln Leu Leu Asp Ile Ile Glu Glu Met Asp Leu Pro Leu
            100                 105                 110

Pro Tyr Ala Phe Asn Tyr His Phe Asp Asn Gly Ile Phe Arg Gly Leu
        115                 120                 125

Ala Phe Ala Asn Phe Thr Thr Pro Glu Glu Thr Thr Gln Val Ile Thr
130                 135                 140

Ser Leu Asn Gly Lys Glu Ile Ser Gly Arg Lys Leu Lys Val Glu Tyr
145                 150                 155                 160

Lys Lys Met Leu Pro Gln Ala Glu Arg Glu Arg Ile Glu Arg Glu Lys
                    165                 170                 175

Arg Glu Lys Arg Gly Gln Leu Glu Glu Gln His Arg Ser Ser Ser Asn
            180                 185                 190

Leu Ser Leu Asp Ser Leu Ser Lys Met Ser Gly Ser Gly Asn Asn Asn
        195                 200                 205

Thr Ser Asn Asn Gln Leu Phe Ser Thr Leu Met Asn Gly Ile Asn Ala
```

-continued

|  |  |  |  |  | 210 |  |  |  |  | 215 |  |  |  |  | 220 |  |  |
|---|---|---|---|---|---|---|---|---|---|---|---|---|---|---|---|---|---|
| Asn | Ser | Met | Met | Asn | Ser | Pro | Met | Asn | Asn | Thr | Ile | Asn | Asn | Asn | Ser |  |  |
| 225 |  |  |  |  | 230 |  |  |  |  | 235 |  |  |  |  | 240 |  |  |
| Ser | Asn | Asn | Asn | Asn | Ser | Gly | Asn | Ile | Ile | Leu | Asn | Gln | Pro | Ser | Leu |
|  |  |  |  | 245 |  |  |  |  | 250 |  |  |  |  | 255 |  |
| Ser | Ala | Gln | His | Thr | Ser | Ser | Ser | Leu | Tyr | Gln | Thr | Asn | Val | Asn | Asn |
|  |  |  |  | 260 |  |  |  |  | 265 |  |  |  |  | 270 |  |
| Gln | Ala | Gln | Met | Ser | Thr | Glu | Arg | Phe | Tyr | Ala | Pro | Leu | Pro | Ser | Thr |
|  |  |  | 275 |  |  |  |  | 280 |  |  |  |  | 285 |  |  |
| Ser | Thr | Leu | Pro | Leu | Pro | Pro | Gln | Gln | Leu | Asp | Phe | Asn | Asp | Pro | Asp |
|  |  | 290 |  |  |  |  | 295 |  |  |  |  | 300 |  |  |  |
| Thr | Leu | Glu | Ile | Tyr | Ser | Gln | Leu | Leu | Leu | Phe | Lys | Asp | Arg | Glu | Lys |
| 305 |  |  |  |  | 310 |  |  |  |  | 315 |  |  |  |  | 320 |
| Tyr | Tyr | Tyr | Glu | Leu | Ala | Tyr | Pro | Met | Gly | Ile | Ser | Ala | Ser | His | Lys |
|  |  |  |  | 325 |  |  |  |  | 330 |  |  |  |  | 335 |  |
| Arg | Ile | Ile | Asn | Val | Leu | Cys | Ser | Tyr | Leu | Gly | Leu | Val | Glu | Val | Tyr |
|  |  |  | 340 |  |  |  |  | 345 |  |  |  |  | 350 |  |  |
| Asp | Pro | Arg | Phe | Ile | Ile | Ile | Arg | Arg | Lys | Ile | Leu | Asp | His | Ala | Asn |
|  |  | 355 |  |  |  |  | 360 |  |  |  |  | 365 |  |  |  |
| Leu | Gln | Ser | His | Leu | Gln | Gln | Gln | Gly | Gln | Met | Thr | Ser | Ala | His | Pro |
|  | 370 |  |  |  |  | 375 |  |  |  |  | 380 |  |  |  |  |
| Leu | Gln | Pro | Asn | Ser | Thr | Gly | Gly | Ser | Met | Asn | Arg | Ser | Gln | Ser | Tyr |
| 385 |  |  |  |  | 390 |  |  |  |  | 395 |  |  |  |  | 400 |
| Thr | Ser | Leu | Leu | Gln | Ala | His | Ala | Ala | Ala | Ala | Ala | Asn | Ser | Ile | Ser |
|  |  |  |  | 405 |  |  |  |  | 410 |  |  |  |  | 415 |  |
| Asn | Gln | Ala | Val | Asn | Asn | Ser | Ser | Asn | Ser | Asn | Thr | Ile | Asn | Ser | Asn |
|  |  |  | 420 |  |  |  |  | 425 |  |  |  |  | 430 |  |  |
| Asn | Gly | Asn | Gly | Asn | Asn | Val | Ile | Ile | Asn | Asn | Asn | Ser | Ala | Ser | Ser |
|  |  |  | 435 |  |  |  |  | 440 |  |  |  |  | 445 |  |  |
| Thr | Pro | Lys | Ile | Ser | Ser | Gln | Gly | Gln | Phe | Ser | Met | Gln | Pro | Thr | Leu |
|  | 450 |  |  |  |  | 455 |  |  |  |  | 460 |  |  |  |  |
| Thr | Ser | Pro | Lys | Met | Asn | Ile | His | His | Ser | Ser | Gln | Tyr | Asn | Ser | Ala |
| 465 |  |  |  |  | 470 |  |  |  |  | 475 |  |  |  |  | 480 |
| Asp | Gln | Pro | Gln | Gln | Pro | Gln | Pro | Gln | Thr | Gln | Gln | Asn | Val | Gln | Ser |
|  |  |  |  | 485 |  |  |  |  | 490 |  |  |  |  | 495 |  |
| Ala | Ala | Gln | Gln | Gln | Gln | Ser | Phe | Leu | Arg | Gln | Gln | Ala | Thr | Leu | Thr |
|  |  |  | 500 |  |  |  |  | 505 |  |  |  |  | 510 |  |  |
| Pro | Ser | Ser | Arg | Ile | Pro | Ser | Gly | Tyr | Ser | Ala | Asn | His | Tyr | Gln | Ile |
|  |  | 515 |  |  |  |  | 520 |  |  |  |  | 525 |  |  |  |
| Asn | Ser | Val | Asn | Pro | Leu | Leu | Arg | Asn | Ser | Gln | Ile | Ser | Pro | Pro | Asn |
|  | 530 |  |  |  |  | 535 |  |  |  |  | 540 |  |  |  |  |
| Ser | Gln | Ile | Pro | Ile | Asn | Ser | Gln | Thr | Leu | Ser | Gln | Ala | Gln | Pro | Pro |
| 545 |  |  |  |  | 550 |  |  |  |  | 555 |  |  |  |  | 560 |
| Ala | Gln | Ser | Gln | Thr | Gln | Gln | Arg | Val | Pro | Val | Ala | Tyr | Gln | Asn | Ala |
|  |  |  |  | 565 |  |  |  |  | 570 |  |  |  |  | 575 |  |
| Ser | Leu | Ser | Ser | Gln | Gln | Leu | Tyr | Asn | Leu | Asn | Gly | Pro | Ser | Ser | Ala |
|  |  |  | 580 |  |  |  |  | 585 |  |  |  |  | 590 |  |  |
| Asn | Ser | Gln | Ser | Gln | Leu | Leu | Pro | Gln | His | Thr | Asn | Gly | Ser | Val | His |
|  |  | 595 |  |  |  |  | 600 |  |  |  |  | 605 |  |  |  |
| Ser | Asn | Phe | Ser | Tyr | Gln | Ser | Tyr | His | Asp | Glu | Ser | Met | Leu | Ser | Ala |
|  | 610 |  |  |  |  | 615 |  |  |  |  | 620 |  |  |  |  |
| His | Asn | Leu | Asn | Ser | Ala | Asp | Leu | Ile | Tyr | Lys | Ser | Leu | Ser | His | Ser |
| 625 |  |  |  |  | 630 |  |  |  |  | 635 |  |  |  |  | 640 |

Gly Leu Asp Asp Gly Leu Glu Gln Gly Leu Asn Arg Ser Leu Ser Gly
            645                 650                 655

Leu Asp Leu Gln Asn Gln Asn Lys Lys Asn Leu Trp
            660                 665

( 2 ) INFORMATION FOR SEQ ID NO:6:

( i ) SEQUENCE CHARACTERISTICS:
        ( A ) LENGTH: 2814 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..696

( x i ) SEQUENCE DESCRIPTION: SEQ ID NO:6:

| | | | | | | | | | | | | | | | | |
|---|---|---|---|---|---|---|---|---|---|---|---|---|---|---|---|---|
| GAA | TTC | CAA | TAC | ACC | AAA | CAG | CTG | CAT | TTC | CCT | GTG | GGG | CCC | AAA | TCC | 48 |
| Glu | Phe | Gln | Tyr | Thr | Lys | Gln | Leu | His | Phe | Pro | Val | Gly | Pro | Lys | Ser | |
| 1 | | | | 5 | | | | | 10 | | | | | 15 | | |
| ACA | AAC | TGT | GAG | GTA | GCG | GAA | ATT | CTT | TTA | CAC | TGC | GAC | TGG | GAA | AGG | 96 |
| Thr | Asn | Cys | Glu | Val | Ala | Glu | Ile | Leu | Leu | His | Cys | Asp | Trp | Glu | Arg | |
| | | | 20 | | | | | 25 | | | | | 30 | | | |
| TAC | ATA | AAT | GTT | TTA | AGT | ATA | ACA | AGA | ACA | CCA | AAT | GTT | CCT | AGT | GGT | 144 |
| Tyr | Ile | Asn | Val | Leu | Ser | Ile | Thr | Arg | Thr | Pro | Asn | Val | Pro | Ser | Gly | |
| | | 35 | | | | | 40 | | | | | 45 | | | | |
| ACC | AGT | TTC | AGC | ACC | AGA | ACG | AGG | TAC | ATG | TTC | CGA | TGG | GAT | GAC | CAG | 192 |
| Thr | Ser | Phe | Ser | Thr | Arg | Thr | Arg | Tyr | Met | Phe | Arg | Trp | Asp | Asp | Gln | |
| | 50 | | | | | 55 | | | | | 60 | | | | | |
| GGG | CAA | GGT | TGC | ATA | TTA | AAA | ATA | AGT | TTT | TGG | GTG | GAC | TGG | AAC | GCA | 240 |
| Gly | Gln | Gly | Cys | Ile | Leu | Lys | Ile | Ser | Phe | Trp | Val | Asp | Trp | Asn | Ala | |
| 65 | | | | | 70 | | | | | 75 | | | | | 80 | |
| TCC | AGT | TGG | ATC | AAG | CCA | ATG | GTA | GAG | AGC | AAT | TGT | AAA | AAT | GGA | CAA | 288 |
| Ser | Ser | Trp | Ile | Lys | Pro | Met | Val | Glu | Ser | Asn | Cys | Lys | Asn | Gly | Gln | |
| | | | | 85 | | | | | 90 | | | | | 95 | | |
| ATT | AGC | GCC | ACT | AAG | GAC | TTG | GTA | AAG | TTA | GTC | GAA | GAA | TTT | GTA | GAG | 336 |
| Ile | Ser | Ala | Thr | Lys | Asp | Leu | Val | Lys | Leu | Val | Glu | Glu | Phe | Val | Glu | |
| | | | 100 | | | | | 105 | | | | | 110 | | | |
| AAA | TAC | GTG | GAA | TTG | AGC | AAA | GAA | AAA | GCA | GAT | ACA | CTC | AAG | CCG | TTG | 384 |
| Lys | Tyr | Val | Glu | Leu | Ser | Lys | Glu | Lys | Ala | Asp | Thr | Leu | Lys | Pro | Leu | |
| | | 115 | | | | | 120 | | | | | 125 | | | | |
| CCC | AGT | GTT | ACA | TCT | TTT | GGA | TCA | CCT | AGG | AAA | GTG | GCA | GCA | CCG | GAG | 432 |
| Pro | Ser | Val | Thr | Ser | Phe | Gly | Ser | Pro | Arg | Lys | Val | Ala | Ala | Pro | Glu | |
| | 130 | | | | | 135 | | | | | 140 | | | | | |
| CTG | TCG | ATG | GTA | CAG | CCG | GAG | TCG | AAA | CCA | GAA | GCT | GAG | GCG | GAA | ATC | 480 |
| Leu | Ser | Met | Val | Gln | Pro | Glu | Ser | Lys | Pro | Glu | Ala | Glu | Ala | Glu | Ile | |
| 145 | | | | | 150 | | | | | 155 | | | | | 160 | |
| TCA | GAA | ATA | GGC | AGC | GAC | AGA | TGG | AGG | TTT | AAC | TGG | GTG | AAC | ATA | ATA | 528 |
| Ser | Glu | Ile | Gly | Ser | Asp | Arg | Trp | Arg | Phe | Asn | Trp | Val | Asn | Ile | Ile | |
| | | | | 165 | | | | | 170 | | | | | 175 | | |
| ATC | TTG | GTG | CTC | TTG | GTG | TTA | AAT | CTG | CTG | TAT | TTA | ATG | AAG | TTG | AAC | 576 |
| Ile | Leu | Val | Leu | Leu | Val | Leu | Asn | Leu | Leu | Tyr | Leu | Met | Lys | Leu | Asn | |
| | | | 180 | | | | | 185 | | | | | 190 | | | |
| AAG | AAG | ATG | GAT | AAG | CTG | ACG | AAC | CTC | ATG | ACC | CAC | AAG | GAC | GAA | GTT | 624 |
| Lys | Lys | Met | Asp | Lys | Leu | Thr | Asn | Leu | Met | Thr | His | Lys | Asp | Glu | Val | |
| | | 195 | | | | | 200 | | | | | 205 | | | | |
| GTA | GCG | CAC | GCG | ACT | CTA | TTG | GAC | ATA | CCA | GCC | CAA | GTA | CAA | TGG | TCA | 672 |
| Val | Ala | His | Ala | Thr | Leu | Leu | Asp | Ile | Pro | Ala | Gln | Val | Gln | Trp | Ser | |
| | 210 | | | | | 215 | | | | | 220 | | | | | |
| AGA | CCA | AGA | AGG | GGA | GAC | GTG | TTG | TAACAGAGTA | | ATCATGTAAT | | ATTGTATGTA | | | | 726 |

```
Arg Pro Arg Arg Gly Asp Val Leu
225             230
```

| | | | | | |
|---|---|---|---|---|---|
| AGGTTATGTA | TGTTCGTATG | GTATGGAAAA | AAAAAAAAAA | AAAGGATGCT | ATGTGGAGAA | 786 |
| TGTAAGGCGT | GGTAGCTCCG | GATAATTCAG | TCTGTAGGCT | TCATCACGGG | CAGTGGCCTG | 846 |
| ACTCTGAGAG | CTTGCTCCGG | TATTAAGTTG | TGCGTTTGAA | ATTTCTGGA | AAAAAGAAAT | 906 |
| TGATTGGTTG | AAGCTATACT | CGTCGAAAGA | TTTCTTCGGC | AGTGGTTGTT | GCTCCACCTG | 966 |
| CACGGGAGTT | GTGTTTGCGT | TTATGTTCGG | CTTGGCTATA | TTATTAGCGA | GTGATGTTTG | 1026 |
| CAATTTGCTG | TATTGAGAAT | CAATTTGGGT | GCGTAAGCTT | TCAATAATTT | TGCAGACCGC | 1086 |
| AGGCACTTCC | AACTTTATGA | GTTGCAGGTA | TTCTCTTTTA | TGAATATACG | ATGACGACGA | 1146 |
| TGACGACGAC | GCATCCATGC | GCAAAAGCTC | AGGGTGTCTA | GATAGTTTGT | TAGTCAATAA | 1206 |
| ATCCACATAT | CTAAAATAAT | AAATAAACGA | CAGCGACAAG | TCGTTGGCCT | GGAACGCACA | 1266 |
| CTGTGCCTTT | TCCAATATGC | CGATGCATGT | TTTCAGGTAA | ATTCTCAATG | GTATCGCCGG | 1326 |
| ATTGAAGCGA | TAATCCTTAG | CGTCCTGAAC | CAATTGCTTA | CTAGACTTCA | TGACCTACCG | 1386 |
| GGGCCAGATA | AAGATGCGGA | AGGAAGAGAA | AAAATGTATA | GTGGTTGGTG | AACCGCAACA | 1446 |
| ATAATTCGTG | CCAACACTTT | AATCGAAGCA | AAAATTGTCT | TGTATGTTAT | TAATATTATC | 1506 |
| TATCTAACCA | TTGATTTACG | TATAAAACTG | TCGATGCTCA | TCGCCTAGCA | ATGAAAAAAT | 1566 |
| TTTTTCTTTT | TTTTTCATT | ATTTCTCTTT | GTTGCGTACT | TTTTTCATT | GCGTTCGCG | 1626 |
| GCAAAAGCGA | TTCGAGTTGA | CTGGAAGTGT | GTTATACTAT | AAAAAGTGTA | TATGCCTATT | 1686 |
| TTTGGTTCTG | ATCTTTACTT | TACTGTTAAG | TACTGGCTGA | GGCAGTAGAC | TCTGCCTCTG | 1746 |
| TTACGGCAGC | GGTATTCGCC | TCGGCATCAG | CAGCCGCCCA | CGGTAGAGTA | GGTTCTGTTG | 1806 |
| TTTTGACGTT | TGCCAAGGTA | CTGTCCAAAT | GCTCCTTCAG | CAAGGCCTCA | TTACTTTCCT | 1866 |
| TCTCCGGACC | CACCGATTGC | GTGATCTCCT | GTACACGGTT | CAAGAACTTG | TTCAAATTGT | 1926 |
| AGCCCGCAGC | AGCATCAGAG | ACTTCTTGTG | TGTAAGGGAC | ACCCCTCAAC | TCCTTGACTC | 1986 |
| TTCTTTTGTG | CACTTTGCCC | TTTAAATGCG | TTTTTAACGC | TATAGCAGTC | TCCATGTATT | 2046 |
| TGGCACAGTG | TATGCAATAG | TGCTGACCAA | GGCCCGGTTT | GGTTTCATCC | AATGGCTGGT | 2106 |
| TCAGAAGCTT | CTGTACTGAT | TCCTTGGTGG | ACAAATCGTT | ATAGATCAGG | TCCAAGTCTC | 2166 |
| GTGTTCTTCT | TTTAGTCTTG | TATCTCTTCA | CCGAATATCT | ACCCATGATG | CGCTATTGTT | 2226 |
| TTATCTTCAC | TTGTCTGTGT | GTTAACTGC | CTTTCAATTC | ACCTCATCTC | ATCTCCCGCT | 2286 |
| ACTTTCCATA | TATAAAAGCA | AAATTAATTT | GCTTTTTCCC | CTGTCAGTAT | AAAAAAATTT | 2346 |
| TCCGCAGGAT | ATAGAAAAAA | AAGAAATGAA | ATTATAGTAG | CGGTTATTTC | CGTGGGGTGC | 2406 |
| TTTTTTACAC | CTGTACATCT | TTTCCCTCCG | TACATTTTT | TTATTTTTTT | TTGGGTTTT | 2466 |
| TTTTTTTCGA | TATTTTTCCC | TCCGAAACTA | GTTAGCACAA | TAATGCTGAC | TAAGGAAACT | 2526 |
| TTTCATCTCA | GAATTGATGG | TCAGTTTGGT | TTCTCTAGAG | AATAGTTTAT | AAAAAGATGT | 2586 |
| TGATGTGGAG | CAACCATTTA | TACATCCTTT | CCGCAAGTGC | TTTTGGAGTG | GGACTTTCAA | 2646 |
| ACTTTAAAGT | ACAGTATATC | AAATAACTAA | TTCAAGATGG | CTAGAAGACC | AGCTAGATGT | 2706 |
| TACAGATACC | AAAAGAACAA | GCCTTACCCA | AAGTCTAGAT | ACAACAGAGC | TGTTCCAGAC | 2766 |
| TCCAAGATCA | GAATCTACGA | TTTGGGTAAG | AAGAAGGCTA | CCGTCGAT | | 2814 |

( 2 ) INFORMATION FOR SEQ ID NO:7:

( i ) SEQUENCE CHARACTERISTICS:
        ( A ) LENGTH: 232 amino acids
        ( B ) TYPE: amino acid
        ( D ) TOPOLOGY: linear (ii) MOLECULE TYPE: protein (xi) SEQUENCE DESCRIPTION: SEQ ID NO:7:

```
Glu Phe Gln Tyr Thr Lys Gln Leu His Phe Pro Val Gly Pro Lys Ser
 1               5                  10                  15

Thr Asn Cys Glu Val Ala Glu Ile Leu Leu His Cys Asp Trp Glu Arg
             20                  25                  30

Tyr Ile Asn Val Leu Ser Ile Thr Arg Thr Pro Asn Val Pro Ser Gly
         35                  40                  45

Thr Ser Phe Ser Thr Arg Thr Arg Tyr Met Phe Arg Trp Asp Asp Gln
     50                  55                  60

Gly Gln Gly Cys Ile Leu Lys Ile Ser Phe Trp Val Asp Trp Asn Ala
 65                  70                  75                  80

Ser Ser Trp Ile Lys Pro Met Val Glu Ser Asn Cys Lys Asn Gly Gln
                 85                  90                  95

Ile Ser Ala Thr Lys Asp Leu Val Lys Leu Val Glu Glu Phe Val Glu
             100                 105                 110

Lys Tyr Val Glu Leu Ser Lys Glu Lys Ala Asp Thr Leu Lys Pro Leu
         115                 120                 125

Pro Ser Val Thr Ser Phe Gly Ser Pro Arg Lys Val Ala Ala Pro Glu
     130                 135                 140

Leu Ser Met Val Gln Pro Glu Ser Lys Pro Glu Ala Glu Ala Glu Ile
145                 150                 155                 160

Ser Glu Ile Gly Ser Asp Arg Trp Arg Phe Asn Trp Val Asn Ile Ile
                 165                 170                 175

Ile Leu Val Leu Leu Val Leu Asn Leu Leu Tyr Leu Met Lys Leu Asn
             180                 185                 190

Lys Lys Met Asp Lys Leu Thr Asn Leu Met Thr His Lys Asp Glu Val
         195                 200                 205

Val Ala His Ala Thr Leu Leu Asp Ile Pro Ala Gln Val Gln Trp Ser
     210                 215                 220

Arg Pro Arg Arg Gly Asp Val Leu
225                 230
```

(2) INFORMATION FOR SEQ ID NO:8:

(i) SEQUENCE CHARACTERISTICS:
(A) LENGTH: 1485 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:8:

```
ATGGACTTAA GAGTAGGAAG GAAATTTCGT ATTGGCAGGA AGATTGGGAG TGGTTCCTTT      60
GGTGACATTT ACCACGGCAC GAACTTAATT AGTGGTGAAG AAGTAGCCAT CAAGCTGGAA     120
TCGATCAGGT CCAGACATCC TCAATTGGAC TATGAGTCCC GCGTCTACAG ATACTTAAGC     180
GGTGGTGTGG GAATCCCGTT CATCAGATGG TTTGGCAGAG AGGGTGAATA TAATGCTATG     240
GTCATCGATC TTCTAGGCCC ATCTTTGGAA GATTTATTCA ACTACTGTCA CAGAAGGTTC     300
TCCTTTAAGA CGGTTATCAT GCTGGCTTTG CAAATGTTTT GCCGTATTCA GTATATACAT     360
GGAAGGTCGT TCATTCATAG AGATATCAAA CCAGACAACT TTTTAATGGG GGTAGGACGC     420
CGTGGTAGCA CCGTTCATGT TATTGATTTC GGTCTATCAA AGAAATACCG AGATTTCAAC     480
ACACATCGTC ATATTCCTTA CAGGGAGAAC AAGTCCTTGA CAGGTACAGC TCGTTATGCA     540
```

-continued

```
AGTGTCAATA CGCATCTTGG AATAGAGCAA AGTAGAAGAG ATGACTTAGA ATCACTAGGT      600
TATGTCTTGA TCTATTTTTG TAAGGGTTCT TTGCCATGGC AGGGTTTGAA AGCAACCACC      660
AAGAAACAAA AGTATGATCG TATCATGGAA AAGAAATTAA ACGTTAGCGT GGAAACTCTA      720
TGTTCAGGTT TACCATTAGA GTTCAAGAA TATATGGCTT ACTGTAAGAA TTTGAAATTC       780
GATGAGAAGC CAGATTATTT GTTCTTGGCA AGGCTGTTTA AAGATCTGAG TATTAAACTA      840
GAGTATCACA ACGACCACTT GTTCGATTGG ACAATGTTGC GTTACACAAA GGCGATGGTG      900
GAGAAGCAAA GGGACCTCCT CATCGAAAAA GGTGATTTGA ACGCAAATAG CAATGCAGCA      960
AGTGCAAGTA ACAGCACAGA CAACAAGTCT GAAACTTTCA ACAAGATTAA ACTGTTAGCC     1020
ATGAAGAAAT TCCCCACCCA TTTCCACTAT TACAAGAATG AAGACAAACA TAATCCTTCA     1080
CCAGAAGAGA TCAAACAACA AACTATCTTG AATAATAATG CAGCCTCTTC TTTACCAGAG     1140
GAATTATTGA ACGCACTAGA TAAAGGTATG GAAAACTTGA GACAACAGCA GCCGCAGCAG     1200
CAGGTCCAAA GTTCGCAGCC ACAACCACAG CCCCAACAGC TACAGCAGCA ACCAAATGGC     1260
CAAAGACCAA ATTATTATCC TGAACCGTTA CTACAGCAGC AACAAAGAGA TTCTCAGGAG     1320
CAACAGCAGC AAGTTCCGAT GGCTACAACC AGGGCTACTC AGTATCCCCC ACAAATAAAC     1380
AGCAATAATT TTAATACTAA TCAAGCATCT GTACCTCCAC AAATGAGATC TAATCCACAA     1440
CAGCCGCCTC AAGATAAACC AGCTGGCCAG TCAATTTGGT TGTAA                    1485
```

( 2 ) INFORMATION FOR SEQ ID NO:9:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

```
CCTACTCTTA GGCCCGGGTC TTTTTAATGT ATCC                                   34
```

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

```
GGAATCACTA CAGGGATG                                                     18
```

( 2 ) INFORMATION FOR SEQ ID NO:11:

( i ) SEQUENCE CHARACTERISTICS:
        ( A ) LENGTH: 543 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
GATCTCTGAA TTGAAGAACC GTTCAAACAT TGGCGAGCCC TTAACCAAAT CTTCCAATGA       60
AAGTACTTAT AAAGACATTA AAGCCACCGG CAATGATGGT GATCCGAATT TGGCTCTAAT      120
```

```
GAGAGCGGAG AATCGAGTAT TAAAATATAA ACTAGAGAAT TGTGAAAAAC TACTAGATAA    180

AGATGTGGTT GATTTGCAAG ATTCTGAGAT TATGGAAATT GTAGAAATGC TTCCCTTTGA    240

GGTCGGCACC CTTTTGGAAA CAAAGTTCCA AGGTTTGGAA TCACAAATAA GGCAATATAG    300

GAAATACACT CAAAAACTTG AAGACAAGAT CATGGCGCTA GAAAAAGTG GTCATACTGC     360

AATGTCGCTA ACTGGGTGTG ACGGACTGA AGTGATCGAA TTACAGAAGA TGCTCGAGAG     420

GAAGGATAAA ATGATTGAGG CCCTGCAGAG TGCCAAACGA CTGCGGGATA GGGCTTTGAA    480

ACCACTCATT AATACACAGC AATCACCGCA CCCTGTCGTG GATAACGATA AATGATTAGG    540

TGA                                                                  543
```

( 2 ) INFORMATION FOR SEQ ID NO:12:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

```
CCTTCCTACT CTTAAGCCCG GGCCGCAGGA ATTCG                                35
```

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

```
AGCAATATAG GATCCTTACA ACCAAATTGA                                      30
```

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

```
CCTACTCTTA AGCCCGGGTC TTTTAATGT ATCC                                  34
```

( 2 ) INFORMATION FOR SEQ ID NO:15:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

```
GTCTCAAGTT TTGGGATCCT TAATCTAGTG CG                                   32
```

( 2 ) INFORMATION FOR SEQ ID NO:16:

( i ) SEQUENCE CHARACTERISTICS:

( A ) LENGTH: 32 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:16:

| | | | |
|---|---|---|---|
| CACCATCGCC | CCCGGGTAAC | GCAACATTGT | CC | 32 |

( 2 ) INFORMATION FOR SEQ ID NO:17:

( i ) SEQUENCE CHARACTERISTICS:
( A ) LENGTH: 3628 base pairs
( B ) TYPE: nucleic acid
( C ) STRANDEDNESS: single
( D ) TOPOLOGY: linear ( i i ) MOLECULE TYPE: protein ( x i ) SEQUENCE DESCRIPTION: SEQ ID NO:17:

| | | | | | |
|---|---|---|---|---|---|
| GATCAGATGA | TATAGCTTTT | TGTGTGCCGT | ACCTTTCCGC | GATTCTGCCC | GTATATCTTG | 60 |
| GTCCCTGAGC | TATTTTCTGA | GATTCTTTTT | GTTGCTTTGC | CAAATCATTG | GCGTCATTCA | 120 |
| TGGTCATACC | AAATCCCAAT | TTGGCAAACT | TGGGTGTTAA | AGTATCTTGC | TGTTCTTTTC | 180 |
| TAGTTGTGTC | GAAGCTGTTT | GAAGTGTCAT | TTAAAAAATC | ATTGAATTCA | TCAGGCTGGG | 240 |
| TATTAATATC | ATCTATACTG | TTATTATTGT | TGCCTTTACT | GTTATTCATA | AATTGGGAAT | 300 |
| CGTAATCATT | TGTCTAATTT | TGGTGCTAGA | AGACGAATTA | GTGAACTCGT | CCTCCTTTTC | 360 |
| TTGTTGAGCC | TCTTTTTTAA | ATTGATCAAA | CAAGTCTTCT | GCCTGTGATT | TGTCGACTTT | 420 |
| CTTTGCGGTT | AGTCTAGTGG | GCTTTCTTGA | CGAAGACAAA | ATTGAATGTT | TCTTTTTATC | 480 |
| TTGCGAGTTT | AATACCGGTT | TCTTTCTGCA | TGCCGTTAAG | ATGGAACTTC | TCGTTTTAGT | 540 |
| GACAGTGGTC | TTGGGTGTGC | TGCCTGTGGT | GTTGTTTTTT | GGGGCGAGAG | AGCCTGTATT | 600 |
| TACATTGAGT | TTAGAACTGG | AATTGGAGCT | TGGTTTTGC | CAATTAGAGA | AAAAATCGTC | 660 |
| AACACTATTT | TCTTTGGAAG | TCGACCTGGA | AGCGTCTGAA | TCGGTGTCCA | ACGGTGAGTC | 720 |
| CGAAGAATCT | TGACCGTTCA | AGACTAATTC | TGATGGGTAT | AACTCCATAT | CCTTTTGAAC | 780 |
| CTTCTTGTCG | AGATGTATCT | TATATTTCTT | AGCAACAGGG | CTCGTATATT | TTGTTTTCGC | 840 |
| GTCAACATTT | GCTGTATTTA | GTAGCTGTTT | CCCATTGTTC | TTTAAGAAAA | AATCACGAGC | 900 |
| CTTATGGTTC | CCACCCAACT | TAAACCTTCT | TAAATTGTTA | ATTGTCCATT | TATCTAATGT | 960 |
| AGAAGACTTT | ACAAAGGTGA | TATGAACACC | CATGTTTCTA | TGCACAGCAG | AGCATTGAAT | 1020 |
| ACACAGCATC | ACACCAAAAG | GTACCGAAGT | CCAGTAGGAT | TCTTGTTACC | ACAATCAAAA | 1080 |
| CAAACTCGAT | TTTCCATGTT | GCTACCTAGC | TTCTGAAAAA | CTTGTTGAGT | AGTCTGTTCC | 1140 |
| GTGGCAAATG | TTTCTCCTTC | ATCGTTACTC | ATTGTCGCTA | TGTGTATACT | AAATTGCTCA | 1200 |
| AGAAGACCGG | ATCAACAAGT | ACTTAACAAA | TACCCTTTCT | TTGCTATCGC | CTTGATCTCC | 1260 |
| TTTTATAAAA | TGCCAGCTAA | ATCGTGTTTA | CGAAGAATAG | TTGTTTTCTT | TTTTTTTTT | 1320 |
| TTTTTTCGAA | ACTTTACCGT | GTCGTCGAAA | ATGACCAAAC | GATGTTACTT | TTCCTTTTGT | 1380 |
| GTCATAGATA | ATACCAATAT | TGAAAGTAAA | ATTTTAAACA | TTCTATAGGT | GAATTGAAAA | 1440 |
| GGGCAGCTTA | GAGAGTAACA | GGGGAACAGC | ATTCGTAACA | TCTAGGTACT | GGTATTATTT | 1500 |
| GCTGTTTTTT | AAAAAGAAG | GAAATCCGTT | TTGCAAGAAT | TGTCTGCTAT | TTAAGGGTAT | 1560 |
| ACGTGCTACG | GTCCACTAAT | CAAAAGTGGT | ATCTCATTCT | GAAGAAAAAG | TGTAAAAAGG | 1620 |
| ACGATAAGGA | AAGATGTCCC | AACGATCTTC | ACAACACATT | GTAGGTATTC | ATTATGCTGT | 1680 |

-continued

| | | | | | |
|---|---|---|---|---|---|
| AGGACCTAAG | ATTGGCGAAG | GGTCTTTCGG | AGTAATATTT | GAGGGAGAGA | ACATTCTTCA | 1740 |
| TTCTTGTCAA | GCGCAGACCG | GTAGCAAGAG | GGACTCTAGT | ATAATAATGG | CGAACGAGCC | 1800 |
| AGTCGCAATT | AAATTCGAAC | CGCGACATTC | GGACGCACCC | CAGTTGCGTG | ACGAATTTAG | 1860 |
| AGCCTATAGG | ATATTGAATG | GCTGCGTTGG | AATTCCCCAT | GCTTATTATT | TTGGTCAAGA | 1920 |
| AGGTATGCAC | AACATCTTGA | TTATCGATTT | ACTAGGGCCA | TCATTGGAAG | ATCTCTTTGA | 1980 |
| GTGGTGTGGT | AGAAAATTTT | CAGTGAAAAC | AACCTGTATG | GTTGCCAAGC | AAATGATTGA | 2040 |
| TAGAGTTAGA | GCAATTCATG | ATCACGACTT | AATCTATCGC | GATATTAAAC | CCGATAACTT | 2100 |
| TTTAATTTCT | CAATATCAAA | GAATTTCACC | TGAAGGAAAA | GTCATTAAAT | CATGTGCCTC | 2160 |
| CTCTTCTAAT | AATGATCCCA | ATTAATATA | CATGGTTGAC | TTTGGTATGG | CAAAACAATA | 2220 |
| TAGAGATCCA | AGAACGAAAC | AACATATACC | ATACCGTGAA | CGAAAATCAT | TGAGCGGTAC | 2280 |
| CGCCAGATAT | ATGTCTATTA | ATACTCATTT | TGGAAGAGAA | CAGTCACGTA | GGGATGATTT | 2340 |
| AGAATCGCTA | GGTCACGTTT | TTTTTATTT | CTTGAGGGGA | TCCTTGCCAT | GGCAAGGTTT | 2400 |
| GAAAGCACCA | AACAACAAAC | TGAAGTATGA | AAAGATTGGT | ATGACTAAAC | AGAAATTGAA | 2460 |
| TCCTGATGAT | CTTTTATTGA | ATAATGCTAT | TCCTTATCAG | TTTGCCACAT | ATTTAAAATA | 2520 |
| TGCACGTTCC | TTGAAGTTCG | ACGAAGATCC | GGATTATGAC | TATTTAATCT | CGTTAATGGA | 2580 |
| TGACGCTTTG | AGATTAAACG | ACTTAAAGGA | TGATGGACAC | TATGACTGGA | TGGATTTGAA | 2640 |
| TGGTGGTAAA | GGCTGGAATA | TCAAGATTAA | TAGAAGAGCT | AACTTGCATG | GTTACGGAAA | 2700 |
| TCCAAATCCA | AGAGTCAATG | GCAATACTGC | AAGAAACAAT | GTGAATACGA | ATTCAAAGAC | 2760 |
| ACGAAATACA | ACGCCAGTTG | CGACACCTAA | GCAACAAGCT | CAAAACAGTT | ATAACAAGGA | 2820 |
| CAATTCGAAA | TCCAGAATTT | CTTCGAACCC | GCAGAGCTTT | ACTAAACAAC | AACACGTCTT | 2880 |
| GAAAAAAATC | GAACCCAATA | GTAAATATAT | TCCTGAAACA | CATTCAAATC | TTCAACGGCC | 2940 |
| AATTAAAAGT | CAAAGTCAAA | CGTACGACTC | CATCAGTCAT | ACACAAAATT | CACCATTTGT | 3000 |
| ACCATATTCA | AGTTCTAAAG | CTAACCCTAA | AAGAAGTAAT | AATGAGCACA | ACTTACCAAA | 3060 |
| CCACTACACA | AACCTTGCAA | ATAAGAATAT | CAATTATCAA | AGTCAACGAA | ATTACGAACA | 3120 |
| AGAAAATGAT | GCTTATTCTG | ATGACGAGAA | TGATACATTT | TGTTCTAAAA | TATACAAATA | 3180 |
| TTGTTGTTGC | TGTTTTTGTT | GCTGTTGATA | AAGCGATTTT | TATACTTTTC | TCTTTTTCCT | 3240 |
| TTTTTTTTT | GATTGGCTGT | TTCCTTATGC | CGCTCTTTCC | CAATTATGA | CTTCCAATA | 3300 |
| ATGTATTATT | TTGTTTCTCT | TTCTCTCTGT | TACCCTTTAT | TTTATCATCT | ACAATAATTG | 3360 |
| AATTCGGAG | AGGGTAAAGA | AACAGGAAAA | AGAAGAAAAT | GAGACATAGT | CAGCATCGTA | 3420 |
| ATCGTTTTCC | TTCTGTATAT | TCCTTTATCA | AAAGACTACA | CGCACATATA | TATTAATCCC | 3480 |
| GGTATGTTTT | TGGTGTGCTA | AATCTATCTT | CAAGCACTAT | TATAGCATTT | TTTAAGAAT | 3540 |
| ATCCAAAATA | ATATGTAATT | TATGATTAAT | CAAGGTTCAA | GAATTGGAGA | AACCGTGAGC | 3600 |
| GACTTCTTTG | ATACTTGGAT | GTAAGCTT | | | | 3628 |

( 2 ) INFORMATION FOR SEQ ID NO:18:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

TGAAGATCGT TGGCCCGGGT TTCCTTATCG TCC      33

( 2 ) INFORMATION FOR SEQ ID NO:19:

( i ) SEQUENCE CHARACTERISTICS:
        ( A ) LENGTH: 2468 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

```
AATATTTCAA GCTATACCAA GCATACAATC AACTCCAAGC TTCGAGCGGC CGCCAGTGTG      60
CTCTAAAGGA AAAAGCGAGT GCCTTTAGCC TTAAAAGCGT TATAATATTA TTATGGCTTT     120
GGACCTCCGG ATTGGGAACA AGTATCGCAT TGGTCGTAAA ATTGGCAGTG GATCTTTCGG     180
AGACATTTAT CTTGGGACTA ATGTCGTTTC TGGTGAAGAG GTCGCTATCA AGCTAGAATC     240
AACTCGTGCT AAACACCCTC AATTGGAGTA TGAATACAGA GTTTATCGCA TTTTGTCAGG     300
AGGGGTCGGA ATCCCGTTTG TTCGTTGGTT CGGTGTAGAA TGTGATTACA ACGCTATGGT     360
GATGGATTTA TTGGGTCCTT CGTTGGAAGA CTTGTTTAAT TTTTGCAATC GAAAGTTTTC     420
TTTGAAAACA GTTCTTCTCC TTGCGGACCA GCTCATTTCT CGAATTGAAT TCATTCATTC     480
AAAATCTTTT CTTCATCGTG ATATTAAGCC TGATAACTTT TAATGGGAA TAGGTAAAAG     540
AGGAAATCAA GTTAACATAA TTGATTTCGG ATTGGCTAAG AAGTATCGTG ATCACAAAAC     600
TCACCTGCAC ATTCCTTATC GCGAGAACAA GAATCTTACA GGTACTGCAC GCTATGCTAG     660
CATCAATACT CATTTAGGTA TTGAACAATC CCGCCGTGAT GACCTCGAAT CTTTAGGTTA     720
TGTGCTCGTC TACTTTTGTC GTGGTAGCCT GCCTTGGCAG GGATTGAAGG CTACCACGAA     780
AAAGCAAAAG TATGAAAAGA TTATGGAGAA GAAGATCTCT ACGCCTACAG AGGTCTTATG     840
TCGGGGATTC CCTCAGGAGT TCTCAATTTA TCTCAATTAC ACGAGATCTT ACGTTTCGA     900
TGACAAACCT GATTACGCCT ACCTTCGCAA GCTTTTCCGA GATCTTTTT GTCGGCAATC     960
TTATGAGTTT GACTATATGT TTGATTGGAC CTTGAAGAGA AAGACTCAAC AAGACCAACA    1020
ACATCAGCAG CAATTACAGC AACAACTGTC TGCAACTCCT CAAGCTATTA ATCCGCCGCC    1080
AGAGAGGTCT TCATTTAGAA ATTATCAAAA ACAAAACTTT GATGAAAAAG GCGGAGACAT    1140
TAATACAACC GTTCCTGTTA TAAATGATCC ATCTGCAACC GGAGCTCAAT ATATCAACAG    1200
ACCTAATTGA TTAGCCTTTC ATATTATTAT TATATAGCAT GGGCACATTA TTTTTATATT    1260
TTCTTCTCAT CTGGAGTCTT CCAATACTTG CCTTTTATCC TCCAGACGTC CTTTAATTTT    1320
GTTGATAGCG CAGGGCTTTT TCCTTGGGAT GGCGAAAGTT ACTTTGCTTA TAGTTTATTG    1380
AGGGTTCATA GCTTATTTGG CTGAAGATCT TGTGTTGACT TAAATTCTAT GCTAACCTCA    1440
TGATCATATC CTCATTATGG CAAGTTTTGG TGAAAAATTT TTTAATATTA GTACATTTGC    1500
TAATAATACA TTTGGTATTT GTTTTACTA CCTGTGAATC TATTCATACA TTATCATATA    1560
TGTTTCGAGC CAGGAACAGA AAAAGTGAG AGAATTTTCT GCAGAAATGA TCATAATTTT    1620
ATCTTCGCTT AACACGAATC CTGGTGACAG ATTATCGTGG TTTAAAGCCT TTTTTTTACG    1680
ACGCCATAAG CAAATTGGTT ACTTTTTTAT GTGTGATGAG CCTTGGGGTT TAATCTAATT    1740
AGAAGGCATT GCATTCATAT ACTTTTAATA ATATATTATC AGCTATTTGC TGCTTTTCTT    1800
TATAGATACC GTCTTTTCCA AGCTGAACTC ATTAATCAG CGTCGTTTAA CCTTAGGATG    1860
CTTAAGATGC GTTTAAATTC AATGACTTAA TGCTCGAGGG ATGAATGGTT TGTTTTAGTT    1920
CGTGTTCTGG GTGCATGATC TCGTGCTTGA CTGTTTTATT GAAGCGTTCA TTTCATGAAG    1980
```

| | | | | | |
|---|---|---|---|---|---|
| TGTCTTTCGA | TGTTGTTCAC | ACTTCTGTTT | GCTAAATATA | ATAAATATTT | TGCTTTTCAC | 2040
| TTTAGAGCAC | ACTGGCGGCC | GCTCGAAGCT | TTGGACTTCT | TCGCCATTGG | TCAAGTCTCC | 2100
| AATCAAGGTT | GTCGGCTTGT | CTACCTTGCC | AGAAATTTAC | GAAAAGATGG | AAAAGGGATC | 2160
| CAAATCGTTG | GTAGATACTT | GTTGACACTT | CTAAATAAGC | GAATTCTTA  | TGATTTATGA | 2220
| TTTTATTAT  | TAAATAAGTT | ATAAAAAAA  | TAAGGTATAC | AAATTTTAAA | GTGACTCTTA | 2280
| GGTTTTAAAA | CGAAAATTCT | TATTCTTGAG | TAACTCTTTC | CTGTAGGTCA | GGTTGCTTTC | 2340
| TCAGGTATAG | CATGAGGTCG | CTCTTATTGA | CCACACCTCT | ACCGGCATGC | CGAGCAAATG | 2400
| CCTGCAAATC | GCTCCCCATT | TCACCCAATT | GTAGATATGC | TAACTCCAGC | AATGAGCCGA | 2460
| TGAATCTC | | | | | | 2468

( 2 ) INFORMATION FOR SEQ ID NO:20:

( i ) SEQUENCE CHARACTERISTICS:
  ( A ) LENGTH: 34 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:20:

GGGTTATAAT ATTATCCCGG GTTTGGACCT CCGG    34

( 2 ) INFORMATION FOR SEQ ID NO:21:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:21:

TCCCTCTCTA GATATGGCGA GATAGTTA    28

( 2 ) INFORMATION FOR SEQ ID NO:22:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:22:

GTTTACACTC GAGGCATATA GTGATACA    28

( 2 ) INFORMATION FOR SEQ ID NO:23:

( i ) SEQUENCE CHARACTERISTICS:
  ( A ) LENGTH: 5093 base pairs
  ( B ) TYPE: nucleic acid
  ( C ) STRANDEDNESS: single
  ( D ) TOPOLOGY: linear ( i i ) MOLECULE TYPE: protein ( x i ) SEQUENCE DESCRIPTION: SEQ ID NO:23:

| | | | | | |
|---|---|---|---|---|---|
| GCTAGCTTTT | GCCGGGGAAC | CCATCCCGAA | AAAATTGCAA | AAAAAAAAT | AGCCGCCGAC | 60
| CGTTGGTCGC | TATTCACGGA | ATGATAGAAA | AATAGCCGCG | CTGCTCGTCC | TGGGTGACCT | 120

| | | | | | |
|---|---|---|---|---|---|
| TTTGTATATT | GTATAAAGAT | AAACATAGTG | CTATCAGGAA | TATCTTTATA | TACACACGCA | 180 |
| TACTGAATGT | GGTTGAAGTT | CAAAAATAT | CACAAACGTT | AAGAAGTTTT | ACTGGTAAAC | 240 |
| ATATAGACAT | AGTGGAGCGC | TTGCTCGAGG | TCAAATGCAG | ACGGATACGA | GAGCGCGGGA | 300 |
| GGGAAACCGG | AGAAGGTCAA | TATGCCCATA | ATTCTTCTTC | TTTGAGGTTG | GCAATTATAT | 360 |
| ATTGTATCTG | AATTAGGCAA | ATAGAAAGA | GACCTTACCA | TTAGCGCCAT | CGTAGAGTCC | 420 |
| CATTTCACCT | TTTCTTAGTT | CTTTATATAT | GTCTGCGTAT | GGCCCACATA | TGCGCGCACA | 480 |
| GTGCGCGCCA | CCCTCTAAGA | ACGATAAACA | TAAATAAAC | ACATAAACAA | TCAACGACAG | 540 |
| TTCGCGCTTC | CCTCACTAAA | TATGGCGAGA | TAGTTAAACA | ATCATGGCTC | GTTCTTCCTT | 600 |
| GCCCAACCGC | CGCACCGCCC | AGTTCGAAGC | GAACAAGAGG | AGGACCATTG | CACATGCTCC | 660 |
| ATCTCCAAGT | CTTTCAAATG | GGATGCACAC | TCTAACGCCG | CCCACCTGTA | ACAATGGTGC | 720 |
| TGCCACTTCA | GACTCCAATA | TACATGTATA | TGTAAGGTGC | AGATCGCGTA | ATAAGCGAGA | 780 |
| AATAGAGGAA | AAAAGTAGTG | TAGTTATATC | TACACTAGGC | CCACAAGGGA | AAGAAATCAT | 840 |
| TCTGTCCAAC | GGTTCTCACC | AATCGTATTC | GTCCTCGAAG | AAAACTTACC | AATTTGATCA | 900 |
| GGTGTTCGGC | GCAGAATCTG | ACCAGGAAAC | AGTGTTTAAT | GCCACTGCAA | AAAACTACAT | 960 |
| TAAGGAAATG | TTGCACGGGT | ACAATTGTAC | AATATTTGCA | TACGGTCAAA | CGGGAACAGG | 1020 |
| TAAAACCTAC | ACTATGTCTG | GCGATATAAA | TATTCTCGGT | GATGTGCAAT | CTACCGATAA | 1080 |
| TCTATTATTA | GGAGAGCATG | CAGGTATCAT | ACCACGGGTT | CTGGTCGATT | TGTTTAAAGA | 1140 |
| ATTGAGCTCC | TTAAATAAAG | AGTACTCCGT | AAAAATATCC | TTTTAGAGT | TGTACAATGA | 1200 |
| AAATTTGAAA | GATCTGCTCT | CTGATAGTGA | GGACGATGAT | CCTGCAGTCA | ACGATCCCAA | 1260 |
| GAGGCAGATT | CGTATTTTTG | ACAATAACAA | CAATAATTCA | TCCATCATGG | TCAAGGGGAT | 1320 |
| GCAGGAAATC | TTTATTAACT | CTGCACACGA | AGGCTTGAAT | TTGCTAATGC | AGGGTTCGTT | 1380 |
| AAAAAGGAAA | GTGGCCGCTA | CTAAATGCAA | CGATCTTTCA | TCAAGGTCTC | ACACCGTCTT | 1440 |
| TACAATCACA | ACAAACATAG | TTGAGCAAGA | TAGCAAAGAC | CATGGACAAA | ACAAAAATTT | 1500 |
| TGTTAAAATT | GGCAAATTGA | ATTTGGTGGA | TTTGGCAGGC | AGTGAAAACA | TCAACAGATC | 1560 |
| GGGTGCGGAG | AATAAAAGGG | CTCAAGAAGC | TGGCCTAATA | AACAAATCGC | TGCTAACACT | 1620 |
| AGGCCGTGTT | ATCAACGCAC | TCGTTGATCA | TTCTAACCAT | ATACCTTACA | GAGAATCTAA | 1680 |
| GCTAACAAGA | TTGCTACAAG | ACTCTTTAGG | TGGTATGACG | AAAACATGCA | TTATCGCAAC | 1740 |
| TATATCACCT | GCGAAAATAT | CCATGGAAGA | GACTGCAAGT | ACGCTAGAAT | ATGCAACGAG | 1800 |
| AGCCAAATCA | ATTAAGAATA | CTCCACAAGT | AAATCAGTCT | TTATCGAAGG | ATACATGTCT | 1860 |
| CAAAGACTAC | ATTCAAGAGA | TTGAAAAATT | AAGAATGAT | TTGAAAAATT | CAAGAAACAA | 1920 |
| ACAAGGTATA | TTTATAACTC | AAGATCAGTT | GGACCTTTAC | GAGAGCAATT | CTATCTTGAT | 1980 |
| TGATGAGCAA | AATCTAAAAA | TACATAACCT | GCGAGAACAA | ATTAAAAAAT | TCAAAGAAAA | 2040 |
| CTACCTGAAC | CAATTAGATA | TCAATAATCT | TTTACAGTCT | GAAAAGGAAA | AACTAATTGC | 2100 |
| CATAATACAG | AATTTTAATG | TCGATTTTTC | TAACTTTTAC | TCGGAAATCC | AAAAAATTCA | 2160 |
| CCATACTAAT | CTCGAACTAA | TGAATGAAGT | CATACAACAG | AGAGATTTTT | CACTAGAAAA | 2220 |
| TTCTCAAAAA | CAGTATAATA | CGAACCAGAA | CATGCAATTA | AAATCTCTC | AACAAGTTTT | 2280 |
| ACAGACTTTG | AACACTTTAC | AGGGCTCTTT | AAATAATTAT | AACTCTAAAT | GTTCCGAAGT | 2340 |
| TATCAAAGGC | GTCACCGAAG | AACTAACCAG | GAACGTAAAT | ACCCATAAGG | CGAAACACGA | 2400 |
| TTCTACTCTC | AAATCGTTAT | TAAACATTAC | TACTAACTTA | TTGATGAATC | AGATGAACGA | 2460 |
| ACTGGTGCGT | AGTATTTCGA | CTTCATTGGA | AATATTTCAG | AGTGATTCTA | CTTCTCACTA | 2520 |

```
TCGTAAAGAT TTGAATGAAA TCTACCAATC ACATCAACAA TTTCTAAAAA ATTTACAAAA    2580
CGATATTAAA AGCTGTCTTG ATTCGATAGG CAGTTCAATT CTAACTTCCA TAAACGAAAT    2640
ATCGCAAAAT TGCACCACTA ACTTGAATAG TATGAATGTT TTAATAGAAA ACCAGCAGTC    2700
AGGATCATCG AAATTAATTA AAGAGCAAGA TTTAGAAATA AAAAAACTGA AAAACGATCT    2760
GATCAATGAG CGCAGGATTT CTAACCAATT CAACCAACAG TTGGCTGAAA TGAAGCGATA    2820
TTTTCAGGAT CACGTTTCCA GGACGCGTAG TGAATTCCAC GACGAACTTA ACAAATGTAT    2880
CGATAACCTA AAAGATAAAC AATCTAAGTT GGATCAAGAT ATCTGGCAGA AGACGGCCTC    2940
TATTTTCAAC GAAACAGATA TCGTAGTTAA TAAAATTCAT TCCGACTCAA TAGCATCCCT    3000
CGCTCATAAT GCTGAAAACA CTTGAAAAC GGTTTCTCAG AACAATGAAA GCTTACTAA     3060
CGATTTAATC AGTCTATCAC GCGGAATGAA CATGGACATA TCCTCCAAAC TGAGAAGTTT    3120
GCCCATCAAT GAATTTTTAA ACAAGATATC ACAAACCATT TGTGAAACCT GTGGCGATGA    3180
TAACACAATC GCATCAAATC CAGTATTGAC CTCTATTAAA AAATTTCAAA ATATAATTTG    3240
TTCAGACATT GCCCTAACAA ATGAGAAGAT CATGTCATTA ATAGATGAAA TACAATCACA    3300
AATTGAAACC ATATCTAATG AAAACAATAT CAATTTGATT GCAATAAATG AAAATTTTAA    3360
TTCTTTGTGC AATTTTATAT TAACTGATTA CGATGAGAAT ATTATGCAAA TCTCAAAAAC    3420
ACAAGATGAG GTGCTTTCTG AACATTGCGA GAAGCTACAA TCACTGAAAA TACTGGGTAT    3480
GGACATTTTC ACTGCTCACA GCATAGAAAA ACCCCTTCAT GAGCATACAA GACCTGAAGC    3540
GTCAGTAATC AAGGCTTTAC CCTTATTGGA TTATCCAAAA CAATTTCAGA TTTATAGGGA    3600
TGCTGAAAAT AAGAGCAAAG ACGACACATC TAATTCTCGT ACTTGTATAC CAAACTTGTC    3660
AACTAATGAA AATTTTCCTC TTTCACAATT CAGTCCAAAA ACCCCAGTGC CAGTGCCTGA    3720
TCAACCTCTA CCAAAAGTTC TTATACCGAA AAGCATAAAC TCGGCCAAGT CCAATAGATC    3780
AAAGACCTTA CCAAATACAG AGGGTACTGG ACGAGAATCG CAGAACAATT GAAGAGAAG    3840
ATTTACCACC GAGCCAATAT TGAAGGGAGA AGAAACTGAA AATAATGACA TACTGCAAAA    3900
TAAAAAACTT CATCAATAAG GGGATATAGC CATTGTAAAA TATTTGTATC ACTATATGCA    3960
TTGAGTGTAA ACTGTTGCAC CTATAAAGAA TGAAAACAAT CTAGTATGTG TACTTACATA    4020
ATTACACAGT CTTTTTTTTT TTTACCTTGT TTATCCTTCT TGTTCTTCAA GCTTGTAGGT    4080
TTTTTTGACT CAGTTTTTAC TGCAGGAAAA TCTTTACGAA TCATGTTTGA ACTGCCCATA    4140
TTTGATAAAC TAACTTCTTG CTTTGCTGCC ATCGACTGCT CAGCAACTTC CCTTGACATT    4200
CCCTTTGCTG AGGAAGAACT TTTCCTGATG CTTGTATCAG AACCCGTTTT AATACCATTT    4260
CTATTCGTGT TTGAATTCAT GTTAATTTGC AAACCTTGTG GCTCACGATC ACGTTTGGA    4320
TTTCCAGTAA AGAATGTTTC AGATTTGAA GAAACTCTTG AATTTGACCC TACGTTACTT    4380
GTTTGACTGT CCACAGTAGA GAATAAATTC AAAGTACTGA TACTTTATT TTTTTTATGC    4440
TGTTTTTAC CAATGCTGGC TAGTCCACCG TCCCTTGAGC GTAGCTTATT AATCGCCCTC    4500
TTGTCCTCGT TCCCTGCAGC TTTCTCGTAC CATTTCCATG CGTATTCCAT GTTACGATCA    4560
CAGCCCTTGC CATGCTCATA GAAGTAGCCC AGAGTGAATT GGGCCTTTGG CAAACCAGCA    4620
TTAGCTGCAC GCAAGGCCCA TTGAAAAGCC TCATTTTCAT CTTTTTCAAA AGCAGGTTCT    4680
GCTCCCAGTA AGTACCATGC ACATAAACCT AACATTGCCA CAGAATCGCC TTTTAACGCT    4740
GCCTGCGTAT AATAGTGTAC AGAAAGTGAT GTATCCTGCC CTACTGTATC ATTACCTGTT    4800
TCATAAATCT GTGCCAACAA AGTTGCTGAA GGAACATGCC CTAAACTTGC TGCTTGAATA    4860
TATAGTTCCA TTGCATACTT TCATCCGGA ATGACAACAT CTAAGAACCC TTCATGATAA    4920
```

| ATCTTAGCCA | ATTCGTATGG | TGCTGCGGCC | GTCAACTCAT | TAGCTCTTGC | TGCAGCCCTT | 4980 |
| GATAACCATT | TTACCCCATT | TAATTTAGTA | TTAACGTCGG | TTGGAAGACC | CATTCTGCCG | 5040 |
| TAGAATGAAT | AAAGTCCCAA | TTTATACATT | GCTGAGGGAT | GATTCCTGCT | AGC | 5093 |

( 2 ) INFORMATION FOR SEQ ID NO:24:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

| GATAGTTAAG | GATCCATGGC | TCGTTCTTCC | TTGCCCAACC | GC | | 42 |

( 2 ) INFORMATION FOR SEQ ID NO:25:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:25:

| AAACTTCATC | AATGCGGCCG | CTAAGGGGAT | CCAGCCATTG | TAAAT | | 45 |

( 2 ) INFORMATION FOR SEQ ID NO:26:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:26:

| TTTCCTTGTT | TATCCTTTTC | CAA | 23 |

( 2 ) INFORMATION FOR SEQ ID NO:27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:27:

| GATCACTTCG | GATCCGTCAC | ACCCAGTTAG | 30 |

( 2 ) INFORMATION FOR SEQ ID NO:28:

( i ) SEQUENCE CHARACTERISTICS:
        ( A ) LENGTH: 2870 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:28:

| AATTTCCTTG | TTTATCCTTT | TCCAATAGCG | GAACAATTGA | TAATAAAGCA | ATGTAAGCAG | 60 |

| | | | | | |
|---|---|---|---|---|---|
| AAGCGAAAAA | TAAAAAGAAA | TAGGCTGCAG | AGATTCACAG | GCTGCGCTCT | AGAAACATTT | 120 |
| GAAATCAAGG | CAAACATAGA | ACACTTGATA | AAATTCTTAC | CATAATACCA | CCATTGATGA | 180 |
| TTCAAAAAAT | GAGCCCAAGC | TTAAGGAGGC | CATCAACGAG | GTCTAGTTCT | GGTTCAAGTA | 240 |
| ATATCCCACA | ATCGCCCTCT | GTACGATCAA | CTTCATCGTT | TTCTAATCTG | ACAAGAAACT | 300 |
| CCATACGGAG | CACCTCTAAT | TCGGGTTCTC | AGTCGATTTC | TGCATCTTCC | ACTAGAAGTA | 360 |
| ACTCCCCACT | AAGATCCGTA | TCAGCCAAAT | CCGATCCCTT | CCTTCACCCA | GGTAGGATAA | 420 |
| GGATCAGGCG | GAGCGACAGT | ATTAACAACA | ACTCGAGAAA | AACGATACA | TATACTGGGT | 480 |
| CAATCACTGT | GACCATCCGG | CCGAAACCAC | GGAGCGTTGG | AACTTCCCGT | GACCATGTGG | 540 |
| GGCTAAAATC | GCCCAGGTAC | TCTCAACCAA | GATCCAACTC | ACATCACGGT | AGCAATACAT | 600 |
| TTGTTAGAGA | CCCCTGGTTT | ATTACTAATG | ACAAAACAAT | AGTGCATGAA | GAAATTGGAG | 660 |
| AGTTCAAGTT | CGATCATGTT | TTTGCTTCCC | ATTGCACTAA | TTTGGAAGTT | TATGAAAGAA | 720 |
| CCAGTAAACC | AATGATTGAT | AAGTTATTGA | TGGGGTTTAA | TGCCACCATA | TTTGCGTACG | 780 |
| GTATGACCGG | GTCAGGTAAA | ACGTTTACAA | TGAGCGGAAA | TGAACAAGAG | CTAGGCCTAA | 840 |
| TTCCTTTATC | TGTGTCGTAT | TTATTTACCA | ATATCATGGA | ACAATCAATG | AATGGCGATA | 900 |
| AAAAGTTCGA | CGTTATAATA | TCGTACCTCG | AAATTTACAA | TGAAAGGATT | TACGACCTGT | 960 |
| TAGAAAGCGG | ATTAGAAGAA | TCCGGTAGTA | GAATCAGTAC | TCCTTCAAGG | TTATATATGA | 1020 |
| GCAAGAGCAA | CAGCAATGGA | TTGGGCGTAG | AATTAAAAAT | CAGAGATGAC | TCTCAGTATG | 1080 |
| GGGTCAAAGT | TATCGGTCTC | ACCGAAAGAA | GATGTGAAAG | TAGTGAAGAA | TTATTGAGGT | 1140 |
| GGATTGCAGT | TGGTGACAAA | AGTAGGAAAA | TTGGCGAAAC | TGACTACAAT | GCAAGAAGCT | 1200 |
| CACGATCTCA | TGCCATTGTA | CTGATTCGTT | TAACAAGTAC | TAACGTAAAG | AACGGCACCT | 1260 |
| CAAGATCGAG | TACATTGTCG | TTGTGTGACC | TAGCAGGTTC | GGAAAGGGCT | ACGGGCAAC | 1320 |
| AAGAGAGGAG | AAAGGAAGGT | TCATTCATCA | ACAAATCCTT | ACTTGCTTTG | GGGACTGTGA | 1380 |
| TATCCAAACT | CAGTGCCGAC | AAGATGAACT | CAGTAGGCTC | AAACATTCCC | TCGCCATCTG | 1440 |
| CAAGTGGCAG | TAGCAGCAGT | AGTGGAAATG | CTACCAATAA | CGGCACTAGC | CAAGCAACC | 1500 |
| ACATTCCATA | TCGTGATTCT | AAATTGACTA | GATTATTGCA | GCCGGCACTA | AGCGGTGACA | 1560 |
| GCATAGTGAC | AACGATATGT | ACAGTCGACA | CCAGAAATGA | TGCGGCAGCG | GAAACTATGA | 1620 |
| ATACGCTGAG | GTTTGCATCA | AGAGCGAAAA | ACGTCGCACT | TCATGTATCC | AAAAAATCCA | 1680 |
| TCATCAGTAA | CGGGAATAAC | GATGGAGATA | AAGATCGCAC | CATTGAGCTA | CTGAGACGCC | 1740 |
| AATTGGAAGA | ACAACGTAGG | ATGATCTCTG | AATTGAAGAA | CCGTTCAAAC | ATTGGCGAGC | 1800 |
| CCTTAACCAA | ATCTTCCAAT | GAAAGTACTT | ATAAAGACAT | TAAAGCCACC | GGCAATGATG | 1860 |
| GTGATCCGAA | TTTGGCTCTA | ATGAGAGCGG | AGAATCGAGT | ATTAAAATAT | AAACTAGAGA | 1920 |
| ATTGTGAAAA | ACTACTAGAT | AAAGATGTGG | TTGATTTGCA | AGATTCTGAG | ATTATGGAAA | 1980 |
| TTGTAGAAAT | GCTTCCCTTT | GAGGTCGGCA | CCCTTTTGGA | AACAAAGTTC | CAAGGTTTGG | 2040 |
| AATCACAAAT | AAGGCAATAT | AGGAAATACA | CTCAAAAACT | TGAAGACAAG | ATCATGGCGC | 2100 |
| TAGAAAAAAG | TGGTCATACT | GCAATGTCGC | TAACTGGGTG | TGACGGCACT | GAAGTGATCG | 2160 |
| AATTACAGAA | GATGCTCGAG | AGGAAGGATA | AAATGATTGA | GGCCCTGCAG | AGTGCCAAAC | 2220 |
| GACTGCGGGA | TAGGGCTTTG | AAACCACTCA | TTAATACACA | GCAATCACCG | CACCCTGTCG | 2280 |
| TGGATAACGA | TAAATGATTA | GGTGAGGGTC | CCAGATCTCG | GGTGCTTTTT | TCCTTGTGCG | 2340 |
| GATTGTTCTG | TAGACTGCGC | CTCCGCTTCC | CGGCCTTGCT | TGAACGGGAT | CTATTCTCAG | 2400 |
| AAGACAGCGC | ATAAAAGGCA | GTTTTTAGGC | ACTTCTCGTT | AAGAAAATAC | ACAAATAATG | 2460 |

```
GATTTACAGT  TCGTTTCAGT  GTGGTACCAA  AAAATTTCAT  CAGCTAATAA  AGATCAAGAA      2520

GTTTTGGGGT  TGTTTCGAGT  CTGTCTCGGC  CTTAATTGTG  CAGGTACTAA  AGGAATTAAT      2580

ATATAAAGAT  TGTTAAGGCC  AAGTGACTGA  AACTTGCAAA  CGTCTTTGAA  TCAGGCTTAT      2640

CTCTTAAATA  CTTATATATA  TGTTCTTTTA  TAGACTTCAT  AATCTCTTGT  TCCAAGAACA      2700

GTAAAGAGCA  ATTAAAAAAA  GGAAAATAAC  AGTTAAAGAT  GATAGCGGAT  TCATCAGTTT      2760

TGAAAAAGCA  CACAGCAATC  AAGAGAAGTA  CGAGAATAAT  ATCGCTAACA  CTCGTTTTGC      2820

TTGGCGTATT  TAGCTTCTTA  CTACTTACAT  GGAATGACTC  CTTGGAATTC                  2870
```

( 2 ) INFORMATION FOR SEQ ID NO:29:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

```
ACCATAATAC  CAGGATCCAT  GATTCAAAAA                                            30
```

( 2 ) INFORMATION FOR SEQ ID NO:30:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

```
CCTGTCGTGG  ATAGCGGCCG  CTAGGATCCT  GAGGGTCCCA  GA                            42
```

( 2 ) INFORMATION FOR SEQ ID NO:31:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

```
ACATCATCTA  GAGACTTCCT  TTGTGACC                                              28
```

( 2 ) INFORMATION FOR SEQ ID NO:32:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

```
TATATAATCG  ATTGAAAGGC  AATATC                                                26
```

( 2 ) INFORMATION FOR SEQ ID NO:33:

( i ) SEQUENCE CHARACTERISTICS:
        ( A ) LENGTH: 3883 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:33:

```
AGCAAGAATT GAACATGGAT GAATTCATTG GATCAAAGAC CGATTTAATC AAAGATCAAG      60
TGAGAGATAT TCTTGATAAA TTGAATATTA TTTAATTCTT CATTTAGAAA AATTTCAGCT     120
GCTTTTTTTT TTCTTTTTCT TTCCTTAGGC GTCTCGAGGT TACAAGTCGG AGTCCCTCTT     180
CACTATCGTT TGTCCACTTT TTTTATATCC CCATTATTTT CAATCTGAAT TTCATTTTTT     240
TTTTTAATT CATGAAATTT ATATGTCCCA CGTATTACTA CATATTTGCG TTTTTAATTA      300
AATAAATAAC TGTTACTTTT ATTATATCTT ATTTGCAGAT CACTTATCTG ATCAAATGTT     360
TTCGTTTTCG TGTGTGGTGA CGATGTATTA GGTACGCGAA ATAAACAAAA CAAACAAACA     420
AGGCCGCAAC AATAACATCA TCTAAAGACT TCCTTTGTGA CCCGCTTCTC AACAGCGGGT     480
GTAGAACTTA TGGTATGGCC AGAAAGTAAC GTTGAGTATA GATACAGAAG CAAGCAATTC     540
AAAGGAAAAA GTAATAAAAA GTATATAAAA GCGCAAAAAA TACAACAAGA AAGAATTTGT     600
TTGATGCCAG CGGAAAACCA AAATACGGGT CAAGATAGAA GCTCCAACAG CATCAGTAAA     660
AATGGCAACT CTCAGGTTGG ATGTCACACT GTTCCTAATG AGGAACTGAA CATCACTGTA     720
GCTGTGCGAT GCAGAGGAAG GAATGAAAGG GAAATTAGTA TGAAAAGCTC CGTTGTGGTA     780
AATGTTCCAG ATATTACAGG TTCTAAAGAA ATTTCCATTA ACACGACGGG AGATACCGGT     840
ATAACTGCTC AAATGAATGC CAAGAGATAC ACAGTGGACA AAGTCTTCGG TCCCGGCGCT     900
TCCCAGGATC TAATTTTTGA TGAAGTGGCG GGCCCATTAT TCCAGGATTT CATTAAAGGT     960
TACAATTGCA CCGTACTGGT ATATGGTATG ACGTCAACAG GTAAACATA TACAATGACG      1020
GGCGACGAAA AGTTATATAA TGGTGAATTG AGCGATGCAG CAGGAATTAT ACCGAGGGTT     1080
CTTTTGAAGT TGTTTGACAC ATTGGAACTA CAACAGAACG ATTACGTAGT AAAATGTTCG     1140
TTCATTGAAC TCTACAACGA AGAATTGAAG GACCTCTTGG ACAGCAATAG CAACGGCTCT     1200
AGTAATACTG GCTTTGACGG CCAATTTATG AAAAAATTGA GGATTTTTGC TTCAAGCACA     1260
GCAAATAATA CCACTAGCAA CAGTGCTAGT AGTTCCAGGA GTAATTCTAG GAACAGTTCT     1320
CCGAGGTCAT TAAATGATCT AACACCTAAA GCTGCTCTAT TAAGAAAAAG GTTAAGGACA     1380
AAATCACTGC CGAATACCAT CAAGCAACAG TATCAACAAC AACAGGCAGT GAATTCCAGG     1440
AACAACTCTT CCTCTAACTC TGGCTCTACC ACTAATAATG CTTCTAGTAA CACCAACACA     1500
AATAACGGTC AAAGAAGTTC GATGGCTCCA AATGACCAAA CTAATGGTAT ATACATCCAG     1560
AATTTGCAAG AATTTCACAT AACAAATGCT ATGGAGGGGC TAAACCTATT ACAAAAAGGC     1620
TTAAAGCATA GGCAAGTAGC GTCCACTAAA ATGAACGATT TTTCCAGTAG ATCTCATACC     1680
ATTTTTACAA TCACTTTGTA TAAGAAGCAT CAGGATGAAC TATTTAGAAT TTCCAAAATG     1740
AATCTTGTGG ATTTAGCTGG TTCAGAAAAC ATCAACAGAT CCGGAGCATT AAATCAACGT     1800
GCCAAAGAAG CTGGTTCAAT CAACCAAAGT CTATTGACGC TGGGCAGGGT CATAAACGCA     1860
CTCGTAGATA AAAGCGGCCA TATACCTTTC CGTGAATCGA AATTGACCCG CCTGCTTCAA     1920
GATTCCCTGG GTGGTAATAC GAAAACCGCA CTAATTGCTA CTATATCGCC TGCAAAGGTA     1980
ACTTCTGAAG AAACCTGCAG TACATTAGAG TATGCTTCGA AGGCTAAAAA CATTAAGAAC     2040
AAGCCGCAAC TGGGTTCATT TATAATGAAG GATATTTTGG TTAAAAATAT AACTATGGAA     2100
TTAGCAAAGA TTAAATCCGA TTTACTCTCT ACAAAGTCCA AAGAAGGAAT ATATATGAGC     2160
```

-continued

| | | | | | |
|---|---|---|---|---|---|
| CAAGATCACT | ACAAAAATTT | GAACAGTGAT | TTAGAAAGTT | ATAAAAATGA | AGTTCAAGAA | 2220 |
| TGTAAAAGAG | AAATTGAAAG | TTTGACATCG | AAAAATGCAT | TGCTAGTAAA | AGATAAATTG | 2280 |
| AAGTCAAAAG | AAACTATTCA | ATCTCAAAAT | TGCCAAATAG | AATCATTGAA | AACTACCATA | 2340 |
| GATCATTTAA | GGGCACAACT | AGATAAACAG | CATAAAACTG | AAATTGAAAT | ATCCGATTTT | 2400 |
| AATAACAAAC | TACAGAAGTT | GACTGAGGTA | ATGCAAATGG | CCCTACATGA | TTACAAAAAA | 2460 |
| AGAGAACTTG | ACCTTAATCA | AAAGTTTGAA | ATGCATATTA | CTAAAGAAAT | TAAAAAATTG | 2520 |
| AAATCTACAC | TGTTTTTACA | ATTAAACACT | ATGCAACAGG | AAAGTATTCT | TCAAGAGACT | 2580 |
| AATATCCAAC | CAAATCTTGA | TATGATCAAA | AATGAAGTAC | TGACTCTTAT | GAGAACCATG | 2640 |
| CAAGAAAAAG | CTGAACTAAT | GTACAAAGAC | TGTGTGAAGA | AAATTTTAAA | CGAATCTCCT | 2700 |
| AAATTCTTCA | ATGTTGTTAT | TGAGAAAATC | GACATAATAA | GAGTAGATTT | CCAAAAATTT | 2760 |
| TATAAAAATA | TAGCCGAGAA | TCTTTCTGAT | ATTAGCGAAG | AAAATAACAA | CATGAAACAG | 2820 |
| TACTTAAAAA | ACCATTTTTT | CAAGAATAAC | CATCAAGAAT | TACTGAATCG | TCATGTGGAT | 2880 |
| TCTACTTATG | AAAATATTGA | GAAGAGAACA | AACGAGTTTG | TTGAGAACTT | TAAAAAGGTC | 2940 |
| CTAAATGACC | ACCTTGACGA | AAATAAAAAA | CTAATAATGC | ACAATCTGAC | AACTGCAACC | 3000 |
| AGCGCGGTTA | TTGATCAAGA | AATGGATCTG | TTTGAACCCA | AGCGCGTTAA | ATGGGAAAAT | 3060 |
| TCATTTGATC | TGATAAATGA | TTGTGACTCC | ATGAATAACG | AATTCTATAA | TAGCATGGCA | 3120 |
| GCGACGCTAT | CGCAAATCAA | GAGTACTGTT | GATACATCAT | CAAATTCGAT | GAATGAGTCT | 3180 |
| ATTTCAGTCA | TGAAGGACA | AGTGGAAGAA | TCGGAGAACG | CTATATCCCT | TTTGAAGAAC | 3240 |
| AATACCAAAT | TTAATGATCA | ATTTGAGCAG | CTTATTAACA | AGCATAACAT | GTTGAAAGAT | 3300 |
| AACATTAAAA | ATTCGATAAC | ATCAACACAC | TCTCATATAA | CTAATGTGGA | TGATATCTAT | 3360 |
| AATACGATTG | AAAACATAAT | GAAAAACTAT | GGTAACAAGG | AAAACGCTAC | CAAAGACGAA | 3420 |
| ATGATCGAGA | ACATATTGAA | GGAAATACCA | AATCTAAGTA | AGAAAATGCC | GTTAAGGTTA | 3480 |
| TCAAACATAA | ATAGCAATTC | AGTGCAAAGT | GTAATATCGC | CCAAAAAGCA | TGCAATTGAA | 3540 |
| GATGAAAACA | AATCCAGTGA | AAATGTGGAC | AATGAGGGCT | CGAGAAAAAT | GTTAAAGATT | 3600 |
| GAATAGTTGA | TATTGCCTTT | CAGTCGAATA | TATATTCAAA | CTAGTGGTTA | ATAAAAACAA | 3660 |
| AGTATGTAAA | GAATACTCAG | TTATTCATTA | GAAGGCAAGA | CAGAAGAGAA | GGGTGTGAAA | 3720 |
| CCACCTCTAC | CAAACACACC | AAGAGATGAA | CCTAAATCAA | ATTTTCACAG | AGCTAACTAT | 3780 |
| ATAAACGTTT | GGATTCGTGT | GTACTATCTT | TATTTACGGA | AATAAGTTGT | AATATTAAAA | 3840 |
| AAAAAAAAAA | ACATTTGAT | GGACAATGAA | TTTCTCTAAT | TTT | | 3883 |

( 2 ) INFORMATION FOR SEQ ID NO:34:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

CGGGTGTAGG ATCCATGGTA TGGCCAGAAA GTAACG                           36

( 2 ) INFORMATION FOR SEQ ID NO:35:

( i ) SEQUENCE CHARACTERISTICS:
        ( A ) LENGTH: 53 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO:35:

GTGGACAATG GCGGCCGCAG AAAAAGGATC CAGATTGAAT AGTTGATATT GCC  53

( 2 ) INFORMATION FOR SEQ ID NO:36:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

GAATATTCTA GAACAACTAT CAGGAGTC  28

( 2 ) INFORMATION FOR SEQ ID NO:37:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:37:

TTGTCACTCG AGTGAAAAAG ACCAG  25

( 2 ) INFORMATION FOR SEQ ID NO:38:

( i ) SEQUENCE CHARACTERISTICS:
        ( A ) LENGTH: 3466 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:38:

```
CTGCAGCAGA AAATCCAGTA GAACCATCAT CATGTTTGCT GTTTTTCGAT TTTTTCTTTC    60
TTGGGAAGTC GTCGTCCTCT TCTTCTTCAT CATCATCTTC TTCAGCATCA CTTTGTTCGT   120
TATCTATAAT TTAGATGAT  TCATCGCTAG AGCTATTCTG CTCGTCTTCT TCGGCTTCAT   180
CACCTTCCAT TATTGTATCT TTTTCCGGCT CATTACTTAA CTCTTGGTTG CCACTATTCC   240
TTTTTTCACG CCCAAATTCT GCATTCTTTC TGGTTCTTTT CTTATCCTTA GTGTCTACTC   300
TGTGCTTGGA GCCCATGATC AATTATGTAC TGATTTTCCT TCGGCTTCTC TATCGCTTTA   360
TTCATAGCAT CTGTTTATTA CCTTTCCTTA TATCTTATGG GCATCGAATC CTAGATTTTT   420
TTCTTTCAAA ATTTTCCAAT AAGAGGGTAA TGGAGATACA CCAAAATGAA TCTCAAACAA   480
AATCAAAACA ACACTGTTT ACAATTTGAT GCGCCTCGAA TCAAATATG ATGATGAGTA   540
TTACAGCTAA AAAAATTATC GAATATTATA TAAGCATTAA AGCTATCAAT TTTTCCGCTC   600
TTTGTGTTTC TTATTATTCT ATTTGAATAT ACCAGAACAA CTATCCGGAG TCTTTGTTTA   660
AAAAGGTAG ATTTGAAAT AAAGGACTTA GAGAAATTCT GGCAACTATT AAAGTATGGA   720
ATCACTTCCA CGTACTCCCA CAAAAGGCAG ATCTACGCAG CATCTCTCGA CACCATCGCC   780
GAAGAATGAT ATTTTAGCTA TGAATGGCCA CAAAAGAAGA AATACAACAA CTCCACCGCC   840
TAAGCACACT CTTCTGAAGC CGCAACGTAC GGATATTCAT AGACACTCAT TAGCTAGTCA   900
```

```
GAGTCGCATA TCCATGTCAC CTAATCGCGA GCTTTTAAAG AATTATAAAG GTACAGCAAA    960
TTTGATTTAT GGAAACCAGA AAAGCAACTC CGGTGTAACT TCCTTTTATA AAGAAAATGT   1020
TAATGAACTC AATAGAACAC AAGCAATCTT ATTTGAGAAA AAGGCAACAC TAGATTTACT   1080
CAAAGATGAA CTAACAGAAA CGAAAGAGAA AATCAATGCC GTTAATCTCA AATTTGAAAC   1140
CCTTCGTGAA GAAAAGATAA AAATTGAACA GCAACTGAAT TTGAAAAACA ATGAACTTAT   1200
CTCGATTAAA GAAGAATTTT TGTCAAAGAA GCAGTTCATG AATGAAGGAC ATGAAATACA   1260
TTTAAAGCAG CTAGCGGCAT CTAATAAAAA AGAGCTGAAA CAAATGGAAA ATGAATACAA   1320
AACAAAAATT GAGAAATTGA AATTTATGAA GATTAAACAG TTTGAAAATG AAAGAGCGTC   1380
GCTTTTAGAT AAAATAGAAG AGGTAAGAAA TAAAATCACC ATGAACCCTT CCACTTTACA   1440
GGAAATGTTG AACGATGTTG AACAAAAGCA TATGCTTGAA AAAGAAGAAT GGCTTACAGA   1500
GTACCAATCG CAGTGGAAAA AGGATATAGA GCTGAATAAT AAACATATGC AAGAAATCGA   1560
AAGCATAAAA AAGGAAATCG AAAATACATT AAAACCTGAG TTGGCAGAAA AAAAGAAGCT   1620
CTTAACAGAA AAGCGTAACG CGTATGAAGC TATCAAAGTA AAGTTAAAG AAAAGGAAGA    1680
GGAAACTACA AGGCTGAGAG ATGAGGTGGC ATTAAAACAG AAAACTAATT TAGAAACTTT   1740
GGAAAAGATC AAAGAACTTG AGGAATATAT AAAAGACACT GAACTGGGTA TGAAGGAGTT   1800
GAATGAAATT CTGATTAAAG AGGAAACGGT TAGACGCACA TTGCATAATG AGTTACAAGA   1860
GTTAAGAGGA AATATACGAG TTTATTGTAG GATTCGTCCA GCTCTAAAAA ATTTGGAAAA   1920
TTCTGATACT AGCCTTATTA ATGTTAATGA ATTTGATGAC AATAGTGGTG TTCAATCTAT   1980
GGAAGTGACG AAAATACAAA ACACAGCGCA AGTGCATGAA TTCAAATTTG ATAAAATATT   2040
TGATCAACAG GATACAAATG TGGATGTTTT TAAAGAAGTT GGTCAGTTAG TGCAAAGTTC   2100
ATTAGATGGA TATAATGTTT GTATCTTCGC ATACGGACAA ACAGGATCTG GGAAAACTTT   2160
CACGATGTTA AATCCAGGTG ATGGTATCAT TCCGTCCACA ATATCTCATA TATTTAACTG   2220
GATCAATAAA TTAAAGACAA AAGGATGGGA TTATAAAGTT AACTGCGAAT TCATTGAGAT   2280
CTACAACGAG AACATCGTAG ACTTATTGAG AAGTGATAAT AATAATAAAG AAGACACAAG   2340
CATTGGCTTA AAGCACGAAA TACGTCATGA TCAGGAAACT AAGACTACCA CGATAACGAA   2400
TGTTACGAGT TGCAAGCTTG AGTCGGAAGA AATGGTGGAA ATAATCCTGA AAAAAGCAAA   2460
TAAATTAAGA TCCACCGCTA GCACAGCATC AAATGAGCAT TCCTCCCGTT CACACAGTAT   2520
TTTCATAATT CATTTGTCTG GATCAAATGC AAAAACTGGA GCACACTCGT ATGGCACACT   2580
AAATCTTGTT GATTTGGCCG GTTCCGAAAG AATAAATGTC TCTCAAGTTG TAGGGGATAG   2640
ATTAAGAGAA ACACAAAATA TAAATAAATC TTTAAGTTGC TTAGGTGACG TTATTCATGC   2700
TTTAGGTCAG CCTGATAGTA CCAAAAGACA TATACCGTTC AGGAACTCAA AACTGACATA   2760
CCTACTGCAA TATTCACTCA CTGGGGATTC GAAAACATTA ATGTTTGTAA ACATTTCACC   2820
AAGCTCCTCT CATATTAATG AGACTCTCAA TTCGTTAAGA TTTGCGTCTA AAGTGAATTC   2880
TACCAGATTG GTTAGTAGAA AATGAGGTCA AGGCCTTTTC TGGTCTTTTT CACTCCTTTG   2940
ACAAATGACA GAGACTGTCC ATACATTCAT CACATGTAAC TATATTATAT ATGAAACTCA   3000
TTTTAATGCG CACAGATAAA AAGCAAAGTA AGTAATGAAT ATTTGTTATG TAAAAATGAC   3060
CTCATACATG CTAGTATTTA CACGAATTTA ATTGCTTAAA TTTCAATCAT CCTTACCCTT   3120
TGGTTTACCC TCTGGAGGCA GAAACTTTTG CATCCTCCTT ATTGCCCAAT TTTCGCCAAT   3180
GACTTTAACA TCTGGGTCCG ATTTACCTTC CGTGGTGTTG AACCGCTTCC ACCATGAGGG   3240
GGATTTGAAC CTAGGGTCTT CGCGTGGTAA TTTGCGAACT TCATTTCTAA TTTCAGCAAC   3300
```

```
ATGGGCTCTC AGTTCAGCGG CTAATCTGCT TCTTAAATCT TGCGCCTCTT TACCATATTT      3360

CAATTCGTCA GAGAGGTCGT TAGGATTTTT GGGATCATAG TATTTTTCAA CCAAATGTGT      3420

CCATTCTTTT CTATACCTGT CGATTAAATC ATCATTTAAA GGATCC                     3466
```

( 2 ) INFORMATION FOR SEQ ID NO:39:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:39:

```
GATAGTTAAG GATCCATGGC TCGTTCTTCC TTGCCCAACC GC                         42
```

( 2 ) INFORMATION FOR SEQ ID NO:40:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:40:

```
AAACTTCATC AATGCGGCCG CTAAGGGGAT CCAGCCATTG TAAAT                      45
```

( 2 ) INFORMATION FOR SEQ ID NO:41:

( i ) SEQUENCE CHARACTERISTICS:
        ( A ) LENGTH: 2385 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

```
GAATTCCGAT AGTATTATGT GGAGTTCCAT TTTTATGTAT TTTTGTATG AAATATTCTA       60

GTATAAGTAA ATATTTTATC AGAAGTATTT ACATATCTTT TTTTTTTTA GTTGAGAGC        120

GGCGGTGATC AGGTTCCCCT CTGCTGATTC TGGGCCCCGA ACCCCGGTAA AGGCCTCCGT      180

GTTCCGTTTC CTGCCGCCCT CCTCCGTAGC CTTGCCTAGT GTAGGAGCCC CGAGGCCTCC      240

GTCCTCTTCC CAGAGGTGTC GGGGCTTGGC CCCAGCCTCC ATCTTCGTCT CTCAGGATGG      300

CGAGTAGCAG CGGCTCCAAG GCTGAATTCA TTGTCGGAGG GAAATATAAA CTGGTACGGA      360

AGATCGGGTC TGGCTCCTTC GGGGACATCT ATTTGGCGAT CAACATCACC AACGGCGAGG      420

AAGTGGCAGT GAAGCTAGAA TCTCAGAAGG CCAGGCATCC CCAGTTGCTG TACGAGAGCA      480

AGCTCTATAA GATTCTTCAA GGTGGGGTTG GCATCCCCCA CATACGGTGG TATGGTCAGG      540

AAAAAGACTA CAATGTACTA GTCATGGATC TTCTGGGACC TAGCCTCGAA GACCTCTTCA      600

ATTTCTGTTC AAGAAGGTTC ACAATGAAAA CTGTACTTAT GTTAGCTGAC CAGATGATCA      660

GTAGAATTGA ATATGTGCAT ACAAAGAATT TTATACACAG AGACATTAAA CCAGATAACT      720

TCCTAATGGG TATTGGGCGT CACTGTAATA AGTGTTAGA ATCTCCAGTG GGGAAGAGGA       780

AAAGAAGCAT GACTGTTAGT ACTTCTCAGG ACCCATCTTT CTCAGGATTA AACCAGTTAT      840

TCCTTATTGA TTTTGGTTTG GCCAAAAAGT ACAGAGACAA CAGGACAAGG CAACACATAC      900
```

```
CATACAGAGA  AGATAAAAAC  CTCACTGGCA  CTGCCCGATA  TGCTAGCATC  AATGCACATC      960
TTGGTATTGA  GCAGAGTCGC  CGAGATGACA  TGGAATCATT  AGGATATGTT  TTGATGTATT     1020
TTAATAGAAC  CAGCCTGCCA  TGGCAAGGGC  TAAAGGCTGC  AACAAAGAAA  CAAAAATATG     1080
AAAAGATTAG  TGAAAAGAAG  ATGTCCACGC  CTGTTGAAGT  TTTATGTAAG  GGGTTTCCTG     1140
CAGAATTTGC  GATGTACTTA  AACTATTGTC  GTGGGCTACG  CTTGAGGAA   GCCCCAGATT     1200
ACATGTATCT  GAGGCAGCTA  TTCCGCATTC  TTTCAGGAC   CCTGAACCAT  CAATATGACT     1260
ACACATTTGA  TTGGACAATG  TTAAAGCAGA  AAGCAGCACA  GCAGGCAGCC  TCTTCCAGTG     1320
GGCAGGGTCA  GCAGGCCCAA  ACCCCACAG   GCAAGCAAAC  TGACAAAACC  AAGAGTAACA     1380
TGAAAGGTTA  GTAGCCAAGA  ACCAAGTGAC  GTTACAGGGA  AAAAATTGAA  TACAAAATTG     1440
GGTAATTCAT  TTCTAACAGT  GTTAGATCAA  GGAGGTGGTT  TTAAAATACA  TAAAAATTTG     1500
GCTCTGCGTT  AAAAAAAAAA  AAGACGTCCT  TGGAAAATTT  GACTACTAAC  TTTAAACCCA     1560
AATGTCCTTG  TTCATATATA  TGTATATGTA  TTTGTATATA  CATATATGTG  TGTATATTTA     1620
TATCATTTCT  CTTGGGATTT  TGGGTCATTT  TTTTAACAAC  TGCATCTTTT  TTACTCATTC     1680
ATTAACCCCC  TTTCCAAAAA  TTTGGTGTTG  GGAATATAAT  ATAATCAATC  AATCCAAAAT     1740
CCTAGACCTA  ACACTTGTTG  ATTTCTAATA  ATGAATTTGG  TTAGCCATAT  TTTGACTTTA     1800
TTTCAGACTA  ACAATGTTAA  GATTTTTTAT  TTTGCATGTT  AATGCTTTAG  CATTTAAAAT     1860
GGAAAATTGT  GAACATGTTG  TAATTTCAAG  AGGTGAGTTT  GGCATTACCC  CCAAAGTGTC     1920
TATCTTCTCA  GTTGCAGAGC  ATCTCATTTT  CTCTCTTAAA  TGCTCAAATA  AATGCAAAGC     1980
TCAGCACATC  TTTTCTAGTC  ACAAAAATAA  TTCTTTTATT  TGCAGTTTAC  GTATGATCTT     2040
AATTTCAAAA  CGATTTCTTT  GTTTTTGGCT  TGATTTTTCA  CAATGTTGCA  AATATCAGGC     2100
TCCCAGGGTT  TAATGTGGAA  TTGAAGTCTG  CAGCCAGGCC  TTGCAAATTG  AAGGTAACTG     2160
GGGCAAATGC  CATTGAAACC  GCTAGTCTTA  TTTCCTTTCT  ACTTTCTTT   GGCACTCTTA     2220
CTGCCTGTAA  GGAGTAGAAC  TGTTAAGGCA  CACTGTTGCT  ATACAGTTAA  CTCCCATTTT     2280
CATGTTTTGT  CTTTCTTTTC  CCATTTCTGG  GGCTTACCTC  CTGATACCTG  CTTACTTTCT     2340
GGAAGTAGTG  GGCAAGTAAG  ATTTGGCTCT  TGGTTTCTGG  AATTC                     2385
```

( 2 ) INFORMATION FOR SEQ ID NO:42:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

```
CTTCGTCTCT  CACATATGGG  CGAGTAGCAG  CGGC                                    34
```

( 2 ) INFORMATION FOR SEQ ID NO:43:

( i ) SEQUENCE CHARACTERISTICS:
        ( A ) LENGTH: 3505 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:43:

```
GAATTCCGAC  AGGAAAGCGA  TGGTGAAAGC  GGGGCCGTGA  GGGGGGCGGA  GCCGGGAGCC      60
```

| | | | | | |
|---|---|---|---|---|---|
| GGACCCGCAG | TAGCGGCAGC | AGCGGCGCCG | CCTCCCGGAG | TTCAGACCCA | GGAAGCGGCC | 120
| GGGAGGGCAG | GAGCGAATCG | GGCCGCCGCC | GCCATGGAGC | TGAGAGTCGG | GAACAGGTAC | 180
| CGGCTGGGCC | GGAAGATCGG | CAGCGGCTCC | TTCGGAGACA | TCTATCTCGG | TACGGACATT | 240
| GCTGCAGGAG | AAGAGGTTGC | CATCAAGCTT | GAATGTGTCA | AAACCAAACA | CCCTCAGCTC | 300
| CACATTGAGA | GCAAAATCTA | CAAGATGATG | CAGGGAGGAG | TGGGCATCCC | CACCATCAGA | 360
| TGGTGCGGGG | CAGAGGGGGA | CTACAACGTC | ATGGTGATGG | AGCTGCTGGG | GCCAAGCCTG | 420
| GAGGACCTCT | TCAACTTCTG | CTCCAGGAAA | TTCAGCCTCA | AAACCGTCCT | GCTGCTTGCT | 480
| GACCAAATGA | TCAGTCGCAT | CGAATACATT | CATTCAAAGA | ACTTCATCCA | CCGGGATGTG | 540
| AAGCCAGACA | ACTTCCTCAT | GGGCCTGGGG | AAGAAGGGCA | ACCTGGTGTA | CATCATCGAC | 600
| TTCGGGCTGG | CCAAGAAGTA | CCGGGATGCA | CGCACCCACC | AGCACATCCC | CTATCGTGAG | 660
| AACAAGAACC | TCACGGGGAC | GGCGCGGTAC | GCCTCCATCA | ACACGCACCT | GGAATTGAA | 720
| CAATCCCGAA | GAGATGACTT | GGAGTCTCTG | GGCTACGTGC | TAATGTACTT | CAACCTGGGC | 780
| TCTCTCCCCT | GGCAGGGGCT | GAAGGCTGCC | ACCAAGAGAC | AGAAATACGA | AAGGATTAGC | 840
| GAGAAGAAAA | TGTCCACCCC | CATCGAAGTG | TTGTGTAAAG | GCTACCCTTC | CGAATTTGCC | 900
| ACATACCTGA | ATTTCTGCCG | TTCCTTGCGT | TTTGACGACA | AGCCTGACTA | CTCGTACCTG | 960
| CGGCAGCTTT | TCCGGAATCT | GTTCCATCGC | CAGGGCTTCT | CCTATGACTA | CGTGTTCGAC | 1020
| TGGAACATGC | TCAAATTTGG | TGCCAGCCGG | GCCGCCGATG | ACGCCGAGCG | GGAGCGCAGG | 1080
| GACCGAGAGG | AGCGGCTGAG | ACACTCGCGG | AACCCGGCTA | CCCGCGGCCT | CCCTTCCACA | 1140
| GCCTCCGGCC | GCCTGCGGGG | GACGCAGGAA | GTGGCTCCCC | CCACACCCCT | CACCCCTACC | 1200
| TCACACACGG | CTAACACCTC | CCCCGGCCC | GTCTCCGGCA | TGGAGAGAGA | GCGGAAAGTG | 1260
| AGTATGCGGC | TGCACCGCGG | GGCCCCCGTC | AACATCTCCT | CGTCCGACCT | CACAGGCCGA | 1320
| CAAGATACCT | CTCGCATGTC | CACCTCACAG | ATTCCTGGTC | GGGTGGCTTC | CAGTGGTCTT | 1380
| CAGTCTGTCG | TGCACCGATG | AGAACTCTCC | TTATTGCTGT | GAAGGGCAGA | CAATGCATGG | 1440
| CTGATCTACT | CTGTTACCAA | TGGCTTTACT | AGTGACACGT | CCCCCGGTCT | AGGATCGAAA | 1500
| TGTTAACACC | GGGAGCTCTC | CAGGCCACTC | ACCCAGCGAC | GCTCGTGGGG | GAAACATACT | 1560
| AAACGGACAG | ACTCCAAGAG | CTGCCACCGC | TGGGGCTGCA | CTGCGGCCCC | CCACGTGAAC | 1620
| TCGGTTGTAA | CGGGGCTGGG | AAGAAAAGCA | GAGAGAGAAT | TGCAGAGAAT | CAGACTCCTT | 1680
| TTCCAGGGCC | TCAGCTCCCT | CCAGTGGTGG | CCGCCCTGTA | CTCCCTGACG | ATTCCACTGT | 1740
| AACTACCAAT | CTTCTACTTG | GTTAAGACAG | TTTTGTATCA | TTTTGCTAAA | AATTATTGGC | 1800
| TTAAATCTGT | GTAAAGAAAA | TCTGTCTTTT | TATTGTTTCT | TGTCTGTTTT | TGCGGTCTTA | 1860
| CAAAAAAAT | GTTGACTAAG | GAATTCTGAG | ACAGGCTGGC | TTGGAGTTAG | TGTATGAGGT | 1920
| GGAGTCGGGC | AGGGAGAAGG | TGCAGGTGGA | TCTCAAGGGT | GTGTGCTGTG | TTTGTTTTGC | 1980
| AGTGTTTTAT | TGTCCGCTTT | GGAGAGGAGA | TTTCTCATCA | AAAGTCCGTG | GTGTGTGTGT | 2040
| GTGCCCGTGT | GTGGTGGGAC | CTCTTCAACC | TGATTTTGGC | GTCTCACCCT | CCCTCCTCCC | 2100
| GTAATTGACA | TGCCTGCTGT | CAGGAACTCT | TGAGGCCCTC | GGAGAGCAGT | TAGGGACCGC | 2160
| AGGCTGCCGC | GGGGCAGGGG | TGCAGTGGGT | GTTACCAGGC | AAAGCACTGC | GCGCTTCTTC | 2220
| CCCAGGAGGT | GGGCAGGCAG | CTGAGAGCTT | GGAAGCAGAG | GCTTTGAGAC | CCTAGCAGGA | 2280
| CAATTGGGAG | TCCCAGGATT | CAAGGTGGAA | GATGCGTTTC | TGGTCCCTTG | GGAGAGGACT | 2340
| GTGAACCGAG | AGGTGGTTAC | TGTAGTGTTT | GTTGCCTTGC | TGCCTTTGCA | CTCAGTCCAT | 2400
| TTTCTCAGCA | CTCAATGCTC | CTGTGCGGAT | TGGCACTCCG | TCTGTATGAA | TGCCTGTGGT | 2460

| | | | | | |
|---|---|---|---|---|---|
| TAAAACCAGG | AGCGGGGCTG | TCCTTGCCAC | GTGCCAAGAC | TAGCTCAGAA | AAGCCGGCAG | 2520
| GCCAGAAGGA | CCCACCCTGA | GGTGCCAAGG | AGCAGGTGAC | TCTCCCAACC | GGACCCAGAA | 2580
| CCTTCACGGC | CAGAAAGTAG | AGTCTGCGCT | GTGACCTTCT | GTTGGGCGCG | TGTCTGTTGG | 2640
| TCAGAAGTGA | AGCAGCGTGC | GTGGGCCGA | GTCCACCAG | AAGGCAGGTG | GCCTCCGTGA | 2700
| GCTGGTGCTG | CCCCAGGCTC | CATGCTGCTG | TGCCCTGAGG | TTCCAGGAT | GCCTTCTCGC | 2760
| CTCTCACTCC | GCAGCACTTG | GGCGGTAGCC | AGTGGCCATG | TGCTCCCAAC | CCCAATGCGC | 2820
| AGGGCAGTCT | GTGTTCGTGG | GCACTTCGGC | TGGACCCCAT | CACGATGGAC | GATGTTCCCT | 2880
| TTGGACTCTA | GGGCTTCGAA | GGTGTGCACC | TTGGTTCTCC | CTTCTCCTCC | CCAGAGTTCC | 2940
| CCCGGATGCC | ATAACTGGCT | GGCGTCCCAG | AACACAGTTG | TCAACCCCCC | CACCAGCTGG | 3000
| CTGGCCGTCT | GTCTGAGCCC | ATGGATGCTT | TCTCAATCCT | AGGCTGGTTA | CTGTGTAAGC | 3060
| GTGTTGGAGT | ACGGCGCCTT | GAGCGGGTGG | GAGCTGTGTG | TTGAAGTACA | GAGGGAGGTT | 3120
| GGGGTGGGTC | AGAGCCGAGT | TAAGAGATTT | TCTTTGTTGC | TGGACCCCTT | CTTGAAGGTA | 3180
| GACGTCCCCC | ACCCGGAGAG | ACGTCGCGCT | GTGGCCTGAA | GTGGCGCAAG | CTTGCTTTGT | 3240
| AAATATCTGT | GGTCCCGATG | TAGTGCCCAG | AACGTTTGTG | CGAGGCAGCT | CTGCGCCCGG | 3300
| GTTCCAGCCC | GAGCCTCGCC | GGGTCGCGTC | TTCGGAGTGC | TTGTGACAGT | CCTTGCCCAG | 3360
| TATCTAGTCC | CCGTCGCCCC | GTGCAGGAGA | CGTAGGTAGG | ACGTCGTGTC | AGCTGTGCAC | 3420
| TGACGGCCAG | TCTCCGAGCT | GTGCGTTTGT | ATCGCCACTG | TATTTGTGTA | CTTTAACAAT | 3480
| CGTGTAAATA | ATAAATTCGG | AATTC | | | | 3505

( 2 ) INFORMATION FOR SEQ ID NO:44:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:44:

CGCGGATCCT AATGGAGGTG AGAGTCGGG    29

( 2 ) INFORMATION FOR SEQ ID NO:45:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:45:

CGCGGATCCG CTCATCGGTG CACGACAGA    29

( 2 ) INFORMATION FOR SEQ ID NO:46:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:46:

GGAATCACTA CAGGGATG    18

( 2 ) INFORMATION FOR SEQ ID NO:47:

( i ) SEQUENCE CHARACTERISTICS:
       ( A ) LENGTH: 30 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:47:

ATTCTAGACA TGGAGACCAG TTCTTTTGAG     30

( 2 ) INFORMATION FOR SEQ ID NO:48:

( i ) SEQUENCE CHARACTERISTICS:
       ( A ) LENGTH: 31 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:48:

TGGAAGCTTA TATTACCATA GATTCTTCTT G     31

TIH1, PROTEIN THAT INTERACTS WITH CASEIN KINASE I

This is divisional application of U.S. patent application Ser. No. 08/184,605, filed Jan. 21, 1994, now abandoned.

FIELD OF THE INVENTION

The present invention relates generally to identification of proteins, herein designated TIH proteins, that interact with casein kinase I isoforms and to isolation of polynucleotides encoding the same.

BACKGROUND

Protein kinases are post-translational, enzymatic regulators of cellular metabolism. Once activated, these enzymes transfer phosphate from ATP onto substrate proteins and in doing so affect the properties of substrate molecules. There are four broad classes of protein kinases including serine/threonine kinases, tyrosine kinases, multi-specific or dual-specific kinases, and histidine kinases [Hunter, et al., *Meth. Enzymol.* 200:3–37 (1991)]. In addition to the amino acid residue(s) of the substrate preferentially phosphorylated by the kinase, assignment of an enzyme to a particular class is based on its primary structure, its requirement for regulatory subunits, its requirement for second messengers, and its specific biochemical activity. See Hunter et al., supra, and Hanks and Quinn, *Meth. Enzymol.*, 200:38–62 (1991).

Serine/threonine protein kinases have been further divided into families of enzymes based on the mode of regulation of the enzymes and the quaternary structure of the active enzymes [Edelman, et al., *Ann. Rev. Biochem.* 56:567–613 (1987)]. Enzymes within the serine/threonine protein kinase family can differ in the substrates they phosphorylate, the specific phosphorylation sites they recognize, their mode of regulation and their subcellular distribution. Protein kinase A (PKA), for example, phosphorylates target substrates with the recognition/phosphorylation sequence R-R-X-S(P)-Y (SEQ ID NO: 1) [Pearson and Lemp, *Meth. Enzymol.* 200:62–81 (1991)], where S(P) represents the phosphrylated residue. The activity of PKA is localized by targeting subunits (called anchoring proteins or AKAPs, reveiwed in Hubbard and Cohen, *T.I.B.S.* 18:172–177, 1993). Members of the casein kinase I (CKI) family, on the other hand, recognize and phosphorylate serines and threonines near acidic residues in substrate proteins. The genes which encode yeast, rat, bovine and human isoforms of casein kinase I activity are structurally similar and the isoforms exhibit greater than 35%, and frequently greater than 50%, homology (identity) over their catalytic domains when compared to the prototypical *S. cerevisiae* CKI protein, HRR25, and are referred to herein as "HRR25-like" proteins. This degree of identity is significantly greater than the expected 25% found for comparing two randomly chosen protein kinases [Hanks and Quinn, supra]. The HRR25 DNA sequence is disclosed in Hoekstra, et al., *Science* 253:1031–1034 (1991); yeast CKI1 and CKI2 DNA sequences in Wang et al., *J. Mol. Biol. Cell,* 3:275–286 (1992) corresponding respectively to yeast sequences YCK2 and YCK1 in Robinson et al., *Proc. Natl. Acad. Sci. (USA)* 89:28–32 (1992); partial bovine CKIα, CKIβ, CKIγ and CKIδ DNA sequences and a full length homolog CKIα DNA sequence in Rowles, et al., *Proc. Natl. Acad. Sci. (USA)* 88:9548–9552 (1991); a full length rat CKIδ DNA sequence in Graves, et al., *J. Biol. Chem.,* 268:6394–6401 (1993); and a partial human erythroid CKIα DNA sequence in Brockman et al., *Proc. Natl. Acad. Sci. (USA)* 89:9454–9458 (1992).

The *S. cerevisiae* protein kinase HRR25 is one of the more extensively characterized isoforms of the CKI family [Hoekstra, supra]. Mutations in the HRR25 gene result in a variety of defects that include cell cycle delays, the inability to properly repair DNA strand breaks and characteristic morphological changes. The nature of these defects implies that HRR25 and other CKI isoforms play a significant role in cellular growth.

The importance of protein phosphorylation and protein kinases in health and disease states is evident in cases where expression of a particular kinase has gone awry; for example, chronic myelogenous leukemia arises from a translocation that places the breakpoint cluster region (BCR) gene next to the ABL tyrosine kinase gene, resulting in a fusion protein comprising the activated protein kinase [see review, Bishop, et al. *Cell* 64:235–288 (1991)]. In addition, many oncogenes, such as Mos [Watson, et al., *Proc. Natl. Acad. Sci. (USA)* 79:4078–4082 (1982)], Src [Anderson, et al., *Mol. Cell. Biol.* 5:1122–1129 (1985)] and Raf [Bonner, et al., *Nucl. Acids Res.* 14:1009–1015 (1986)] are protein kinases.

Most protein kinases phosphorylate a variety of substrates in vivo allowing diversity in responses to physiological stimuli [reviewed in Edelman, et al., supra]. However, the broader substrate specificity seen for many protein kinases in vitro, including activity towards non-physiological substrates, indicates that cellular mechanisms to control the specificity of these enzymes must exist in vivo. Understanding the regulatory mechanisms that govern these kinases and the specific role of the kinases in health and disease states requires the identification of substrates, regulatory proteins, and localizing/targeting proteins that interact with the kinases.

There thus exists a need in the an to identify proteins which interact with members of the casein kinase I family of enzymes and to characterize the interacting proteins in terms of their amino acid and encoding DNA sequences. Such information would provide for the large scale production of the proteins, allow for identification of cells which produce the kinases naturally and permit production of antibodies specifically reactive with the kinases. Moreover, elucidation of the substrates, regulation, and localization of these protein kinases would contribute to an understanding of the control of normal and malignant cell growth and provide information essential for the development of therapeutic agents useful for intervention in abnormal and/or malignant cell growth.

SUMMARY OF THE INVENTION

In one of its aspects, the present invention provides methods for identifying proteins, designated TIH proteins, that interact with CKI isoforms [i.e., *S. cerevisiae* HRR25 casein kinase I and HRR25-like protein kinases having at least 35% amino acid homology to HRR25 within the catalytic domain] and for isolating polynucleotides encoding the TIH proteins. A presently preferred method comprises the steps of: a) transforming or transfecting appropriate host cells with a DNA construct comprising a reporter gene under the control of a promoter regulated by a transcription factor having a DNA-binding domain and an activating domain; b) expressing in the host cells a first hybrid DNA sequence encoding a first fusion of part or all of a CKI isoform and either the DNA-binding domain or the activating domain of the transcription factor; c) expressing in the host cells a library of second hybrid DNA sequences encoding second fusions of part or all of putative CKI isoform-binding proteins and either the DNA-binding domain or DNA activating domain of the transcription factor which is not incorporated in the first fusion; d) detecting binding of CKI isoform-binding proteins to the CKI isoform in a particular host cell by detecting the production of reporter gene product in the host cell; and e) isolating second hybrid DNA sequences encoding CKI isoform-binding protein from the particular host cell. Variations of the method altering the order in which the CKI isoforms and putative CKI isoform-binding proteins are fused to transcription factor domains, i.e., at the amino terminal or carboxy terminal ends of the transcription factor domains, are contemplated. In a preferred version of the method, the promoter is the ADHI promoter, the DNA-binding domain is the lexA DNA-binding domain, the activating domain is the GAL4 trans-activation domain, the reporter gene is the lacZ gene and the host cell is a yeast host cell.

An alternative identification method comtemplated by the invention for detecting proteins which bind to a CKI isoform comprises the steps of: a) transforming or transfecting appropriate host cells with a hybrid DNA sequence encoding a fusion between a putative CKI isoform-binding protein and a ligand capable of high affinity binding to a specific counterreceptor; b) expressing the hybrid DNA sequence in the host cells under appropriate conditions; c) immobilizing fusion protein expressed by the host cells by exposing the fusion protein to the specific counterreceptor in immobilized form; d) contacting a CKI isoform with the immobilized fusion protein; and e) detecting the CKI isoform bound to the fusion protein using a reagent specific for the CKI isoform. Presently preferred ligands/counterreceptor combinations for practice of the method are glutathione-S-transferase/glutathione, hemagglutinin/hemagglutinin-specific antibody, polyhistidine/nickel and maltose-binding protein/amylose.

The present invention also provides novel, purified and isolated polynucleotides (e.g., DNA sequences and RNA transcripts, both sense and antisense strands) encoding the TIH proteins and variants thereof (i.e., deletion, addition or substitution analogs) which possess CKI and/or HRR25-binding properties inherent to the TIH proteins. Preferred DNA molecules of the invention include cDNA, genomic DNA and wholly or partially chemically synthesized DNA molecules. Presently preferred polynucleotides are the DNA molecules set forth in SEQ ID NOS: 2 (TIH1), 4 (TIH2), and 6 (TIH3), encoding the polypeptides of SEQ ID NOS: 3 (TIH1), 5 (TIH2), and 7 (TIH3), respectively. Also provided are recombinant plasmid and viral DNA constructs (expression constructs) which comprise TIH polypeptide-encoding sequences operatively linked to a homologous or heterologous transcriptional regulatory element or elements.

As another aspect of the invention, prokaryotic or eukaryotic host cells transformed or transfected with DNA sequences of the invention are provided which express TIH polypeptides or variants thereof. Host cells of the invention are particularly useful for large scale production of TIH polypeptides, which can be isolated from the host cells or the medium in which the host cells are grown.

Also provided by the present invention are purified and isolated TIH polypeptides, fragments and variants thereof. Preferred TIH polypeptides are as set forth in SEQ ID NOS: 3 (TIH1), 5 (TIH2), and 7 (TIH3). Novel TIH and TIH variant products of the invention may be obtained as isolates from natural sources, but are preferably produced by recombinant procedures involving host cells of the invention. Post-translational processing variants of TIH polypeptides may be generated by varying the host cell selected for recombinant production and/or post-isolation processing. Variant TIH polypeptides of the invention may comprise analogs wherein one or more of the amino acids are deleted or replaced: (1) without loss, and preferably with enhancement, of biological properties or biochemical characteristics specific for TIH polypeptides or (2) with specific disablement of a characteristic protein/protein interaction.

Also comprehended by the invention are antibody substances (e.g., monoclonal and polyclonal antibodies, single chain antibodies, chimeric antibodies, CDR-grafted antibodies and the like) which are specifically immunoreactive with TIH polypeptides. Antibody substances are useful, for example, for purification of TIH polypeptides and for isolation, via immunological expression screening, of homologous and heterologous species polynucleotides encoding TIH polypeptides. Hybridoma cell lines which produce antibodies specific for TIH polypeptides are also comprehended by the invention. Techniques for producing hybridomas which secrete monoclonal antibodies are well known in the art. Hybridoma cell lines may be generated after immunizing an animal with purified TIH polypeptides or variants thereof.

The scientific value of the information contributed through the disclosure of DNA and amino acids sequences of the present invention is manifest. As one series of examples, knowledge of the genomic DNA sequences which encode yeast TIH polypeptides permits the screening of a cDNA or genomic DNA of other species to detect homologs of the yeast polypeptides. Screening procedures, including DNA/DNA and/or DNA/RNA hybridization and PCR amplification are standard in the art and may be utilized to isolate heterologous species counterparts of the yeast TIH polypeptides, as well as to determine cell types which express these homologs.

DNA and amino acid sequences of the invention also make possible the analysis of TIH epitopes which actively participate in kinase/protein interactions as well as epitopes which may regulate such interactions. Development of agents specific for these epitopes (e. g., antibodies, peptides or small molecules) which prevent, inhibit, or mimic protein kinase-protein substrate interaction, protein kinase-regulatory subunit interaction, and/or protein kinase-protein localization molecule interaction are contemplated by the invention. Therapeutic compositions comprising the agents are expected to be useful in modulating the CKI/TIH protein interactions involved in cell growth in health and disease states.

BRIEF DESCRIPTION OF THE DRAWING

Numerous other aspects and advantages of the present invention will be apparent upon consideration of the following detailed description thereof, reference being made to the drawing wherein.

DETAILED DESCRIPTION

Figure 1:
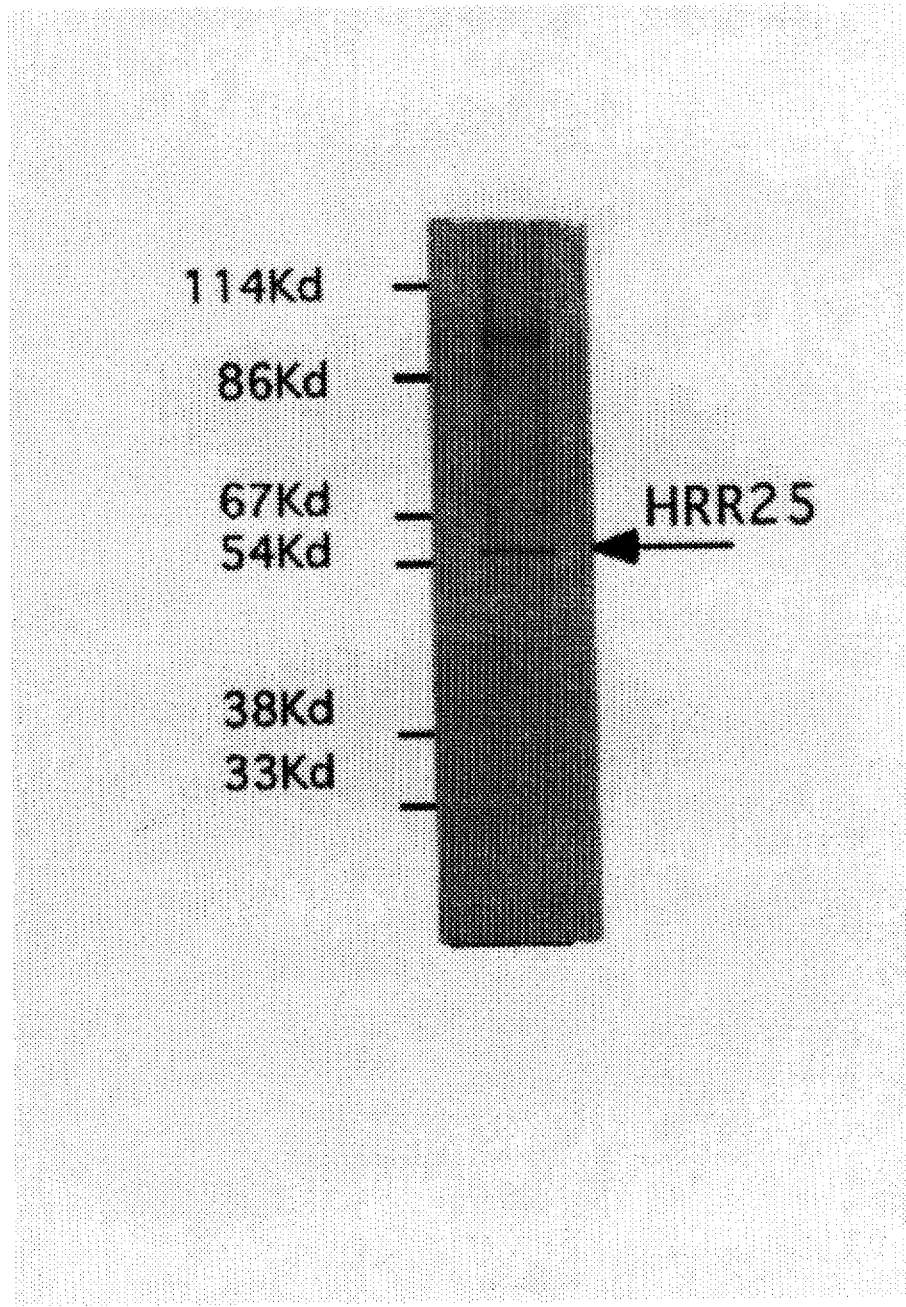
FIG. 1 is a Western blot demonstrating the association of S. cerevisiae HRR25 casein kinase I with affinity-purified TIH2.

The present invention generally relates to methods for identifying proteins that interact with CKI isoforms and is illustrated by the following examples relating to the isolation and characterization of genes encoding TIH polypeptides. More particularly, Example 1 addresses isolation of DNA sequences encoding TIH polypeptides from a yeast genomic library utilizing a dihybrid screening technique. Example 2 relates to analysis of the interaction between TIH polypeptides and various yeast CKI isoforms. Example 3 addresses interaction between a yeast CKI isoform, including mutants and fragments thereof, and kinesins. Example 4 describes analysis of the interaction between TIH polypeptides and human CKI isoforms. Example 5 addresses isolation of full length genomic DNA sequences which encode TIH polypeptides of the invention. Example 6 describes construction of a TIH knock-out mutant in yeast. Example 7 addresses analysis of S. cerevisiae HRR25/TIH polypeptides interactions utilizing affinity purification and Western blotting techniques.

EXAMPLE 1

Cellular components that interact with CKI isoforms were identified by a dihybrid screening method that reconstitutes a transcriptional transactivator in yeast. [A similar "two-hybrid" assay was originally described in Fields and Song, Nature, 340:245–246 (1989) and more recently in Yang et al., Science 257:681–682 (1992) and Vojtek et al., Cell, 74: 205–214 (1993).] In the assay, "bait" components (i.e., CKI isoforms) are fused to the DNA binding domain of a transcription factor (e.g., the lexA protein) and "prey" components (i.e., putative CKI interacting proteins) are fused to the transactivation domain of the transcription factor (e.g., GAL4). Recombinant DNA constructs encoding the fusion proteins are expressed in a host cell that contains a reporter gene fused to promoter regulatory elements (e.g. a lexA DNA binding site) recognized by the transcription factor. Binding of a prey fusion protein to a bait fusion protein brings together the GAL4 transactivation domain and the lexA DNA binding domain allowing interaction of the complex with the lexA DNA binding site that is located next to the β-galactosidase reporter gene, thus reconstituting transcriptional transactivation and producing β-galactosidase activity. In variations of the method, the "prey" component can be fused to the DNA binding domain of GAL4 and the "bait" components detected and analyzed by fusion to the transactivation domain of GAL4. Likewise, variations of this method could alter the order in which "bait" and "prey" components are fused to transcription factor domains, i.e., "bait" and "prey" components can be fused at the amino terminal or carboxy terminal ends of the transcription factor domains.

To identify genes encoding proteins that interact with S. cerevisiae HRR25 CKI protein kinase, a plasmid library encoding fusions between the yeast GAL4 activation domain and S. cerevisiae genomic fragments ("prey" components) was screened for interaction with a DNA binding domain hybrid that contained the E. coli lexA gene fused to HRR25 ("bait" component). The fusions were constructed in plasmid pBTM116 (gift from Bartell and Fields, SUNY) which contains the yeast TRP1 gene, a 2 μ origin of replication, and a yeast ADHI promoter driving expression of the E. coli lexA DNA binding domain (amino acids 1 to 202).

Plasmid pBTM116::HRR25, which contains the lex-A::HRR25 fusion gene, was constructed in several steps. The DNA sequence encoding the initiating methionine and second amino acid of HRR25 was changed to a SmaI restriction site by site-directed mutagenesis using a MutaGene mutagenesis kit from BioRad (Richmond, Calif.). The DNA sequence of HRR25 is set out in SEQ ID NO: 8. The oligonucleotide used for the mutagenesis is set forth below, wherein the SmaI site is underlined.

5'-CCT ACT CTT AGG CCC GGG TCT TTT TAA TGT ATC C-3'  (SEQ ID NO. 9)

After digestion with SmaI, the resulting altered HRR25 gene was ligated into plasmid pBTM116 at the SmaI site to create the lexA::HRR25 fusion construct.

Interactions between bait and prey fusion proteins were detected in yeast reporter strain CTY10-5d (genotype= MATa ade2 trp1-901 leu2-3,112 his 3-200gal4 gal80 URA3::lexA op-lacZ.) [Luban, et al., Cell 73:1067–1078 (1993)] carrying a lexA binding site that directs transcription of lacZ. Strain CTY10-5d was first transformed with plasmid pBTM116::HRR25 by lithium acetate-mediated transformation [Ito, et al., J. Bacteriol. 153:163–168 (1983)]. The resulting transformants were then transformed with a prey yeast genomic library prepared as GAL4 fusions in the plasmid pGAD [Chien, et al., Proc. Natl. Acad. Sci (USA) 21:9578–9582 (1991)] in order to screen the expressed proteins from the library for interaction with HRR25. A total of 500,000 double transformants were assayed for β-galactosidase expression by replica plating onto nitrocellulose filters, lysing the replicated colonies by quick-freezing the filters in liquid nitrogen, and incubating the lysed colonies with the blue chromogenic substrate 5-bromo-4-chloro-3-indolyl-β-D-galactoside (X-gal). β-galactosidase activity was measured using Z buffer (0.06M $Na_2HPO_4$, 0.04M $NaH_2PO_4$, 0.01M KCl, 0.001M $MgSO_4$, 0.05M β-mercaptoethanol) containing X-gal at a concentration of 0.002% [Guarente, Meth. Enzymol. 101:181–191 (1983)]. Reactions were terminated by floating the filters on 1M $Na_2CO_3$ and positive colonies were identified by their dark blue color.

Library fusion plasmids (prey constructs) that conferred blue color to the reporter strain co-dependent upon the presence of the HRR25/DNA binding domain fusion protein partner (bait construct) were identified. The sequence adjacent to the fusion site in each library plasmid was determined by extending DNA sequence from the GAL4 region. The sequencing primer utilized is set forth below.

5'-GGA ATC ACT ACA GGG ATG-3'  (SEQ ID NO. 10)

DNA sequence was obtained using a Sequenase version II kit (U.S. Biochemicals, Cleveland, Ohio) or by automated DNA sequencing with an ABI373A sequencer (Applied Biosystems, Foster City, Calif.).

Four library clones were identified and the proteins they encoded are designated herein as TIH proteins 1 through 4 for Ttargets Interacting with HRR25-like protein kinase isoforms. The TIH1 portion of the TIH1 clone insert corresponds to nucleotides 1528 to 2580 of SEQ ID NO: 2; the TIH2 portion of the TIH2 clone insert corresponds to nucleotides 2611 to 4053 of SEQ ID NO: 4; the TIH3 portion of the TIH3 clone insert corresponds to nucleotides 248 to 696 of SEQ ID NO: 6; and the TIH4 portion of the TIH4 clone insert is set out in SEQ ID NO: 11 and corresponds to nucleotides 1763 to 2305 of SEQ ID NO: 28. Based on DNA sequence analysis of the TIH genes, it was determined that TIH1 and TIH3 were novel sequences that were not representative of any protein motif present in the GenBank database (Jul. 8, 1993). TIH2 sequences were identified in the database as similar to a yeast open reading frame having no identified function. (GenBank Accession No. Z23261, open reading frame YBL0506) TIH4 represented a fusion protein between GAL4 and the carboxy-terminal portion of the kinesin-like protein KIP2. KIP2 has a highly conserved region which contains a kinesin-like microtubule-based motor domain [Roof et al., J. Cell. Biol. 118(1):95–108 (1992)]. The isolation of corresponding full length genomic clones for TIH1 through TIH3 is described in Example 5.

EXAMPLE 2

To investigate the specificity of interaction and regions of interaction between CKI isoforms and the TIH proteins, bait constructs comprising mutant or fragment HRR25 isoforms or other yeast (NUF1 and Hhp1) CKI isoforms fused to the lexA DNA binding domain were examined for transcription transactivation potential in the dihybrid assay.

Plasmid Constructions

To construct a plasmid containing a catalytically-inactive HRR25 protein kinase, HRR25 DNA encoding a lysine to arginine mutation at residue 38 (the ATP binding site) of HRR25 [DeMaggio et al., *Proc. Natl. Acad. Sci. (USA)* 89(15): 7008–7012 (1992)] was generated by standard site-directed mutagenesis techniques. The resulting DNA was then amplified by a PCR reaction which inserted a SmaI restriction site (underlined in SEQ ID NO. 12) before the HRR25 ATG using a mutagenic oligonucleotide:

5'-CCT TCC TAC TCT TAA GCC CGG GCC GCA GGA ATT CG-3'  (SEQ ID NO 12), and the downstream oligonucleotide which inserted a BamHI site (underlined):

5'-AGC AAT ATA GGA TCCTTA CAA CCA AAT TGA-3'  (SEQ ID 13).

Reactions included 200 mM Tris-Hcl (pH 8.2), 100 mM KCl, 60 mM $(NH_4)_2SO_4$, 15 mM $MgCl_2$, 1% Triton X-100, 0.5 µM primer, 100 ng template, 200 µM dNTP and 2.5 units polymerase. The reactions were performed for 30 cycles. Reactions were started with a 4 minute treatment at 94° C. and all cycles were 1 minute at 94° C. for denaturing, 2 minutes at 50° C. for annealing, and 4 minutes at 72° C. for extension. The resulting amplification product was digested with SmaI and ligated at the SmaI site of pBTM116 to produce the plasmid designated pBTM116::HRR25K→R encoding lexA sequences fused 5' to HRR25 sequences.

To construct a pBTM116 plasmid encoding a catalytic domain fragment of HRR25, two rounds of site-directed mutagenesis were performed to introduce a SmaI site in place of the initiating ATG and second codon of HRR25 DNA and a BamHI site at nucleotide 1161 (refer to SEQ ID NO. 8) or amino acid 397 of HRR25. The mutagenic oligonucleotide used to introduce the 5' SmaI restriction site (underlined) was:

5'-CCT ACT CTT AAG CCC GGG TCT TTT TAA TGT ATC C-3'  (SEQ ID NO. 14), and the oligonucleotide used to create the 3', or downstream, BamHI site (underlined) at residue 397 was:

5'-GTC TCA AGT TTT GGG ATC CTT AAT CTA GTG CG-3'  (SEQ ID NO. 15).

The resulting product was digested with SmaI-BamHI and the fragment encoding the HRR25 catalytic domain (corresponding to nucleotides 2 to 1168 of SEQ ID NO: 8) was subcloned into plasmid pBTM116 linearized with the same enzymes to produce the plasmid designated pBTM116::Kinase domain encoding lexA sequences fused 5' to HRR25 sequences.

To construct a pBTM116 plasmid containing the non-catalytic domain fragment of HRR25, a SmaI site (underlined) was introduced at nucleotide 885 (amino acid 295) using site-directed mutagenesis with the following oligonucleotide:

5'-CAC CAT CGC CCC CGG GTA ACG CAA CAT TGT CC-3'  (SEQ ID NO: 16).

The resulting product was digested with SmaI and BamHI and the fragment encoding the HRR25 non-catalytic domain (corresponding to nucleotides 885 to 1485 of SEQ ID NO: 8) was subcloned into plasmid pBTM116 linearized with the same enzymes to produce the plasmid designated pBTM116::Non-catalytic encoding lexA sequences fused 5' to HRR25 sequences.

To construct a fusion with the *S. cerevisiae* NUF1 isoform of CKI in plasmid pBTM116, a SmaI site (underlined) was introduced by site-directed mutagenesis in place of the initiating ATG and second codon of NUF1 DNA (SEQ ID NO: 17) using the oligonucleotide:

5'-TGA AGA TCG TTG GCC CGG GTT TCC TTA TCG TCC-3'  (SEQ ID NO. 18).

The resulting product was digested with SmaI and BamHI and the NUF1 fragment was ligated into pBTM116 linearized with the same enzymes sites to produce the plasmid designated pBTM 116::NUF1 encoding lexA sequences fused 5' to NUF1 sequences.

To construct a fusion with the *S. pombe* Hhp1 isoform of CKI in plasmid pBTM116, a SmaI site (underlined) was introduced by site-directed mutagenesis in place of the initiating ATG and second codon of Hhp1 DNA (SEQ ID NO: 19) using the oligonucleotide:

5'-GGG TTA TAA TAT TAT CCC GGG TTT GGA CCT CCG G-3'  (SEQ ID NO. 20).

The resulting product was digested with SmaI and BamHI and the HhpI fragment was ligated into pBTM116 linearized with the same enzymes to produce plasmid pBTM116::Hhp1 encoding lexA sequences fused 5' to Hhp1 sequences.

Assays

To measure protein/protein interaction levels between wild-type and mutant CKI isoforms and TIH proteins of the invention, standard yeast mating techniques were used to generate yeast strains containing all pairwise combinations of the isoforms and TIH proteins. All CKI isoform-encoding pBTM 116-based plasmids were transformed into yeast by lithium acetate-mediated transformation methods and transformants were selected on SD-tryptophan medium (Bio101, La Jolla, Calif.). The yeast strain CTY10-5d used for pBTM116-based transformations was mating type α. All TIH protein-encoding pGAD-based plasmids described in Example 1 were transformed using the lithium acetate method into yeast and transformants were selected on SD-leucine medium. The yeast strain used for pGAD-based transformations was mating type a. This MATa strain is isogenic to CTY10-5d and was constructed by introducing the HO gene using plasmid pGALHO [Jenson and Herskowitz, *Meth. Enzymol.* 194:132–146 (1991)] in lithium acetate-mediated transformation, inducing the HO gene with galactose to cause a mating-type interconversion, and growing the strain non-selectively to isolate a derivative that had switched mating type.

To construct pairwise combinations between pBTM116-based plasmids and pGAD-based plasmids, yeast strains of opposite mating types were replica plated in a crossed pattern on YEPD medium (Bio101) and were allowed to mate for 18 hours. Diploid cells were selected by a second replica plating onto SD-leucine, -tryptophan medium to select for cells that contained both pBTM116-type and pGAD-type plasmids. The isolated diploids were grown in liquid SD-leucine, -tryptophan medium to a cell density of 2×10⁷ cells/ml and the level of interaction of the kinase and interacting protein, as determined by beta-galactosidase activity, was determined from cells that were lysed by adding 3 drops of chloroform and 50 μl of 0.1% SDS to 2×10⁶ cells suspended in 0.1 ml of Z buffer and subsequently adding 0.2 ml of the chromogenic substrate o-nitrophenyl-β-D-galactoside. β-galactosidase assays were terminated by adding 0.5 ml of 1M Na$_2$CO$_3$ and activity was measured by reading absorbance at 420 nm using a Milton Roy spectrophotometer (Rochester, N.Y.). In this assay, the degree of protein/protein interaction is directly proportional to the level of β-galactosidase activity. The relative β-galactosidase activity measurements obtained are given in Table 1, wherein a value of <5 indicates that the level of β-galactosidase activity was not greater than background and a value of 10 indicates a easily detectable level of activity. Values were normalized to vector alone controls.

TABLE 1

Yeast CKI/TIH Protein Interactions

| PLASMID CONSTRUCTS ASSAYED | pGAD::TIH1 | pGAD::TIH2 | pGAD::TIH3 |
|---|---|---|---|
| pBTM116 | <5 | <5 | <5 |
| pBTM116:HRR25 | 850 | 650 | 100 |
| pBTM116:HRR25 K→R | 100 | 150 | 30 |
| pBTM116::Kinase Domain | 820 | 160 | 130 |
| pBTM116::Non-catalytic | <5 | <5 | <5 |
| pBTM116::NUF1 | <5 | <5 | 10 |
| pBTM116::Hhp1 | <5 | 20 | 450 |

The results show significant interaction between HRR25 protein kinase and the TIH proteins. Furthermore, the interaction appeared to require an active protein kinase; the region of HRR25 that interacted with the TIH proteins is localized to the protein kinase domain of HRR25. TIH proteins of the invention also interacted with other CKI isoforms. For example, TIH3 interacted with NUF1, and TIH2 and TIH3 interacted with Hhp1.

EXAMPLE 3

Because HRR25 mutants (hrr25) show chromosome segregation defects and because kinesins are involved in chromosome segregation, the interaction of several different kinesins with the CKI bait fusions described in Example 2 was examined. To date, the kinesin gene family in yeast includes proteins designated KIP1 (Roof et al. supra), KIP2 ,(Roof et al., supra), CIN8 [Hoyt et al., *J. Cell. Biol.* 11(1): 109–120 (1992)] and KAR3 [Meluh et al., *Cell* 60(6): 1029–1041 (1990)]. To construct the prey kinesin fusion plasmids, genomic clones of KIP1, KIP2, CIN8, and KAR3 were first isolated and then subcloned into plasmid pGAD which contains the transactivating domain of GAL4. Interactions of the CKI bait fusions with the TIH4 prey fusion (pGAD::TIH4) described in Example 1 were examined concurrently.

Plasmid Construction

KIP1 sequences were amplified from *S. cerevisiae* genomic DNA using the following two primers:

5'-TCC CTC TCT AGA TAT GGC GAG ATA GTT A-3'  (SEQ ID NO: 21)

and

5'-GTT TAC ACT CGA GGC ATA TAG TGA TAC A-3'  (SEQ ID NO: 22).

The amplified fragment was labelled with ³²P by random primed labelling (Boehringer Mannheim, Indianapolis, Ind.) and used to screen a yeast genomic library constructed in the plasmid pRS200 (ATCC 77165) by colony hybridization. Hybridizations were performed at 65° C. for 18 hours in 6× SSPE (20× SSPE is 175.3 g/l NaCl, 27.6 g/l NaH2PO4.H2), 7.4 g.l EDTA, pH7.4, 100 μg/ml salmon sperm carrier DNA, 5× Denhardts Reagent (50× Denhardts is 5% ficoll, 5% polyvinyl pyrolidone, 5% bovine serum albumin), 0.1% SDS, and 5% sodium dextran sulfate. Filters were washed four times in 0.1× SSPE, 1% SDS. Each wash was at 65° C. for 30 minutes. Two rounds of site-directed mutagenesis were then performed as described in Example 2 to introduce BamHI sites at the start and end of KIP1 coding sequences (SEQ ID NO: 23). Mutagenesis was performed using a Muta-gene Mutagenesis Kit, Version 2 (BioRad). The oligonucleotide for introducing a BamHI site (underlined) in place of the KIP1 ATG and second codon was:

5'-GAT AGT TAA GGA TCC ATG GCT CGT TCT TCC TTG
CCC AAC CGC-3'  (SEQ ID NO: 24), and the oligonucleotide encoding a stop codon (double underlined) and BamHI site (underlined) was:

5'-AAA CTT CAT CAA TGC GGC CGC TAA GGG GAT CCA
GCC ATT GTA AAT-3'  (SEQ ID NO: 25).

The resulting KIP1 product was digested with BamHI and cloned into pGAD immediately downstream of GAL4 sequences and the plasmid was called pGAD::KIP1.

KIF2 sequences were amplified from *S. cerevisiae* genomic DNA using the following two primers:

5'-TTT CCT TGT TTA TCC TTT TCC AA-3'  (SEQ ID NO: 26)

and

5'-GAT CAC TTC GGA TCC GTC ACA CCC AGT
TAG-3'  (SEQ ID NO: 27).

The amplified fragment was labelled with ³²P by random primed labelling and used to screen a yeast genomic library constructed in the plasmid YCp50 (ATCC 37415) by colony hybridization. Hybridizations and washes were as described above for KIP1. Two rounds of site-directed mutagenesis were performed to introduce BamHI sites at the start and end of KIP2 coding sequences (SEQ ID NO: 28). The oligonucleotide for introducing a BamHI site (underlined) in place of the KIF2 ATG and second codon was:

5'-ACC ATA ATA CCA GGA TCC ATG ATT CAA
AAA-3'  (SEQ ID NO: 29)

and the oligonucleotide encoding a BamHI site (underlined) was:

5'-CCT GTC GTG GAT AGC GGC CGC TAG GAT CCT GAG
GGT CCC AGA-3'  (SEQ ID NO: 30).

The resulting KIP2 product was digested with BamHI and cloned into pGAD immediately downstream of GAL4 sequences and the plasmid was called pGAD::KIP2.

CIN8 sequences were amplified from *S. cerevisiae* genomic DNA using the following two primers:

5'-ACA TCA TCT AGA GAC TTC CTT TGT GAC
C-3'  (SEQ ID NO: 31)

and

5'-TAT ATA ATC GAT TGA AAG GCA ATA
TC-3'  (SEQ ID NO: 32).

The amplified fragment was labelled with ³²P by random primed labelling and used to screen a yeast genomic library constructed in the plasmid pRS200 (ATCC 77165) by colony hybridization. Hybridizations and washes were as described above for KIP1. Two rounds of site-directed mutagenesis were performed to introduce BamHI sites at the start and end of CIN8 coding sequences (SEQ ID NO: 33). The oligonucleotide utilized for introducing a BamHI site (underlined) in place of the CIN8 ATG and second codon was:

5'-CGG GTG TA<u>G GAT CC</u>A TGG TAT GGC CAG AAA GTA ACG-3'  (SEQ ID NO: 34)

and the downstream oligonucleotide encoding a BamHI site (underlined) and a stop codon (double underlined) was:

5'-GTG GAC AAT GGC GGC CGC AGA AAA A<u>GG ATC C</u>AG <u>ATT</u> GAA TAG TTG ATA TTG CC-3'  (SEQ ID NO: 35).

The resulting CIN8 product was digested with BamHI and cloned into pGAD immediately downstream of GAL4 sequences and the plasmid was called pGAD::CIN8.

KAR3 was amplified from S. cerevisiae genomic DNA using the following two primers:

5'-GAA TAT TCT AGA ACA ACT ATC AGG AGT C-3'  (SEQ ID NO: 36)

and

5'-TTG TCA CTC GAG TGA AAA AGA CCA G-3'  (SEQ ID NO: 37).

The amplified fragment was labelled with $^{32}$P by random primed labelling and used to screen a yeast genomic library constructed in the plasmid pRS200 (ATCC 77165) by colony hybridization. Hybridizations and washes were as described above for KIP1. Two rounds of site-directed mutagenesis were performed to introduce BamHI sites at the start and end of KAR3 coding sequences (SEQ ID NO: 38). The oligonucleotide for introducing a BamHI site (underlined) in place of the KAR3 ATG and second codon was:

5'-GAT AGT TAA <u>GGA TCC</u> ATG GCT CGT TCT TCC TTG CCC AAC CGC-3'  (SEQ ID NO: 39)

and the oligonucleotide encoding a BamHI site (underlined) and a stop codon (double underlined) was:

5'-AAA CTT CAT CAA TGC GGC CGC TAA G<u>GG GAT CC</u>A GCC A<u>TT</u> GTA AAT-3'  (SEQ ID NO: 40).

The resulting KAR3 product was digested with BamHI and cloned into pGAD immediately downstream of GAL4 sequences and the plasmid was called pGAD::KAR3.

The prey plasmids were transformed into yeast by lithium acetate-mediated transformation and the transformants were mated to CKI isoform-encoding yeast strains as described in Example 2. β-galactosidase activity of CKI isoform/TIH-containing strains was determined from cells that were lysed by adding 3 drops of chloroform and 50 µl of 0.1% SDS to 2×10⁶ cells suspended in 0.1 ml of Z buffer and subsequently adding 0.2 ml of the chromogenic substrate o-nitrophenyl-β-D-galactoside. β-galactosidase assays were terminated by adding 0.5 ml of 1M Na₂CO₃ and activity was measured by reading absorbance at 420 nm using a Milton Roy spectrophotometer (Rochester, N.Y.). In this assay, the degree of protein/protein interaction is directly proportional to the level of β-galactosidase activity. The results of the assay are presented as units of β-galactosidase activity in Table 2.

TABLE 2

β-Galactosidase Activity Resulting From CKI Isoform/Kinesin Interaction

|  | pGAD:: KIP1 | pGAD:: KIP2 | pGAD:: TIH4 | pGAD:: KAR3 | pGAD:: CIN8 |
|---|---|---|---|---|---|
| pBTM116::HRR25 | 16 | 10 | 70 | 15 | 5 |
| pBTM116::HRR25 K→R | 55 | 16 | 66 | 75 | 28 |
| pBTM116::Non-Catalytic | 70 | <0.1 | <0.1 | 60 | <0.1 |

The results indicate that HRR25 can interact with all four yeast kinesins and TIH4. Kinesins KIP2 and CIN8 interact with the catalytic domain of HRR25 while kinesins KIP1 and KAR3 interact with kinase-inactive HRR25 and with the non-catalytic domain of HRR25, suggesting that kinase/substrate interaction progresses through strong binding to enzymatic activity. In addition, the results show that HRR25 interacts with the carboxy-terminal portion of TIH4 or, because TIH4 corresponds to KIP2, KIP2.

EXAMPLE 4

Assays were also performed to determine whether human CKI isoforms would interact with the TIH proteins of the invention. Two human CKI isoforms, CKIα3 (CKIα3Hu) and CKIδ (CKIδHu), were selected for this analysis. The human CKI genes were fused to the GAL4 DNA binding domain previously inserted into plasmid pAS [Durfee, et al., Genes and Development 7:555–569 (1993)] to produce pAS::CKIα3 and pAS::CKIδ.

Specifically, the CKIα3Hu isoform-encoding DNA (SEQ ID NO: 41) was subjected to site-directed mutagenesis using the mutagenic oligonucleotide:

5'-CTT CGT CTC TCA <u>CAT ATG</u> GGC GAG TAG CAG CGG C-3'  (SEQ ID NO. 42)

to create NdeI site (underlined) in the place of the CKIα3Hu initiating methionine and second codon, and the resulting DNA was digested with NdeI and ligated into plasmid pAS at a NdeI site located immediately downstream of GAL4 sequences.

CKIδHu DNA (SEQ ID NO: 43) was introduced into pAS by amplifying the CKIδcDNA with mutagenic oligonucleotide primers that contained BamHI sites. The oligonucleotides, with BamHI sites underlined, used were:

5'-CGC <u>GGA TCC</u> TAA TGG AGG TGA GAG TCG GG-3'  (SEQ ID NO. 44), replacing the initiating methionine and second codon, and 5'-CGC <u>GGA TCC</u> GCT CAT CGG TGC ACG ACA GA-3'  (SEQ ID NO. 45).

Reactions included 200 mM Tris HCl (pH 8.2), 100 mM KCl, 60 mM (NH₄)₂SO₄, 15 mM MgCl₂, 1% Triton X-100, 0.5 µM primer, 100 ng template, 200 µM dNTP and 2.5 units polymerase. The reactions were performed for 30 cycles. Reactions were started at 94° C. for 4 minutes and all subsequent cycles were 1 minute at 94° C. for denaturating, 2 minutes at 50° C. for annealing, and 4 minutes at 72° C. for extension. The amplified product was digested with BamHI and ligated into BamHI-digested pAS immediately downstream of GAL4 sequences to create plasmid pAS: CKIδ.

The resulting bait plasmids were transformed into yeast by lithium acetate-mediated transformation and the transformants were mated to TIH-encoding yeast strains as described in Example 2. β-galactosidase activity of CKIα3Hu- or CKIδHu-containing/TIH-containing strains was detected by replica plating cells onto Hybond-N$^{0.45\mu}$ hybridization filters (Amersham, Arlington Heights, Ill.), growing cells on the filters at 30° C. for 18 hours, lysing the colonies by freezing the filters in liquid nitrogen, and incubating the filters on Whatman filter paper soaked in Z buffer containing 0.002% X-gal. Reactions were terminated by soaking the filters in 1M $Na_2CO_3$ and protein/protein interaction was evaluated by examining for a chromogenic conversion of X-gal to blue by β-galactosidase activity. The results of the assay, as determined by visual screening for development of blue color are presented below in Table 3.

TABLE 3

β-Galactosidase Activity Resulting From Human CKI/TIH Interaction

| PLASMID CONSTRUCTS USED | TIH1 | TIH2 | TIH3 |
|---|---|---|---|
| pAS::CKIα3 | − | − | − |
| pAS::CKIδ | − | + | − |

These results indicate that interaction between TIH proteins of the invention and CKI isoforms is not limited to yeast isoforms. CKIδHu interacted with TIH2. Thus, CKI/TIH interactions can be expected to occur between human CKIs and their cognate TIH proteins.

EXAMPLE 5

Full length genomic clones encoding the yeast TIH1, TIH2, and TIH3 proteins were isolated from a yeast genomic library. To identify genomic clones, radiolabelled PCR fragments were prepared from the pGAD plasmids containing TIH1, TIH2, and TIH3 fusion genes described in Example 1. The sequence of the unidirectional oligonucleotide used to amplify the clones was:

5'-GGA ATC ACT ACA GGG ATG-3'   (SEQ ID NO: 46).

PCR reactions included 200 mM Tris HCl (pH 8.2), 100 mM KCl, 60 mM $(NH_4)_2SO_4$, 15 mM $MgCl_2$, 1% Triton X-100, 0.5 μM primer, 100 ng template, 200 μM dNTP and 2.5 units polymerase. The reactions were performed for 30 cycles. The first five cycles contained 50 μCi each $^{32}$P-dCTP and $^{32}$P-TTP. At the start of the sixth cycle, non-radiolabeled dCTP and TTP were each added to 200 μM final concentration. Reactions were started at 94° C. for 4 minutes and all subsequent cycles were performed for 1 minute at 94° C. for denaturation, 2 minutes at 50° C. for annealing, and 4 minutes at 72° C. for extension. The resulting PCR products were then used as probes in colony hybridization screening.

The full length TIH1 genomic clone was isolated from a YCp50 plasmid library (ATCC 37415). The full length TIH2 and TIH3 genomic clones were isolated from a λ genomic library [Riles, et al., *Genetics* 134:81–150 (1993)]. Hybridization for YCp50 library screening were performed at 65° C. for 18 hours in 6× SSPE (20× SSPE is 175.3 g/l NaCl, 27.6 g/l $NaH_2PO_4$, $H_2$), 7.4 g.l EDTA, pH7.4, 100 μg/ml salmon sperm carrier DNA, 5× Denhardts Reagent (50× Denhardts is 5% ficoll, 5% polyvinyl pyrolidone, 5% bovine serum albumin), 0.1% SDS, and 5% sodium dextran sulfate. Filters were washed four times in 0.1× SSPE, 1% SDS. Each wash was at 65° C. for 30 minutes. Hybridization conditions for λ library screening were 18 hours at 64° C. in 1× HPB (0.5M NaCl, 100 mM $Na_2HPO_4$, 5 mM $Na_2EDTA$), 1% sodium sarkosyl, 100 μg/ml calf thymus DNA. Filters were washed two times for 15 seconds, one time for 15 minutes, and one time for 15 seconds, all at room temperature in 1 mM Tris-HCl (pH 8.0). The sequences of TIH1, TIH2, and TIH3 genomic clones were determined by automated DNA sequencing with an ABI 373A sequencer (Applied Biosystems). Nucleotide sequences determined for the full length TIH1, TIH2 and TIH3 genomic clones are set out in SEQ ID NOS: 2, 4, and 6, respectively; the deduced amino acid sequences for TIH1, TIH2, and TIH3 are set out in SEQ ID NOS: 3, 5, and 7, respectively. Database searches confirmed the results from Example 1 that the TIH1 and TIH3 genes encoded novel proteins showing no significant homology to any protein in the GenBank database.

EXAMPLE 6

To characterize activity of the TIH proteins and to determine if the TIH proteins participate in a HRR25 signalling pathway, a chromosomal TIH1 deletion mutant was constructed by homologous recombination.

Specifically, the TIH1 mutation was constructed by subcloning a 1.7 kb SalI-BamHI fragment that encompasses the genomic TIH1 gene into plasmid pBluescript II SK (Stratagene, La Jolla, Calif.). The resulting subclone was digested with EcoRV and PstI to delete 0.5 kb of the TIH1 gene (nucleotides 1202 to 1635 of SEQ ID NO: 2) and into this region was ligated a 2.2 kb SmaI-PstI fragment that contained the *S. cerevisiae* LEU2 gene. Isolated DNA from the resulting plasmid construct was digested with BamHI to linearize the plasmid and 10 μg of this sample were used to transform a diploid yeast strain that is heterologous for HRR25 (MAT a/MAT α ade2/ade2 can1/can1 his3-11,15/his3-11,15 leu2-3,112/leu2-3,112 trp1-1/trp1-1 ura3-1/ura3-1 HRR25/::URA3) to Leu$^+$. Transformation was carried out using lithium acetate-mediated procedures and transformants were selected on SD-Leucine medium (Bio101). Yeast transformation with linearized DNA results in homologous recombination and gene replacement [Rothstein, *Meth. Enzymol* 194:281–301 (1991)]. Stable Leu$^+$ colonies were replica plated onto sporulation medium (Bio101) and grown at 30° C. for five days. Spores were microdissected on YEPD medium (Bio101) using a tetrad dissection apparatus [Sherman and Hicks, *Meth. Enzymol.* 194:21–37 (1991)] and isolated single spores were allowed to germinate and grow into colonies for three days.

Four colony types were detected due to random meiotic segregation of the heterologous TIH1 and HRR25 mutations present in the strain. The hrr25 deletion mutation in the parent strain was due to a replacement of the HRR25 gene with the yeast URA3 gene and the TIH1 mutation is due to a replacement with LEU2. URA3 and LEU2 confer uracil and leucine prototropy, respectively. The colony types are represented by segregation of the mutations into following genotypic configurations: (i) wild type cells are HRR25 TIH1; (ii) HRR25 mutants are hrr25::URA3 TIH1; (iii) TIH1 mutants are HRR25 tih1::LEU2; and (iv) HRR25 TIH1 double mutants are hrr25::URA3 tih1::LEU2. Standard physiological analyses of yeast mutant defects were performed [Hoekstra et al., supra].

TIH1 deletion mutants exhibited phenotypes identical to mutations in HRR25 including slow growth rate, DNA repair defects, and aberrant cellular morphology, indicating that the TIH proteins participate in the same pathway as HRR25 or in pathways having similar effects. Furthermore, tih1 hrr25 double mutants were inviable.

EXAMPLE 7

To confirm the dihybrid screen analysis of interaction between CKI protein kinases and TIH proteins, a biochemical method was developed to detect the interaction. This method was based on affinity purification of one component in the interaction, followed by Western blotting to detect the presence of the interacting component in the affinity purified mixture. The TIH2 gene was used to construct a TIH2/ glutathione-S-transferase (GST) fusion protein which could be affinity purified with glutathione agarose (Pharmacia, Uppsala, Sweden) Other useful ligand/counterreceptor combinations include, for example, influenze virus hemagglutinin [Field et al., Mol. Cell Biol. 8(5 ): 2159–2165 (1988)]/ hemagglutinin-specific antibody (Berkeley Antibody Company, Richmond, Calif.), polyhistidine/nickel affinity chromatography (Novagen, Madison, Wis.), and maltose-binding protein/amylose chromotography (New England Biolabs, Beverly, Mass.).

To construct the GST::TIH2 fusion protein, the 5' and 3' termini of the TIH2 gene were modified by DNA amplification-based mutagenesis procedures. The amplifying oligonucleotides introduced XbaI and HindIII sites for ease in subcloning. The oligonucleotides, with restricition sites underlined, used for amplification were:

5'-AT<u>T CTA GAC</u> ATG GAG ACC AGT TCT TTT
   GAG-3'                         (SEQ ID NO. 47)

and,

5'-TGG <u>AAG CTT</u> ATA TTA CCA TAG ATT CTT CTT
    G-3'                          (SEQ ID NO. 48).

Reactions included 200 mM Tris. HCl (pH 8.2), 100 mM KCl, 60 mM $(NH_4)_2SO_4$, 15 mM $MgCl_2$, 1% Triton-X-100, 0.5 µM primer, 100 ng template, 200 µM dNTP and 2.5 units polymerase. The reactions were performed for 30 cycles. Reactions were started at 94° C. for 4 minutes and all subsequent cycles were 1 minute at 94° C. for denaturation, 2 minutes at 50° C. for annealing, and 4 minutes at 72° C. for extension.

The resulting amplified product was digested with XbaI and HindIII and the fragment was subcloned into the GST-containing plasmid pGEXKG, which contained a galactose-inducible GST gene, to create pGEXKG::TIH2. This plasmid contains, in addition to the GST sequences fused immediately upstream of TIH2 seqences, URA3 and LEU2 selectable markers for yeast transformation. Plasmid pGEXKG::TIH2 was then transformed by lithium acetate-mediated transformation into yeast strain W303 [Wallis, et al., Cell 58:409–419 (1989)] and $Ura^+$ transformants were selected on SD-URA medium (Bio101). To isolate the GST::TIH2 fusion protein, 100 ml SD-URA broth was innoculated with the transformed yeast and grown to a density of $1\times10^7$ cells/ml in the presence of galaclose. The cells were then pelleted by centrifugation, washed in lysis buffer [10 mM sodium phosphate pH 7.2, 150 mM NaCl, 1% Nonidet P-40, 1% Trasylol protease inhibition (Miles), 1 mM dithiothreitol, 1 mM benzamidine, 1 mM phenylmethyl sulphonyl fluoride, 5 mM EDTA, 1 µg/ml pepstalin, 2 µg/ml pepstatin A, 1 µg/ml leupeptin, 100 mM sodium vanadate, and 50 mM NaF], resuspended in 1 ml lysis buffer, and lysed by vortexing for 5 minutes with 10 g of glass beads. The crude lysate was clarified by centrifugation at 100,000× g for 30 minutes. Fifty µl of 50% slurry glutathione agarose (Pharmacia) were added to the extract and the mixture incubated for 1 hour. The agarose was pelleted by a 10 second spin in an Eppendorf microcentrifuge, the supernate removed, and the agarose-containing pellet washed with phosphate-buffered saline (PBS). The pellet was resuspended in 50 µl of 2× protein gel sample buffer, boiled for 2 minutes, and 12.5 µl was electrophoresed through a 10% polyacrylamide gel. Gel fractionated proteins were transferred by electroblotting to Immobilon-P hybridization membranes (Millipore, Bedford, Mass.) and HRR25 was detected by probing the membrane with a rabbit antibody [Demaggio et al., Proc. Natl. Acad. Sci. (USA) 89: 7008–7012 (1992)] raised to HRR25. The Western blot was developed for immunoreactivity using an alkaline phosphatase-conjugated secondary antibody and colorimetric development (BioRad).

A photograph of the gel is presented in FIG. 1, wherein the approximately 58 kD HRR25 protein was detected in association with TIH2 protein.

While the present invention has been described in terms of specific methods and compositions, it is understood that variations and modifications will occur to those skilled in the art. Therefore, only such limitations as appear in the claims should be placed on the invention.

---

What is claimed is:

1. A purified and isolated TIH1 polypeptide consisting of the amino acid sequence comprising the sequence set out in SEQ ID NO: 3.

\* \* \* \* \*

UNITED STATES PATENT AND TRADEMARK OFFICE
CERTIFICATE OF CORRECTION

PATENT NO. : 5,728,806
DATED : March 17, 1998
INVENTOR(S) : DeMaggio et al.

It is certified that error appears in the above-identified patent and that said Letters Patent is hereby corrected as shown below:

On the title page, item [56] under Other Publications;

Col. 1, Anderson: Please delete "aequence", and insert - -sequence- -.

Col. 1, DeMaggio et al.: Please delete "e tal", and insert - -et al.- -.

Pg. 1, Col. 2, Hubbard and Cohen: Please delete "phosphorlyation", and insert -- phosphorylation- -.

Col. 2, Wang, et al. Please delete "Saccaromyces", and insert - -Saccharomyces- -.

Col. 2, Watson et al.: Please delete "739", and insert - -79--.

Col. 2, line 34: Please delete "an", and insert - -art- -.

Col. 6, line 45: Please delete "Itargets", and insert --Targets--.

Col. 10, line 28: Please delete "KIF2", and insert - -KIP2- -.

Col. 10, line 44: Please delete "KIF2", and insert - -KIP2- -.

Col. 11, line 48: Please delete "ATT", and insert - -ATT- -.

UNITED STATES PATENT AND TRADEMARK OFFICE
CERTIFICATE OF CORRECTION

PATENT NO. : 5,728,806
DATED : March 17, 1998
INVENTOR(S) : DeMaggio et al.

It is certified that error appears in the above-identified patent and that said Letters Patent is hereby corrected as shown below:

Col. 14, line 29: Please delete "heterologous", and insert - -heterozygous- -.

Col. 14, line 32: Please delete "HRR25/::URA3", and insert - -HRR25/hrr25::URA3- -.

Col. 16, line 14: Please delete "pepstalin", and insert - -pepstatin- -.

Signed and Sealed this

Thirty-first Day of October, 2000

Q. TODD DICKINSON

*Attest:*

*Attesting Officer*     Director of Patents and Trademarks